United States Patent [19]

Sohda et al.

[11] Patent Number: 5,719,157
[45] Date of Patent: Feb. 17, 1998

[54] PHARMACEUTICAL COMPOSITION CONTAINING QUINOLINE OR QUINAZOLINE DERIVATIVES

[75] Inventors: Takashi Sohda, Takatsuki; Shigehisa Taketomi, Ikeda; Atsuo Baba, Ashiya, all of Japan

[73] Assignee: Takeda Chemical Industries, Ltd., Osaka, Japan

[21] Appl. No.: 756,189

[22] Filed: Nov. 25, 1996

Related U.S. Application Data

[63] Continuation of Ser. No. 265,793, Jun. 27, 1994, abandoned.

[30] Foreign Application Priority Data

Jun. 29, 1993 [JP] Japan .................. 5-158652

[51] Int. Cl.$^6$ .................. A61K 31/47; A01N 43/42; A01N 43/54
[52] U.S. Cl. .................. 514/259; 514/311; 514/312
[58] Field of Search .................. 514/259, 311, 514/312

[56] References Cited

U.S. PATENT DOCUMENTS

| | | | |
|---|---|---|---|
| 4,146,719 | 3/1979 | Irikura | 544/363 |
| 4,343,940 | 8/1982 | Kreighbaum et al. | 544/283 |
| 5,023,261 | 6/1991 | Kamijo et al. | 514/285 |
| 5,064,833 | 11/1991 | Ife et al. | 514/260 |
| 5,124,325 | 6/1992 | Kojima et al. | 514/224.2 |
| 5,126,351 | 6/1992 | Luzzio et al. | 514/291 |

FOREIGN PATENT DOCUMENTS

| | | | |
|---|---|---|---|
| 0 403 185 A3 | 12/1990 | European Pat. Off. | A61K 31/255 |
| 0 530 639 A1 | 8/1992 | European Pat. Off. | |
| 0 499 926 A1 | 10/1992 | European Pat. Off. | |
| 0 567 107 A1 | 10/1993 | European Pat. Off. | C07D 401/12 |
| 0567107 | 10/1993 | European Pat. Off. | |
| 0 608 870 A1 | 1/1994 | European Pat. Off. | |
| 0 608 870 A1 | 8/1994 | European Pat. Off. | C07D 401/06 |
| 0608870 | 8/1994 | European Pat. Off. | |
| 2134169 | 4/1971 | France. | |

OTHER PUBLICATIONS

Registry File Search Results—P067384B, pp. 47, 70, 77, 85, 102 and 179.
Result of CAS Online Search CA80(15):82872z.
Synthesis (9), 718–719, 1979.
IL Farmaco 44 (6), 555–563, 1989.

*Primary Examiner*—Gary Geist
*Assistant Examiner*—Rosalynd A. Keys
*Attorney, Agent, or Firm*—Foley & Lardner

[57] ABSTRACT

The present invention provides a pharmaceutical composition for inhibiting bone resorption or for preventing or treating osteoporosis which comprises a quinoline or quinazoine derivative as an active ingredient.

52 Claims, No Drawings

PHARMACEUTICAL COMPOSITION CONTAINING QUINOLINE OR QUINAZOLINE DERIVATIVES

This application is a continuation of application Ser. No. 08/265,793, filed Jun. 27, 1994, abandoned.

FIELD OF THE INVENTION

The present invention relates to a pharmaceutical composition containing a quinoline or quinazoline derivative which has inhibitory activity of bone resorption and is useful as a prophylactic or therapeutic agent against osteoporosis.

BACKGROUND OF THE INVENTION

Osteoporosis is a morbid state or disease wherein bone mass is so decreased as to cause some symptoms or danger. Its main symptoms are kyphosis of spine and fracture of lumber vertebrae, thoracic vertebrae, femoral neck, distal ends of radii, ribs, the proximal ends of humeri or the like. In normal bone tissues, destruction by bone formation and bone resorption are repeated with a balance. Osteoblasts and osteoclasts play major roles in bone formation and bone resorption, respectively. When the balance between bone formation and bone resorption is lost and bone resorption exceeds bone formation, bone mass is decreased. Therefore, it is believed that drugs inhibiting bone resorption are useful for preventing and treating osteoporosis, and bone resorption inhibitors such as estrogen, calcitonin and the like have been administered as drugs for treating osteoporosis.

However, in the administration of these drugs, the subject is limited and the resulting effects are sometimes uncertain, and satisfactory effects have not been obtained. Thus, it is desired to develop a novel agent of preventing or treating the increase of bone resorption.

OBJECTS OF THE INVENTION

The main object of the present invention is to provide a pharmaceutical composition for inhibiting bone resorption.

Another object of the present invention is to provide a pharmaceutical composition for preventing or treating osteoporosis.

These objects as well as other objects and advantages of the present invention will become apparent to those skilled in the art from the following description.

SUMMARY OF THE INVENTION

The present inventors have intensively studied to develop generally applicable pharmaceutical compositions which have a direct effect on bones to inhibit bone resorption. As a result, it has been found that quinoline or quinazoline derivatives of the following formula (I) have a direct effect on bones to exhibit potent inhibitory activity of bone resorption.

That is, the present invention provides a pharmaceutical composition for inhibiting bone resorption which comprises as an active ingredient a compound of the formula (I):

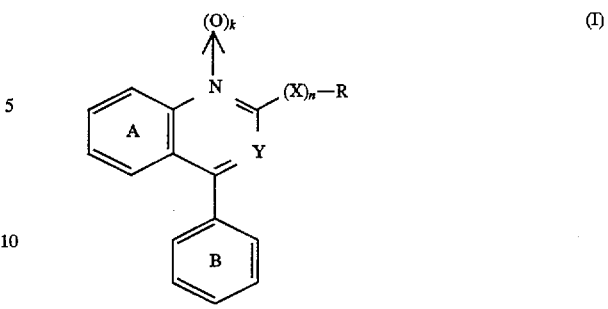

wherein

Y is a nitrogen atom or C—G in which G is an optionally esterified or optionally amidated carboxyl group, or hydroxymethyl group;

R is an optionally substituted hydrocarbon group or optionally substituted heterocyclic group;

X is an oxygen atom or optionally oxidized sulfur atom;

n is 0 or 1;

k is 0 or 1;

G and R may be linked together to form a ring;

each of the ring A and ring B may optionally be substituted;

or a pharmaceutically acceptable salt thereof.

The present invention also provides a pharmaceutical composition for preventing or treating osteoporosis which comprises as an active ingredient a compound of the above formula (I).

DETAILED DESCRIPTION OF THE INVENTION

Several compounds included in the compound (I) used in the present invention are novel and the present applicant have already filed on these compounds (Japanese Patent Application Nos. 5-012628 and 5-095780).

The optionally substituted hydrocarbon residue represented by R is preferably a group of the formula:

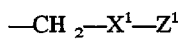

wherein $X^1$ is an oxygen atom, optionally oxidized sulfur atom or —$(CH_2)_m$— (wherein m is an integer of 0 to 5), and $Z^1$ is an optionally substituted hydrocarbon group, optionally substituted heterocyclic group or optionally substituted amino group.

Examples of the hydrocarbon group of the optionally substituted hydrocarbon group represented by R or $Z^1$ in the above formula (I) include aliphatic hydrocarbon groups, alicyclic hydrocarbon groups, alicyclic-aliphatic hydrocarbon groups, (aromatic carbocycle)-aliphatic hydrocarbon groups, aromatic hydrocarbon groups and the like.

Examples of such aliphatic hydrocarbon groups include saturated aliphatic hydrocarbon groups having 1 to 8 carbon atoms such as methyl, ethyl, propyl, isopropyl, butyl, isobutyl, sec-butyl, t-butyl, pentyl, isopentyl, neopentyl, t-pentyl, hexyl, isohexyl, heptyl, octyl and the like; unsaturated aliphatic hydrocarbon groups having 2 to 8 carbon atoms such as ethenyl, 1-propenyl, 2-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 3-hexenyl, 2,4-hexadienyl, 5-hexenyl, 1-heptenyl, 1-octenyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 3-hexynyl, 2,4-hexadiynyl, 5-hexynyl, 1-heptynyl, 1-octynyl and the like.

Examples of such alicyclic hydrocarbon groups include saturated alicyclic hydrocarbon groups having 3 to 7 carbon atoms such as cyclopropyl, cyclobutyl, cyclopentyl, cyclohexyl, cycloheptyl and the like; and unsaturated alicyclic hydrocarbon groups having 5 to 7 carbon atoms such as 1-cyclopentenyl, 2-cyclopentenyl, 3-cyclopentenyl, 1-cyclohexenyl, 2-cyclohexenyl, 3-cyclohexenyl, 1-cycloheptenyl, 2-cycloheptenyl, 3-cycloheptenyl, 2,4-cycloheptadienyl and the like.

Examples of such alicyclic-aliphatic hydrocarbon groups include those having 4 to 9 carbon atoms each of which is composed of the above alicyclic hydrocarbon group and aliphatic hydrocarbon group, for example, cyclopropylmethyl, cyclopropylethyl, cyclobutylmethyl, cyclopentylmethyl, 2-cyclopentenylmethyl, 3-cyclopentenylmethyl, cyclohexylmethyl, 2-cyclohexenylmethyl, 3-cyclohexenylmethyl, cyclohexylethyl, cyclohexylpropyl, cycloheptylmethyl, cycloheptylethyl and the like.

Examples of such (aromatic carbocycle)-aliphatic hydrocarbon groups include phenyl alkyl having 7 to 9 carbon atoms such as benzyl, phenethyl, 1-phenylethyl, 3-phenylpropyl, 2-phenylpropyl, 1-phenylpropyl and the like; naphthylalkyl having 11 to 13 carbon atoms such as α-naphthylmethyl, α-naphthylethyl, β-naphthylmethyl, β-naphthylethyl and the like.

Examples of such aromatic hydrocarbon groups include phenyl, naphthyl (e.g., α-naphthyl, β-naphthyl) and the like.

Examples of the oxidized sulfur atom represented by $X^1$ include a thio group, sulfinyl group and sulfonyl group. In particular, a thio group is preferred.

$X^1$ is preferably —$(CH_2)_m$— wherein m is 1 or 2.

Examples of the optionally substituted hydrocarbon group represented by $Z^1$ include the same optionally substituted hydrocarbon groups as those described above for R.

Examples of the optionally substituted heterocyclic group represented by $Z^1$ include the same optionally substituted heterocyclic groups as those described below for R. It is preferably aromatic 5-membered heterocyclic groups containing 2 or 3 heteroatoms (e.g., oxygen atom, nitrogen atom and sulfur atom), more preferably 1,2,4-triazol-1-yl.

Examples of the heterocyclic group of the optionally substituted heterocyclic group represented by R or $Z^1$ in the above formula (I) include 5- to 7-membered heterocyclic groups containing one sulfur atom, nitrogen atom or oxygen atom; 5- to 6-membered heterocyclic groups containing 2 to 4 nitrogen atoms; 5- to 6-membered heterocyclic groups containing 1 to 2 nitrogen atoms, and one sulfur atom or oxygen atom. Each of these heterocyclic group may form a condensed ring with a 6-membered ring containing up to 2 nitrogen atoms, benzene ring or 5-membered ring containing one sulfur atom.

Specific examples of the heterocyclic group include 2-pyridyl, 3-pyridyl, 4-pyridyl, 2-pyrimidinyl, 4-pyrimidinyl, 5-pyrimidinyl, 6-pyrimidinyl, 3-pyridazinyl, 4-pyridazinyl, 2-pyrazinyl, 2-pyrrolyl, 3-pyrrolyl, 2-imidazolyl, 4-imidazolyl, 5-imidazolyl, 3-pyrazolyl, 4-pyrazolyl, isothiazolyl, isoxazolyl, 2-thiazolyl, 4-thiazolyl, 5-thiazolyl, 2-oxazolyl, 4-oxazolyl, 5-oxazolyl, 1,2,4-triazol-3-yl, 1,3,4-triazol-2-yl, 1,2,3-triazol-4-yl, tetrazol-5-yl, benzimidazol-2-yl, indol-3-yl, benzpyrazol-3-yl, 1H-pyrrolo[2,3-b]pyrazin-2-yl, 1H-pyrrolo[2,3-b]pyridin-6-yl, 1H-imidazo[4,5-b]pyridin-2-yl, 1H-imidazo[4,5-c]pyridin-2-yl, 1H-imidazo[4,5-b]pyrazin-2-yl and the like.

Each of the hydrocarbon groups and heterocyclic groups represented by R or $Z^1$ in the above formula (I) may be unsubstituted or have 1 to 3 substituents at any possible position in the ring. Such substituents include, for example, aliphatic chain hydrocarbon groups, alicyclic hydrocarbon groups, aryl groups, aromatic heterocyclic groups, non-aromatic heterocyclic groups, halogen atoms, nitro group, optionally substituted amino group, optionally substituted acyl groups, optionally substituted hydroxyl group, optionally substituted thiol group, optionally esterified carboxyl group and the like.

The aliphatic chain hydrocarbon group as the substituent of the hydrocarbon group or heterocyclic group represented by R or $Z^1$ include, for example, straight chain or branched chain aliphatic hydrocarbon groups such as alkyl groups, preferably alkyl groups having 1 to 10 carbon atoms; alkenyl groups, preferably alkenyl groups having 2 to 10 carbon atoms; alkynyl groups and the like.

Preferred examples of the alkyl group include methyl, ethyl, propyl, isopropyl, butyl, isobutyl, sec-butyl, tert-butyl, pentyl, isopentyl, neopentyl, tert-pentyl, 1-ethylpropyl, hexyl, isohexyl, 1,1-dimethylbutyl, 2,2-dimethylbutyl, 3,3-dimethylbutyl, 2-ethylbutyl, hexyl, pentyl, octyl, nonyl, decyl and the like.

Preferred examples of the alkenyl include vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl and the like.

Preferred examples of the alkynyl include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like.

The alicyclic hydrocarbon group as the substituent of the hydrocarbon group or heterocyclic group represented by R or $Z^1$ include, for example, saturated or unsaturated alicyclic hydrocarbon groups such as cycloalkyl, cycloalkenyl, cycloalkadienyl and the like.

Preferred examples of the cycloalkyl include that having 3 to 10 carbon atoms such as cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl, bicyclo[3.2.2]nonyl, bicyclo[3.3.1]nonyl, bicyclo[4.2.1]nonyl, bicyclo[4.3.1]decyl and the like.

Preferred examples of the cycloalkenyl include that having 5 to 7 carbon atoms such as 2-cyclopenten-1-yl, 3-cyclopenten-1-yl, 2-cyclohexen-1-yl, 3-cyclohexen-1-yl and the like.

Preferred examples of the cycloalkadienyl include that having 5 to 7 carbon atoms such as 2,4-cyclopentadien-1-yl, 2,4-cyclohexadien-1-yl, 2,5-cyclohexadien-1-yl and the like.

The aryl group as the substituent of the hydrocarbon group or heterocyclic group represented by R or $Z^1$ means a monocyclic or condensed polycyclic aromatic hydrocarbon group. Preferred examples thereof include phenyl, naphthyl, anthryl, phenanthryl, acenaphthylenyl and the like. More preferred examples thereof are phenyl, 1-naphthyl, 2-naphthyl and the like.

Preferred examples of the aromatic heterocyclic group as the substituent of the hydrocarbon group or heterocyclic group represented by R or $Z^1$ include aromatic monocyclic heterocyclic groups such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like: aromatic condensed heterocyclic groups such as benzofuranyl, isobenzofuranyl, benzo[b]thienyl, indolyl, isoindolyl, 1H-indazolyl, benzimidazolyl, benzoxazolyl, 1,2-benzisoxazolyl, benzothiazolyl, 1,2-benzisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like.

Preferred examples of the non-aromatic heterocyclic group as the substituent of the hydrocarbon group or heterocyclic group represented by R or $Z^1$ include oxiranyl, azetidinyl, oxetanyl, thietanyl, pyrrolidinyl, tetrahydrofuranyl, thiolanyl, piperidinyl, tetrahydropyranyl, morpholinyl, thiomorpholinyl, piperazinyl and the like.

The halogen as the substituent of the hydrocarbon group or heterocyclic group represented by R or $Z^1$ includes, for example, fluorine, chlorine, bromine and iodine. In particular, fluorine and chlorine are preferred.

The optionally substituted amino group as the substituent of the hydrocarbon group or heterocyclic group represented by R or $Z^1$ includes, for example, an amino group and an amino group substituted with one or two substituents such as alkyl having 1 to 10 carbon atoms, alkenyl having 1 to 10 carbon atoms or aromatic groups (e.g., methylamino, dimethylamino, ethylamino, diethylamino, dibutylamino, diallylamino, cyclohexylamino, phenylamino, N-methyl-N-phenylamino, etc.).

The optionally substituted acyl group as the substituent of hydrocarbon group or heterocyclic group represented by R or $Z^1$ includes, for example, formyl, and $(C_{1-10}$ alkyl)-carbonyl, $(C_{1-10}$ alkenyl)-carbonyl and aromatic carbonyl (e.g., acetyl, propionyl, butyryl, isobutyryl, valeryl, isovaleryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl, benzoyl, nicotinoyl, etc.).

The optionally substituted hydroxyl group of the substituent of the hydrocarbon group or heterocyclic group represented by R or $Z^1$ includes, for example, a hydroxyl group and a hydroxyl group having an appropriate substituent such as a protecting group for a hydroxyl group. Examples of the hydroxyl group having such a substituent include alkoxy, alkenyloxy, aralkyloxy, acyloxy, aryloxy and the like.

Preferred examples of the alkoxy include that having 1 to 10 carbon atoms such as methoxy, ethoxy, propoxy, isopropoxy, butoxy, isobutoxy, sec-butoxy, tert-butoxy, pentyloxy, isopentyloxy, neopentyloxy, hexyloxy, heptyloxy, nonyloxy, cyclobutyloxy, cyclopentyloxy, cyclohexyloxy and the like.

Examples of the alkenyloxy include that having 1 to 10 carbon atoms such as allyloxy, crotyloxy, 2-pentenyloxy, 3-hexenyloxy, 2-cyclopentenylmethoxy, 2-cyclohexenylmethoxy and the like.

Examples of the aralkyloxy include phenyl-$C_{1-4}$ alkyloxy (e.g., benzyloxy, phenethyloxy, etc.).

Preferred examples of the acyloxy include alkanoyloxy having 2 to 4 carbon atoms such as acetyloxy, propionyloxy, n-butyryloxy, iso-butyryloxy and the like.

Examples of the aryloxy include phenoxy, 4-chlorophenoxy and the like.

The optionally substituted thiol group as the substituent of the hydrocarbon group or heterocyclic group represented by R or $Z^1$ includes, for example, a thiol group and a thiol group having an appropriate substituent such as a protecting group for a thiol group. Examples of the thiol group having such a substituent include alkylthio, aralkylthio, acylthio and the like.

Preferred examples of the alkylthio include alkylthio having 1 to 10 carbon atoms such as methylthio, ethylthio, propylthio, isopropylthio, butylthio, isobutyltho, sec-butylthio, tert-butylthio, pentylthio, isopentylthio, neopentylthio, hexylthio, heptylthio, nonylthio, cyclobutylthio, cyclopentylthio, cyclohexylthio and the like.

Examples of the aralkylthio include phenyl-$C_{1-4}$ alkylthio (e.g., benzylthio, phenetylthio, etc.).

Preferred examples of the acylthio include alkanoylthio having 2 to 4 carbon atoms such as acetylthio, propionylthio, n-butyrylthio, iso-butyrylthio and the like.

The optionally esterified carboxyl group as the substituent of the hydrocarbon group or heterocyclic group represented by R or $Z^1$ include, for example, a carboxyl group, $(C_{1-6}$ alkoxy)-carbonyl (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl, etc.), $(C_{3-6}$ alkenyloxy)carbonyl (e.g., allyloxycarbonyl, crotyloxycarbonyl, 2-pentenyloxycarbonyl, 3-hexenyloxycarbonyl, etc.), aralkyloxycarbonyl (e.g., benzyloxycarbonyl, phenethyloxycarbonyl, etc.) and the like.

The substituent of the hydrocarbon group and heterocyclic group represented by R or $Z^1$ in the above formula (I) may have at least one, preferably 1 to 3 appropriate substituents. Such substituents include, for example, lower alkyl groups, lower alkenyl groups, lower alkynyl groups, cycloalkyl groups, aryl groups, aromatic heterocyclic groups, non-aromatic heterocyclic groups, aralkyl groups, an amino group, N-monosubstituted amino groups, N,N-disubstituted amino groups, an amidino group, acyl groups, a carbamoyl group, N-monosubstituted carbamoyl groups, N,N-disubstituted carbamoyl groups, a sulfamoyl group, N-monosubstituted sulfamoyl groups, N,N-disubstituted sulfamoyl groups, a carboxyl group, lower alkoxycarbonyl, a hydroxyl group, lower alkoxy groups, lower alkenyloxy groups, cycloalkyloxy groups, lower alkylthio groups, aralkylthio groups, arylthio groups, a sulfo group, a cyano group, an azido group, halogen atoms, a nitro group, a nitroso group and the like. Specific examples of these substituents include those described above with respect to the substituents of the hydrocarbon group and heterocyclic group represented by R or $Z^1$.

When R is —$CH_2$—$X^1$—$Z^1$ in the formula (I), the optionally substituted amino group represented by $Z^1$ is represented by the formula: —$N(R^1)(R^2)$ wherein $R^1$ and $R^2$ are the same or different and are hydrogen, optionally substituted hydrocarbon group or optionally substituted heterocyclic group.

The hydrocarbon group in the optionally substituted hydrocarbon group and heterocyclic group in the optionally substituted heterocyclic group represented by $R^1$ or $R^2$ include, for example, the same hydrocarbon groups and heterocyclic groups as those represented by R.

$R^1$ and $R^2$ may be linked together to form a ring. Examples of such -$N(R^1)(R^2)$ include 1-pyrrolidinyl, 1-imidazolidinyl, 1-pyrazolidinyl, 1-piperidinyl, 1-piperazinyl, 4-morpholinyl, 4-thiomorpholinyl, homopiperazin-1-yl, 1,2,4-triazol-1-yl, 1,3,4-triazol-1-yl, pyrazol-1-yl, imidazol-1-yl, 1,2,3-triazol-1-yl, 1,2,3-triazol-2-yl, tetrazol-1-yl, benzimidazol-1-yl, indol-1-yl, 1H-indazol-1-yl and the like.

Each of the hydrocarbon group and heterocyclic group represented by $R^1$ or $R^2$ may have 1 to 3 substituents at any possible position in the ring. Examples of the substituent include the same substituents as those of the hydrocarbon group or heterocyclic group represented by R. These substituents of the hydrocarbon group and heterocyclic group represented by $R^1$ or $R^2$ each may have at least one, preferably 1 to 3 appropriate substituents. Such substituents include, for example, lower alkyl groups, lower alkenyl groups, lower alkynyl groups, cycloalkyl groups, aryl groups, aromatic heterocyclic groups, non-aromatic heterocyclic groups, aralkyl groups, an amino group, N-monosubstituted amino groups, N,N-disubstituted amino groups, an amidino group, acyl groups, a carbamoyl group, N-monosubstituted carbamoyl groups, N,N-disubstituted carbamoyl groups, a sulfamoyl group, N-monosubstituted sulfamoyl groups, N,N-disubstituted sulfamoyl groups, a carboxyl group, lower alkoxycarbonyl groups, a hydroxyl group, lower alkoxy groups, lower alkenyloxy groups, cycloalkyloxy groups, aralkyloxy groups, aryloxy groups, a mercapto group, lower alkylthio groups, aralkylthio groups, arylthio groups, a sulfo group, a cyano group, an azido group, a nitro group, a nitroso group, halogen and the like. Specific examples of these substituents include those described above with respect to the substituents of the hydrocarbon group and heterocyclic group represented by R.

Examples of the optionally oxidized sulfur atom represented by X include a thio group, sulfinyl group and sulfonyl group. In particular, a thio group is preferred.

Each of the ring A and ring B in the formula (I) may be substituted with at least one substituent. Examples of the substituent include halogen atoms, a nitro group, optionally substituted alkyl groups, an optionally substituted hydroxyl group, an optionally substituted thiol group, an optionally substituted amino group, optionally substituted acyl groups, an optionally esterified carboxyl group and optionally substituted aromatic cyclic groups.

The halogen atom as the substituent of the ring A and ring B includes, for example, fluorine, chlorine, bromine and iodine. In particular, fluorine and chlorine are preferred.

The optionally substituted alkyl group as the substituent of the ring A and ring B may be, for example, any of straight-chain, branched-chain or cyclic alkyl groups. Specific examples thereof include methyl, ethyl, propyl, isopropyl, butyl, isobutyl, sec-butyl, tert-butyl, pentyl, isopentyl, neopentyl, hexyl, heptyl, octyl, nonyl, decyl, cycloproyl, cyclobutyl, cyclopentyl, cyclohexyl, cycloheptyl and the like.

The optionally substituted hydroxyl group as the substituent of the ring A and ring B includes, for example, a hydroxyl group and a hydroxyl group having an appropriate substituent such as that used as a protecting group for a hydroxyl group (e.g., alkoxy, alkenyloxy, aralkyloxy, acyloxy, aryloxy, etc.).

Preferred examples of the alkoxy include that having 1 to 10 carbon atoms such as methoxy, ethoxy, propoxy, isopropoxy, butoxy, isobutoxy, sec-butoxy, tert-butoxy, pentyloxy, isopentyloxy, neopentyloxy, hexyloxy, heptyloxy, nonyloxy, cyclobutyloxy, cyclopentyloxy, cyclohexyloxy and the like.

Examples of the alkenyloxy include that having 1 to 10 carbon atoms such as allyloxy, crotyloxy, 2-pentenyloxy, 3-hexenyloxy, 2'-cyclopentenylmethoxy, 2-cyclohexenylmethoxy and the like.

Examples of the aralkyloxy include phenyl-$C_{1-4}$ alkyloxy (e.g., benzyloxy, phenethyloxy, etc.).

Preferred examples of the acyloxy include alkanoyloxy having 2 to 4 carbon atoms such as acetyloxy, propionyloxy, n-butyryloxy, iso-butyryloxy and the like.

Examples of the aryloxy include phenoxy, 4-chlorophenoxy and the like.

The optionally substituted thiol as the substituent of the ring A and ring B includes, for example, a thiol group and a thiol group having an appropriate substituent such as that used as a protecting group for a thiol group (e.g., alkylthio, aralkylthio, acylthio, etc.).

Preferred examples of the alkylthio include that having 1 to 10 carbon atoms such as methylthio, ethylthio, propylthio, isopropylthio, butylthio, isobutylthio, sec-butylthio, tert-butylthio, pentylthio, isopentylthio, neopentylthio, hexylthio, heptylthio, nonylthio, cyclobutylthio, cyclopentylthio, cyclohexylthio and the like.

Examples of the aralkylthio include phenyl-$C_{1-4}$ alkylthio (e.g., benzylthio, phenethylthio, etc.).

Preferred examples of the acylthio include alkanoylthio having 2 to 4 carbon atoms such as acetylthio, propionylthio, n-butyrylthio, iso-butyrylthio and the like.

The optionally substituted amino group as the substituent of the ring A and ring B includes, for example, an amino group and an amino group substituted with one or two substituents selected from alkyl groups having 1 to 10 carbon atoms, alkenyl groups having 1 to 10 carbon atoms and aromatic groups. Specific examples of the substituted amino group include methylamino, dimethylamino, ethylamino, diethylamino, dibutylamino, diallylamino, cyclohexylamino, phenylamino, N-methyl-N-phenylamino and the like.

The acyl group as the substituent of the ring A and ring B include, for example, formyl, and ($C_{1-10}$ alkyl)-carbonyl, ($C_{1-10}$ alkenyl)-carbonyl and (aromatic group)-carbonyl such as acetyl, propionyl, butyryl, isobutyryl, valeryl, pivaloyl, hexanoyl, heptanoyl, octanoyl, cyclobutanecarbonyl, cyclopentanecarbonyl, cyclohexanecarbonyl, cycloheptanecarbonyl, crotonyl, 2-cyclohexenecarbonyl benzoyl, nicotinoyl and the like, The optionally esterified carboxyl group as the substituent of the ring A and ring B includes, for example, a carboxyl group, ($C_{1-6}$ alkyloxy)-carbonyl (e,g, methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl, etc.), ($C_{3-6}$ alkenyloxy)-carbonyl (e.g., allyloxycarbonyl, crotyloxycarbonyl, 2-pentenyloxycarbonyl, 3-hexenyloxycarbonyl, etc.), aralkyloxycarbonyl (e.g., benzyloxycarbonyl, phenethyloxycarbonyl, etc.) and the like.

The aromatic cyclic group as the substituent of the ring A and ring B includes, for example, $C_{6-14}$ aromatic hydrocarbon groups (e.g., phenyl, naphthyl, anthryl, etc.) and aromatic heterocyclic groups (e.g., pyridyl, furyl, thienyl, imidazolyl, thiazolyl, etc.).

The substituent of the ring A and ring B may be at any possible position in each ring. The each ring may be substituted with the same or different 1 to 4 substituents. When the substituents of the ring A or ring B are adjacent to each other, the adjacent substituents are linked together to form a group of the formula: —$(CH_2)_t$— or —O—$(CH_2)_l$—O— (wherein t is an integer of 3 to 5 and l is an integer of 1 to 3) which may form a 5- to 7-membered ring with carbon atoms of the benzene ring.

Preferably, the ring A is substituted with at least one alkoxy group, preferably at least one methoxy group; or the same or different two alkoxy groups, preferably two methoxy groups. More preferably, the ring A is substituted with two methoxy groups at the 6- and 7-positions of the quinoline ring or quinazoline ring.

Preferably, the ring B is substituted with at least one alkoxy group, preferably at least one methoxy group or isopropoxy group; or the same or different two alkoxy groups. More preferably, the ring B is substituted with an isopropoxy group at the 3-position and a methoxy group at the 4-position.

When the compound of the formula (I) is a quinoline derivative wherein Y is C—G, the optionally esterified carboxyl group represented by G may be, for example, a carboxyl group, alkyloxycarbonyl groups, aralkyloxycarbonyl groups and the like.

The alkyl group of the alkyloxycarbonyl group includes, for example, alkyl groups having 1 to 6 carbon atoms such as methyl, ethyl, propyl, isopropyl, butyl, isobutyl, sec-butyl, tert-butyl and the like.

The aralkyl group of the aralkyloxycarbonyl group means an alkyl group having an aryl group as a substituent (i.e., arylalkyl group). Examples of the aryl group include phenyl, naphthyl and the like. The aryl group may have the same substituent as that of the above ring A. The alkyl group is preferably a lower alkyl group having 1 to 6 carbon atoms. Preferred examples of the aralkyl group include benzyl, phenethyl, 3-phenylpropyl, (1-naphthyl)methyl, (2-naphthyl)methyl and the like. In particular, benzyl, phenethyl and the like are preferred.

When G is an amidated carboxyl group, the amidated carboxyl group is represented by —CON($R^1$)($R^2$) wherein each symbol is as defined above.

When the compound of the formula (I) is a quinoline derivative wherein Y is C—G, R and G may be linked together to form a 5-membered ring. The resulting compound is represented, for example, by the following formulas (II) or (III).

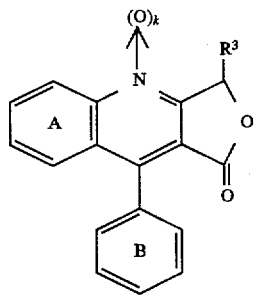

(II)

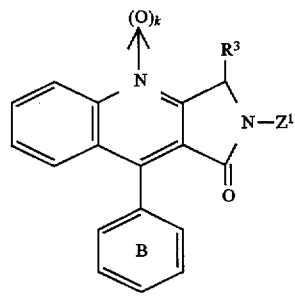

(III)

wherein $R^3$ is hydrogen, an optionally substituted hydrocarbon group or optionally substituted heterocyclic group, and the other symbols are as defined above.

The optionally substituted hydrocarbon group and optionally substituted heterocyclic group represented by $R^3$ in the formulas (II) and (III) includes, for example, the same groups as described for R or $Z^1$.

Y in the formula (I) is preferably C—G. More preferably, G is a ($C_{1-6}$ alkyl)oxycarbonyl group, particularly preferably an ethoxycarbonyl group.

n in the formula (I) is preferably 0.

k in the formula (I) is preferably 0.

Preferred examples of the compound of the formula (I) include:

methyl 4-(3,4-dimethoxyphenyl)-2-ethyl-6,7-dimethoxyquinoline-3-carboxylate;

ethyl 6-chloro-2-methyl-4-(3,4-dimethoxyphenyl)quinoline-3-carboxylate;

6,7-dimethoxy-9-phenylfuro[3,4-b]quinoline-1(3H)-one;

ethyl 4-(3,4-dimethoxyphenyl)-6,7-dimethoxy-2-[(1-methylimidazol-2-yl)thiomethyl]quinoline-3-carboxylate;

4-(3,4-dimethoxyphenyl)-2-(2-hydroxyethylthiomethyl)-6,7-dimethoxyquinazoline;

4-(3,4-dimethoxyphenyl)-6,7-dimethoxy-2-[(4-methyl-1,2,4-triazol-3-yl)thiomethyl]quinazoline;

ethyl 4-(3,4-dimethoxyphenyl)-6,7-dimethoxy-2-[2-(1-methylimidazol-2-yl)ethyl]quinoline-3-carboxylate;

methyl 4-(3,4-dimethoxyphenyl)-6,7-dimethoxy-3-methoxycarbonylquinoline-2-acetate;

ethyl 4-(3,4-dimethoxyphenyl)-6,7-dimethoxy-2-(1,2,4-triazol-1-ylmethyl)quinoline-3-carboxylate;

ethyl 4-(3-isopropoxy-4-methoxyphenyl)-6,7-dimethoxy-2-(1,2,4-triazol-1-ylmethyl)quinoline-3-carboxylate;

ethyl 4-(4-hydroxy-3-methoxyphenyl)-6,7-dimethoxy-2-(1,2,4-triazol-1-ylmethyl)quinoline-3-carboxylate;

ethyl 7-hydroxy-6-methoxy-4-(3,4-dimethoxyphenyl)-2-(1,2,4-triazol-1-ylmethyl)quinoline-3-carboxylate;

ethyl 4-(3,4-dimethoxyphenyl)-6,7-dimethoxy-2-(1,2,4-triazol-1-ylmethyl)quinoline-3-carboxylate 1-oxide; and ethyl 2-(N,N-diethylaminomethyl)-4-(3,4-dimethoxyphenyl)-6,7-dimethoxyquinoline-3-carboxylate.

In particular, the compound of the formula (I) is preferably that wherein Y is C—G in which G is ethoxycarbonyl, R is —$CH_2$—$Z^1$, $Z^1$ is 1,2,4-triazol-1-yl, the ring A is substituted with methoxy groups at the 6- and 7-positions of the quinoline ring, the ring B is substituted with methoxy groups at the 3- and 4-positions, n is 0, and k is 0.

The salt of the compound of the formula (I) is preferably a pharmaceutically acceptable salt. Examples thereof include salts with inorganic bases, organic bases, inorganic acids, organic acids, basic or acidic amino acids and the like.

Preferred examples of the salts with inorganic bases include alkaline metal salts such as a sodium salt, potassium salt and the like; alkaline earth metal salts such as a calcium salt, magnesium salt and the like; an aluminium salt; an ammonium salt and the like.

Preferred examples of the salts with organic bases include salts with trimethylamine, triethylamine, pyridine, picoline, ethanolamine, diethanolamine, triethanolamine, dicyclohexylamine, N,N'-dibenzylethylenediamine and the like.

Preferred examples of the salts with inorganic acids include salts with hydrochloric acid, hydrobromic acid, nitric acid, sulfuric acid, phosphoric acid and the like.

Preferred examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferred examples of the salts with basic amino acids include salts with arginine, lysine, ornithine and the like. Preferred examples of the salts with acidic amino acids include aspartic acid, glutamic acid and the like.

The compound of the formula (I) can be formulated with a pharmaceutically acceptable carrier and administered orally or parenterally as solid preparations such as tablets, capsules, granules, powders or the like; or liquid preparations such as syrups, injections or the like.

As the pharmaceutically acceptable carrier, various organic or inorganic carrier materials conventionally used for pharmaceutical preparations can be used and formulated as excipients, lubricants, binders, disintegrators and the like for solid preparations; solvents, solution adjuvants, suspending agents, tonicity agents, buffering agents, soothing agents and the like for liquid preparations and the like. If necessary, pharmaceutical additives such as antiseptics, antioxidants, colorants, sweetening agents and the like can be used.

Preferred examples of the excipient include lactose, sucrose, D-mannitol, starch, crystalline cellulose, light anhydrous silicic acid and the like.

Preferred examples of the lubricant include magnesium stearate, calcium stearate, talc, colloidal silica and the like.

Preferred examples of the binder include crystalline cellulose, sucrose, D-mannitol, dextrin, hydroxypropyl cellulose, hydroxypropyl methyl cellulose, polyvinylpyrrolidone and the like.

Preferred examples of the disintegrator include starch, carboxymethylcellulose, carboxymethyl cellulose calcium, croscarmellose sodium, carboxymethyl starch sodium and the like.

Preferred examples of the solvent include water for injection, alcohols, propylene glycol, macrogol, sesame oil, corn oil and the like.

Preferred examples of the solution adjuvant include polyethylene glycol, propylene glycol, D-mannitol, benzyl benzoate, ethanol, trisaminomethane, cholesterol, triethanolamine, sodium carbonate, sodium citrate and the like.

Preferred examples of the suspending agent include surfactants such as stearyl triethanolamine, sodium lauryl sulfate, laurylaminopropionic acid, lecithin, benzalkonium chloride, benzethonium chloride, glyceryl monostearate and the like; hydrophilic polymers such as polyvinyl alcohol, polyvinyl pyrrolidone, carboxymethyl cellulose sodium, methyl cellulose, hydroxymethyl cellulose, hydroxyethyl cellulose, hydroxypropyl cellulose and the like.

Preferred examples of the tonicity agent include sodium chloride, glycerin, D-mannitol and the like.

Preferred examples of the buffering agent include buffers such as phosphates, acetates, carbonates, citrates and the like.

Preferred examples of the soothing agent include benzyl alcohol and the like.

Preferred examples of the antiseptics include parahydroxybenzoic acid esters, chlorobutanol, benzyl alcohol, phenethyl alcohol, dehydroacetic acid, sorbic acid and the like.

Preferred examples of the antioxidant include sulfites, ascorbic acid and the like.

The compound (I) used in the present invention has low toxicity. For example, the compounds of Examples 142 and 181 are orally administered to mice in a dose of 1,000 mg/kg, no mouse was died. Thus, the compound (I) is a useful agent as a bone resorption inhibitor for preventing or treating osteoporosis for mammals such as humans, cattle, horses, swine, dogs, cats and the like.

The dose of the compound (I) used in the present invention can be appropriately selected depending upon the administration route and condition of the patient to be treated. Normally, the dose can be selected from the regions of 10 mg to 500 mg per adult in the case of oral administration and 1 mg to 100 mg per adult in the case of parenteral administration. The compound in the above dose can be administered a day in one to three divided doses.

The above compound (I) can be prepared, for example, as follows.

Method A

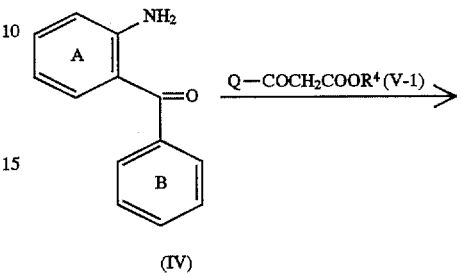

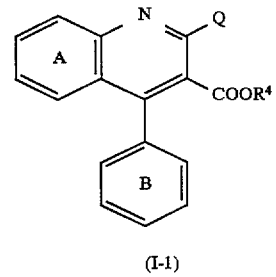

wherein Q is an optionally substituted hydrocarbon group, $R^4$ is a lower alkyl group, and the other symbols are as defined above.

The optionally substituted hydrocarbon group by Q in the formulas (I-1) and (V-1) includes the same groups as those described above for R or $Z^1$.

Examples of the lower alkyl group represented by $R^4$ in the formulas (I-1) and (V-1) include alkyl groups having 1 to 4 carbon atoms such as methyl, ethyl, propyl, isopropyl, butyl, isobutyl, sec-butyl, tert-butyl and the like.

In this method, a 2-aminobenzophenone derivative (IV) is reacted with the compound (V-1) in the presence of an acid to prepare the compound (I-1). The reaction of the compound (IV) and the compound (V-1) can be carried out in an appropriate solvent. Examples of the solvent include aromatic hydrocarbons (e.g., benzene, toluene, xylene, etc.), ethers (e.g., dioxane, tetrahydrofuran, dimethoxyethane, etc.), alcohols (e.g., methanol, ethanol, propanol, etc.), N,N-dimethylformamide, dimethyl sulfoxide, chloroform, dichloromethane, 1,2-dichloroethane, 1,1,2,2-tetrachloroethane, acetic acid and the like. The reaction of the compound (IV) and the compound (V-1) is carried out in the presence of an appropriate acid such as Lewis acids (e.g., aluminium chloride, zinc chloride, etc.), hydrochloric acid, sulfuric acid, trifluoroacetic acid, p-toluenesulfonic acid or the like. The amount of the acid to be used is preferably 0.05 to 2.0 mol per mol of the compound (IV). The reaction temperature is normally 20° C. to 200° C., preferably about 30° C. to 150° C. The reaction time is 0.5 to 20 hours, preferably 1 to 10 hours.

The compound (I-1) thus obtained can be isolated and purified by conventional separation and purification techniques such as concentration, concentration under reduced pressure, solvent extraction, crystallization, recrystallization, redistribution, chromatography and the like.

Method B

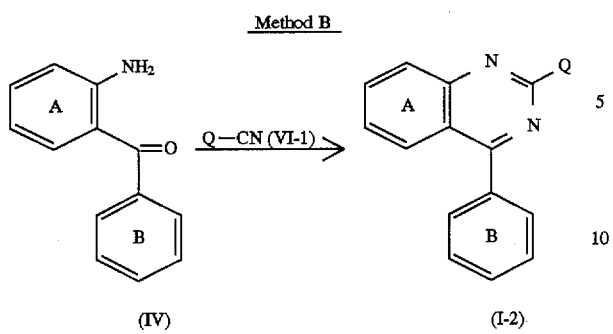

wherein each symbol is as defined above.

In this method, the 2-aminobenzophenone derivative (IV) is reacted with the nitrile derivative (VI-1) to prepare the quinazoine derivative (I-2). The reaction of the compound (IV) with the compound (VI-1) is carried out in an appropriate solvent. Examples of the solvent include aromatic hydrocarbons (e.g., benzene, toluene, xylene, etc.), ethers (e.g., dioxane, tetrahydrofuran, dimethoxyethane, etc.), N,N-dimethylformamide, dimethyl sulfoxide, chloroform, dichloromethane, 1,2-dichloroethane, 1,1,2,2-tetrachloroethane, acetic acid and the like.

The reaction of the compound (IV) with the compound (VI-1) is carried out in the presence of an appropriate acid such as Lewis acids (e.g., aluminium chloride, zinc chloride, etc.), sulfuric acid, trifluoroacetic acid, p-toluenesulfonic acid and the like. The amount of the acid to be used is about 1 to 5 mol, preferably 1 to 2 mol per mol of the compound (IV). The reaction temperature is normally 20° C. to 200° C., preferably about 30° C. to 150° C. The reaction time is 0.5 to 20 hours, preferably 1 to 10 hours. The reaction may be carried out using an excess amount of the compound (VI-1) as the solvent.

The quinazoline compound (I-2) thus obtained can be isolated and purified by conventional separation and purification techniques such as concentration, concentration under reduced pressure, solvent extraction, crystallization, recrystallization, redistribution, chromatography and the like.

Method C

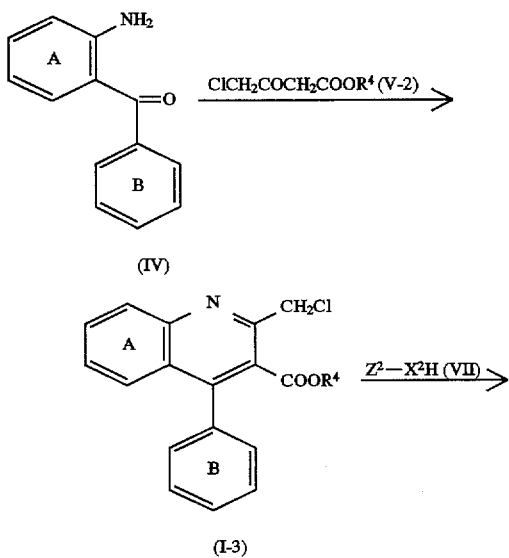

wherein $X^2$ is an oxygen atom or sulfur atom, $Z^2$ is an optionally substituted hydrocarbon group or an optionally substituted heterocyclic group whose ring-constituting carbon atom is attached to $X^2$.

Examples of the optionally substituted hydrocarbon group represented by $Z^2$ in the formulas (VII) and (I-4) include the same groups as those described above for R or $Z^1$. Examples of the optionally substituted heterocyclic group whose ring-constituting carbon atom is attached to $X^2$ include the same groups as those described above for R or $Z^1$.

In this method, the compound (I-3) is prepared according to the same manner as in the method A and then reacted with the compound (VIII) to prepare the compound (I-4). The reaction of the compound (IV) with the compound (V-2) can be carried out according to the same manner as in the method A. The reaction of the compound (I-3) with the compound (VII) is carried out in an appropriate solvent. Examples of the solvent include aromatic hydrocarbons (e.g., benzene, toluene, xylene, etc.), ethers (e.g., dioxane, tetrahydrofuran, dimethoxyethane, etc.), alcohols (e.g., methanol, ethanol, propanol, etc.), ethyl acetate, acetonitrile, pyridine, N,N-dimethylformamide, dimethyl sulfoxide, chloroform, dichloromethane, 1,2-dichloroethane, 1,1,2,2-tetrachloroethane, acetone, 2-butanone and the like. These solvents can be used alone or as a mixture thereof.

The reaction of the compound (I-3) with the compound (VII) is carried out in the presence of an appropriate base such as alkaline metal salts (e.g., sodium hydroxide, potassium hydroxide, potassium carbonate, sodium carbonate, sodium bicarbonate, etc.), silver carbonate ($Ag_2CO_3$), amines (e.g., pyridine, triethylamine, N,N-dimethylaniline, etc.), sodium hydride, potassium hydride or the like. The amount of the base to be used is preferably about 1 to 5 mol per mol of the compound (I-3). The reaction temperature is normally −20° C. to 150° C., preferably about −10° C. to 100° C.

The quinoline derivatives (I-3) and (I-4) thus obtained can be isolated and purified by conventional separation and purification techniques such as concentration, concentration under reduced pressure, solvent extraction, crystallization, recrystallization, redistribution, chromatography and the like.

Method D

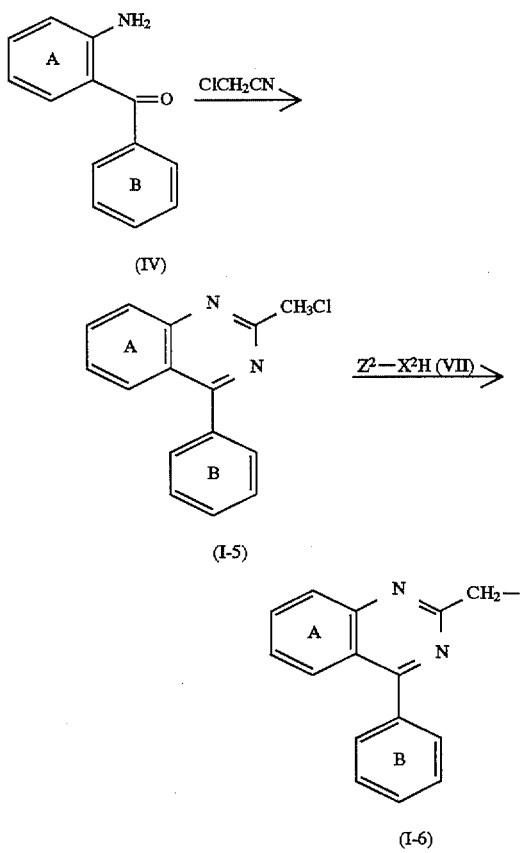

wherein each symbol is as defined above.

In this method, the compound (I-5) is prepared according to the same manner as in the method B and then reacted with the compound (VII) to give the compound (I-6). The reaction of the compound (I-5) with the compound (VII) can be carried out according to the same manner as described for the reaction of the compound (I-3) with the compound (VII) in the method C.

The quinazoline derivatives (I-5) and (I-6) thus obtained can be isolated and purified by conventional separation and purification techniques such as concentration, concentration under reduced pressure, solvent extraction, crystallization, recrystallization, redistribution, chromatography and the like.

Method E

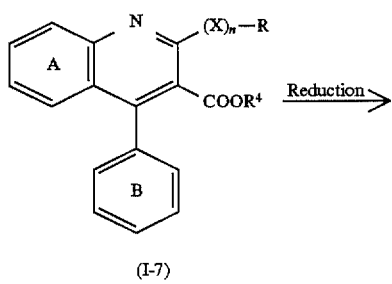

(I-7)

-continued
Method E

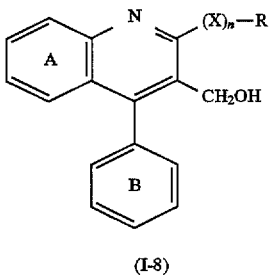

(I-8)

wherein each symbol is as defined above.

In this method, the compound (I-7) is subjected to reduction to give the alcohol (I-8). This reduction can be carried out by per se known methods, for example, with a metal hydride, metal hydride complex, diborane or substituted borane, catalytic hydrogenation or the like. That is, this reaction is carried out by treating the compound (I-7) with a reducing agent. Examples of the reducing agent include metals and metal salts such as alkaline metal borohydride (e.g., sodium borohydride, lithium borohydride, etc.), metal hydride complexes (e.g., lithium aluminium hydride, etc.), metal hydrides (e.g., sodium hydride, etc.), organic tin compounds (e.g., triphenyltin hydride, etc.), nickel compounds, zinc compounds and the like; catalytic reducing agents using a transition metal catalyst (e.g., palladium, platinum, rhodium, etc.) and hydrogen; diborane and the like.

This reaction is carried out in an organic solvent which does not have a detrimental effect on the reaction. The solvent is appropriately selected depending upon the kind of the reducing agent. Examples of the solvent include aromatic hydrocarbons (e.g., benzene, toluene, xylene, etc.), halogenated hydrocarbons (e.g., chloroform, carbon tetrachloride, dichloromethane, 1,2-dichloroethane, 1,1,2,2-tetrachloroethane, etc.), ethers (e.g., diethyl ether, tetrahydrofuran, dioxane, etc.), alcohols (e.g., methanol, ethanol, propanol, isopropanol, 2-methoxyethanol, etc.), amides (e.g., N,N-dimethylformamide, etc.) and the like. These solvents can be used alone or as a mixture thereof. The reaction temperature is normally −20° C. to 150° C., preferably about 0° C. to 100° C. The reaction time is about 1 to 24 hours.

The quinoline derivative (I-8) thus obtained can be isolated and purified by conventional separation and purification techniques such as concentration, concentration under reduced pressure, solvent extraction, crystallization, recrystallization, redistribution, chromatography and the like.

Method F

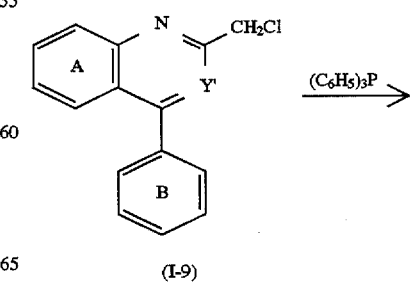

(I-9)

Method F

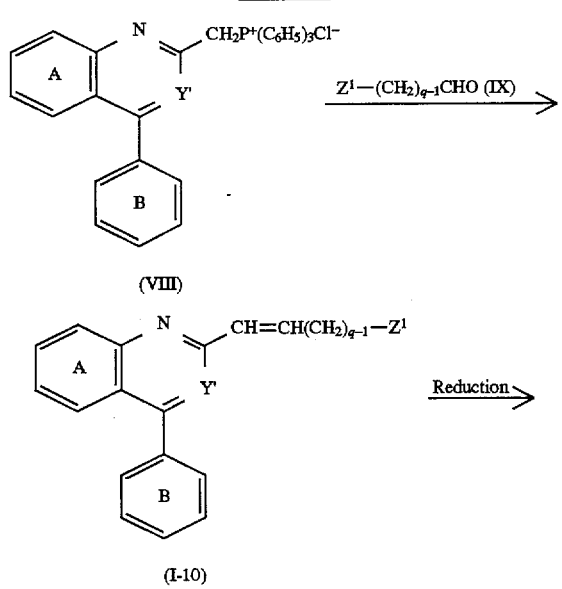

wherein q is an integer of 1 to 5, Y' is a nitrogen atom or C—COOR⁴, and the other symbols are as defined above.

In this method, firstly, a compound of the formula (I-9) is reacted with an equivalent amount of triphenylphosphine to give a phosphonium salt of the formula (VIII). This reaction is carried out in a solvent. Examples of the solvent include aromatic hydrocarbons (e.g., benzene, toluene, xylene, etc.), ethers (e.g., tetrahydrofuran, dioxane, dimethoxyethane, etc.), acetonitrile and the like. These solvents may be used alone or as a mixture thereof. The reaction temperature is 10° C. to 200° C., preferably 30° C. to 150° C. The reaction time is 0.5 to 50 hours.

Then the phosphonium salt (VIII) and aldehyde derivative (IX) are subjected to condensation reaction to give the compound (I-10). The condensation reaction of the compound (VIII) and the compound (IX) is carried out in an appropriate solvent in the presence of a base. Examples of the solvent include alcohols (e.g., methanol, ethanol, propanol, etc.), ethers (e.g., ethyl ether, dioxane, tetrahydrofuran, dimethoxyethane, etc.), aromatic hydrocarbons (e.g., benzene, toluene, xylene, etc.), dichloromethane, 1,2-dichloroethane, N,N-dimethylformamide, dimethyl sulfoxide and the like. These solvents can be used alone or as a mixture thereof. Examples of the base include alkaline metal hydrides (e.g., sodium hydride, potassium hydride, etc.), alkoxides (e.g., sodium ethoxide, sodium methoxide, potassium ethoxide, potassium tert-butoxide, etc.), organic lithium compounds (e.g., methyl lithium, butyl lithium, phenyl lithium, etc.), sodium amide and the like. The amount of the base to be used is preferably about 1 to 1.5 mol per mol of the compound (VIII). The reaction temperature is normally −50° C. to 100° C., preferably −20° C. to 50° C. The reaction time is 0.5 to 20 hours.

The compound (I-10) can be obtained as a mixture of (E)- and (Z)-isomers with respect to the newly formed double bond. By using each of the isomers after isolation or as a mixture of its isomers without isolation, the compound (I-10) is subjected to reduction to give the compound (I-11). This reduction is carried out according to conventional methods in the presence of a catalyst such as palladium catalysts (e.g., palladium carbon, palladium black, etc.), platinum catalysts (e.g., platinum dioxide, etc.), Raney nickel or the like under an atmosphere of hydrogen. Examples of the solvent include alcohols (e.g., methanol, ethanol, propanol, etc.), ethers (e.g., ethyl ether, dioxane, tetrahydrofuran, dimethoxyethane, etc.), aromatic hydrocarbons (e.g., benzene, toluene, xylene, etc.), dichloromethane, 1,2-dichloroethane, ethyl acetate, acetonitrile, acetone, 2-butanone, N,N-dimethylformamide, dimethyl sulfoxide and the like. These solvents may be used alone or as a mixture thereof. The hydrogen pressure is 1 to 150 atm, preferably 1 to 20 atm.

The quinoline or quinazoline derivatives (I-10) and (I-11) thus obtained can be isolated and purified by conventional separation and purification techniques such as concentration, concentration under reduced pressure, solvent extraction, crystallization, recrystallization, redistribution, chromatography and the like.

Method G

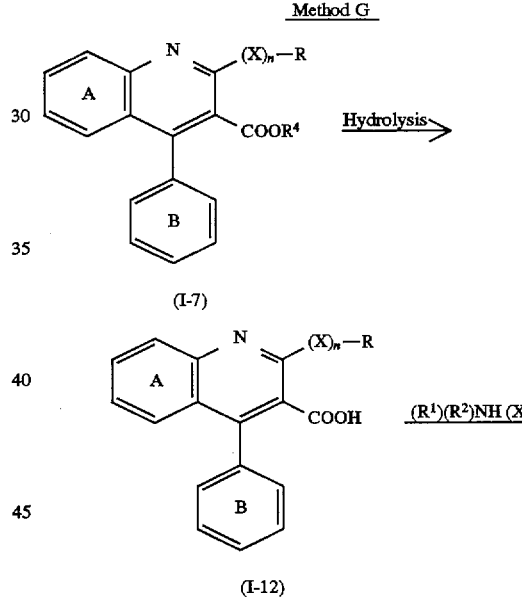

wherein each symbol is as defined above.

In this method, firstly, the quinoline ester derivative (I-7) is subjected to hydrolysis reaction to give the carboxylic acid derivative (I-12). This hydrolysis reaction can be carried out according to conventional methods in the presence of an acid or base in a solvent. As the solvent, there can be used, for example, a mixture of water and an alcohol (e.g., methanol, ethanol, etc.), ether (e.g., tetrahydrofuran, dioxane, etc.), N,N-dimethylformamide, dimethyl sulfoxide, acetone or the like. Examples of the base include potassium carbonate, sodium carbonate, sodium methoxide, sodium ethoxide, potassium tert-butoxide, sodium hydroxide, potassium hydroxide, lithium hydroxide and the like. Examples of the acid include hydrochloric acid, sulfuric acid, acetic acid, hydrobromic acid and the like. The acid or base is preferably used in an excess amount (base: 1.2 to 10 equivalents, acid: 2 to 50 equivalents) based on the compound (I-7). The temperature of the reaction is normally −20° C. to 150° C., preferably about −10° C. to 100° C.

Then, the compound (I-12) is subjected to amidation to give the compound (I-13). This amidation is carried out by the reaction of the compound (I-12) with the compound (X). The condensation reaction of the compound (I-12) with the compound (X) is carried out by conventional techniques for peptide synthesis. The techniques for peptide synthesis may be by any known methods such as methods described in M. Bodansky and M. A. Ondetti, Peptide Synthesis, Interscience, New York (1966); F. M. Finn and K. Hofmann, The Proteins, Vol. 2, edited by H. Nenrath and R. L. Hill, Academic Press Inc., New York (1976); Nobuo Izumiya et al., Basics and Experiments of Peptide Synthesis, Maruzen K. K. (1985), for example, azide method, chloride method, acid anhydride method, mixed anhydride method, DCC method, activated ester method, method using the Woodward reagent K, carbonyldiimidazole method, oxidation and reduction method, DCC/HONB method and method using DEPC (diethyl phosphorocyanidate). This condensation reaction can be carried out in a solvent. Examples of the solvent include anhydrous or hydrous dimethylformamide, dimethyl sulfoxide, pyridine, chloroform, dichloromethane, tetrahydrofuran, acetonitrile and the like. These solvents can be used alone or as a mixture thereof. The reaction temperature is normally about −20° C. to about 50° C., preferably −10° C. to 30° C. The reaction time is 1 to 100 hours, preferably 2 to 40 hours.

The quinoline derivatives (I-12) and (I-13) thus obtained can be isolated and purified by conventional separation and purification techniques such as concentration, concentration under reduced pressure, solvent extraction, crystallization, recrystallization, redistribution, chromatography and the like.

Method H

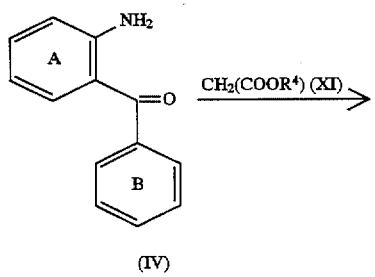

(IV)

-continued
Method H

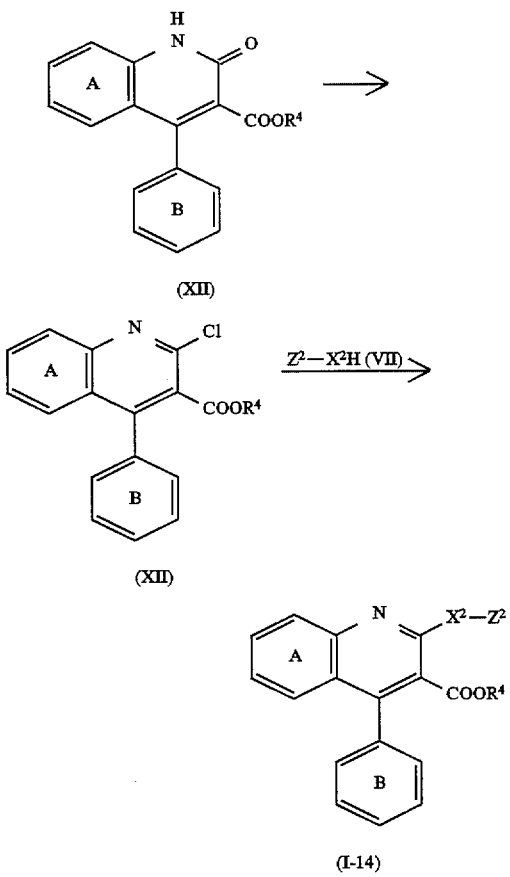

wherein each symbol is as defined above.

The reaction of the compound (IV) with malonic acid ester derivative (XI) is carried out in the presence of a base according to per se known method. Examples of the base include organic bases such as trialkylamine (e.g., trimethylamine, triethylamine, etc.), picoline, N-methylpyrrolidine, N-methylmorpholine, 1,5-diazabicyclo[4.3.0]non-5-en,1,4-diazabicyclo[2.2.2]non-5-en, 1,8-diazabicyclo[5.4.0]-7-undecene and the like. The amount of the base to be used is preferably 1 to 5 mol per mol of the compound (IV). The temperature of this reaction is normally 0° C. to 200° C., preferably about 20° C. to 150° C. Then the compound (XII) is chlorinated to give the compound (XIII). This method is carried out by known methods, for example, by heating the compound (XII) with phosphorus pentachloride, phosphorus oxychloride, thionyl chloride or oxalyl chloride in a solvent or in the absence of a solvent.

The compound (XIII) is reacted with the compound (VII) to give the quinoline derivative (I-14). The reaction of the compound (XIII) with the compound (VII) is carried out in an appropriate solvent. Examples of the solvent include aromatic hydrocarbons (e.g., benzene, toluene, xylene, etc.), ethers (e.g., dioxane, tetrahydrofuran, dimethoxyethane, etc.), alcohols (e.g., methanol, ethanol, propanol, etc.), ethyl acetate, acetonitrile, pyridine, N,N-dimethylformamide, dimethyl sulfoxide, chloroform, dichloromethane, 1,2-dichloroethane, 1,1,2,2-tetrachloroethane, acetone, 2-butanone and the like. These solvents can be used alone or as a mixture thereof. The reaction of the compound (XIII) with the compound (VII) is carried out in the presence of a base such as alkaline metal salts (e.g., sodium hydroxide, potassium hydroxide, sodium carbonate, sodium bicarbonate, etc.), amines (e.g., pyridine, triethylamine, N,N-dimethylaniline, etc.), sodium hydride, potassium hydride or the like. The amount of the base to be used is preferably about 1 to 5 mol per mol of the compound (XIII). The reaction temperature is normally −20° C. to 150° C., preferably about −10° C. to 100° C.

The quinoline derivative (I-14) thus obtained can be isolated and purified by conventional separation and purification techniques such as concentration, concentration under reduced pressure, solvent extraction, crystallization, recrystallization, redistribution, chromatography and the like.

Method I

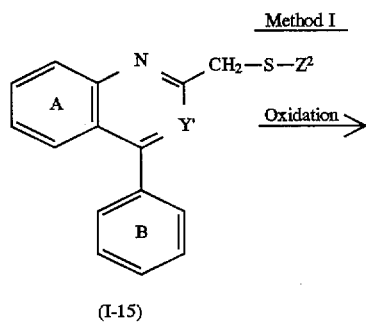

(I-15)

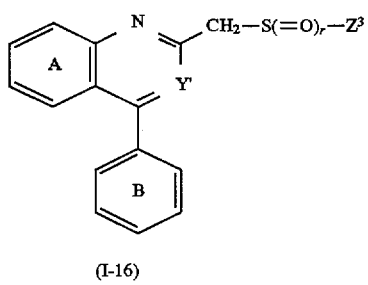

(I-16)

wherein r is 1 or 2, and the other symbols are as defined above.

In this method, the compound (I-15) obtained in Methods C or D is subjected to oxidation to give the compound (I-16). This oxidation is carried out according to conventional methods using an oxidizing agent such as m-chloroperbenzoic acid, hydrogen peroxide, peresters, sodium metaperiodate or the like. This oxidation is advantageously carried out in an organic solvent inert in the reaction conditions such as halogenated hydrocarbons (e.g., dichloromethane, chloroform, 1,2-dichloroethane, etc.), hydrocarbons (e.g., benzene, toluene, etc.), alcohols (e.g., methanol, ethanol, propanol, etc.) or the like. When the oxidizing agent is used in an equivalent amount or less based on the compound (I-15), the compound of the formula (I-16) wherein r is 1 is preferentially formed. When the oxidizing agent is used in excess of an equivalent amount, the compound of the formula (I-16) wherein r is 1 is further oxidized to give the compound of the formula (I-16) wherein r is 2. The reaction is carried out at room temperature or lower, preferably about −50° C. to 20° C. for 0.5 to 10 hours.

The quinoline derivative (I-16) thus obtained can be isolated and purified by conventional separation and purification techniques such as concentration, concentration under reduced pressure, solvent extraction, crystallization, recrystallization, redistribution, chromatography and the like.

Method J

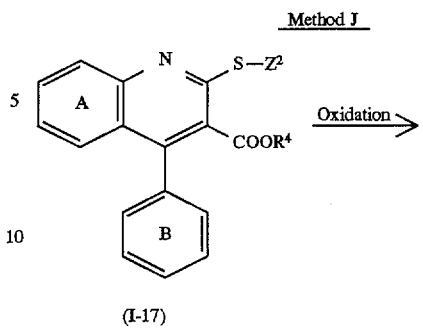

(I-17)

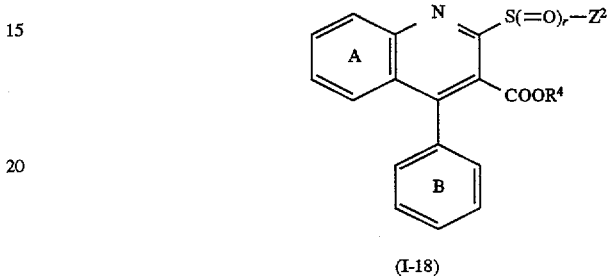

(I-18)

wherein each symbol is as defined above.

In this method, the compound (I-17) wherein $X^2$ is a sulfur atom that is obtained in Method H is subjected to oxidation to give the compound (I-18). This oxidation can be carried out according the same manner as in the method I.

The quinoline derivative (I-18) thus obtained can be isolated and purified by conventional separation and purification techniques such as concentration, concentration under reduced pressure, solvent extraction, crystallization, recrystallization, redistribution, chromatography and the like.

Method K

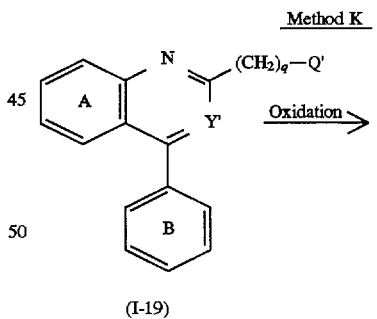

(I-19)

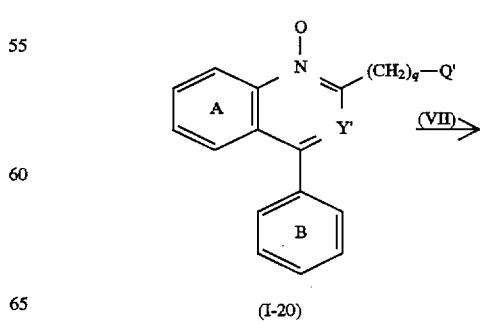

(I-20)

Method K -continued

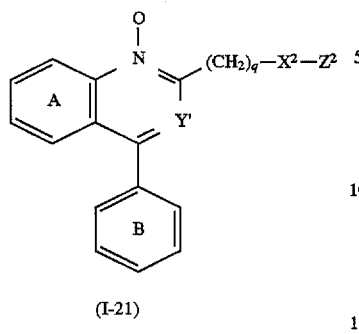

(I-21)

wherein Q' is a leaving group and the other symbols are as defined above.

Examples of the leaving group represented by Q' include halogen atoms, preferably chlorine, bromine and iodine; hydroxyl groups activated by esterification such as organic sulfonic acid residues (e.g., p-toluenesulfonyloxy, methansulfonyloxy, etc.), organic phosphoric acid residues (e.g., diphenylphosphoryloxy, dibenzylphosphoryloxy, dimethylphosphoryloxy, etc.) and the like.

In this method, firstly, the compound (I-19) is subjected to oxidation to give the compound (I-20). This oxidation is carried out according to the same manner as in the method I using an oxidizing agent such as m-chloroperbenzoic acid, hydrogen peroxide, peresters, sodium metaperiodate or the like. This oxidation is advantageously carried out in an organic solvent inert in the reaction conditions such as halogenated hydrocarbons (e.g., dichloromethane, chloroform, 1,2-dichloroethane, etc.), hydrocarbons (e.g., benzene, toluene, etc.), alcohols (e.g., methanol, ethanol, propanol, etc.) or the like. The amount of the oxidizing agent to be used is 1 to 5 mol, preferably 1 to 2 mol per mol of the compound (I-19). The reaction is carried out at 0° C. to 120° C., preferably about −10° C. to 100° C. for normally 0.5 to 10 hours.

Then, the compound (I-20) is reacted with the compound (VII) according to the same manner as that described for the conversion from the compound (I-5) to the compound (I-6) in Method D.

The quinoline or quinazoline derivatives (I-20) and (I-21) thus obtained can be isolated and purified by conventional separation and purification techniques such as concentration, concentration under reduced pressure, solvent extraction, crystallization, recrystallization, redistribution, chromatography and the like.

The compound (I-21) wherein $X^2$ is a sulfur atom that is prepared by Method K can be converted to the corresponding sulfinyl or sulfonyl compound according to the same manner as that described in Method I.

Method L

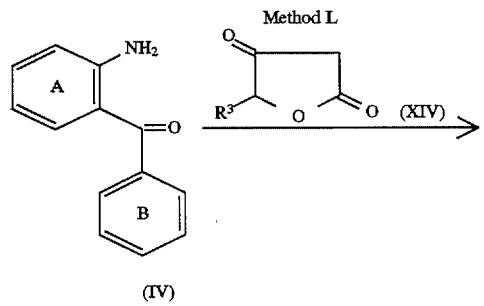

(IV)

Method L -continued

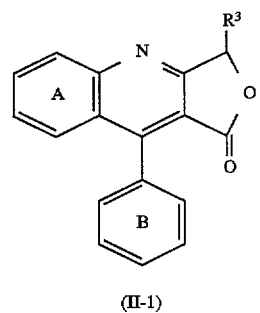

(II-1)

wherein each symbol is as defined above.

In this method, the compound (IV) is reacted with a tetronic acid derivative (XIV) to give the compound (II-1). This reaction is carried out according to the same manner as in the method A.

The quinoline derivative (II-1) thus obtained can be isolated and purified by conventional separation and purification techniques such as concentration, concentration under reduced pressure, solvent extraction, crystallization, recrystallization, redistribution, chromatography and the like.

Method M

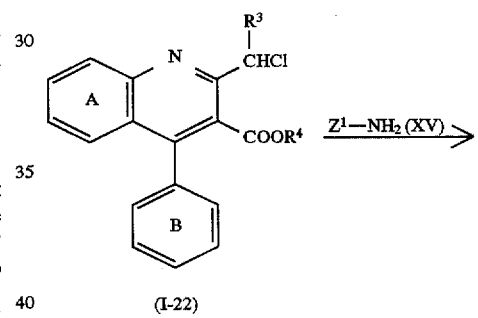

(I-22)

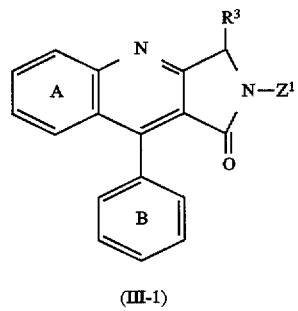

(III-1)

wherein each symbol is as defined above.

In this method, the compound (I-22) is reacted with the amine derivative (XV) to give the compound (III-1). The reaction of the compound (I-22) with the compound (XV) is carried out in an appropriate solvent. Examples of the solvent include aromatic hydrocarbons (e.g., benzene, toluene, xylene, etc.), ethers (e.g., dioxane, tetrahydrofuran, dimethoxyethane, etc.), alcohols (e.g., methanol, ethanol, propanol, etc.), ethyl acetate, acetonitrile, pyridine, N,N-dimethylformamide, dimethyl sulfoxide, chloroform, dichloromethane, 1,2-dichloroethane, 1,1,2,2-tetrachloroethane, acetone, 2-butanone and the like. These solvents can be used alone or as a mixture thereof. The reaction of the compound (I-22) with the compound (XV) is carried out in the presence of an appropriate base such as alkaline metal salts (e.g., sodium hydroxide, potassium hydroxide, potassium carbonate, sodium carbonate, sodium bicarbonate, etc.), amines (e.g., pyridine, triethylamine, N,N-dimethylaniline, etc.), sodium hydride, potassium hydride or the like. The amount of the base to be used is preferably about 1 to 5 mol per mol of the compound (I-22). The reaction temperature is normally −20° C. to 150° C., preferably about −10° C. to 100° C.

The quinoline derivative (III-1) thus obtained can be isolated and purified by conventional separation and purification techniques such as concentration, concentration under reduced pressure, solvent extraction, crystallization, recrystallization, redistribution, chromatography and the like.

Method N

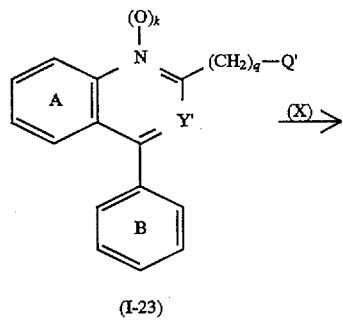

(I-23)

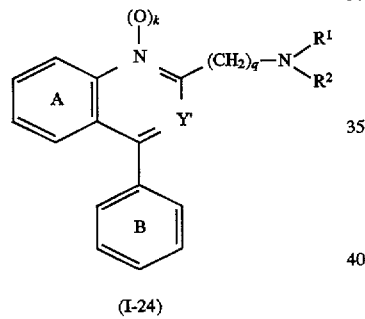

(I-24)

wherein each symbol is as defined above.

The reaction of the compound (I-23) with the compound (X) is carried out in an appropriate solvent. Examples of the solvent include aromatic hydrocarbons (e.g., benzene, toluene, xylene, etc.), ethers (e.g., dioxane, tetrahydrofuran, dimethoxyethane, etc.), alcohols (e.g., methanol, ethanol, propanol, etc.), ethyl acetate, acetonitrile, pyridine, N,N-dimethylformamide, dimethyl sulfoxide, chloroform, dichloromethane, 1,2-dichloroethane, 1,1,2,2-tetrachloroethane, acetone, 2-butanone and the like. These solvents can be used alone or as a mixture thereof. This reaction is carried out in the presence of an appropriate base such as alkaline metal salts (e.g., sodium hydroxide, potassium hydroxide, potassium carbonate, sodium carbonate, sodium bicarbonate, etc.), amines (e.g., pyridine, triethylamine, N,N-dimethylaniline, etc.), sodium hydride, potassium hydride or the like. The amount of the base to be used is preferably about 1 to 5 mol per mol of the compound (I-23). The reaction temperature is normally −20° C. to 150° C., preferably about −10° C. to 100° C.

In this reaction, the compound (X) may be used as the base by using it in an excess amount.

The quinoline or quinazoline derivative (I-24) thus obtained can be isolated and purified by conventional separation and purification techniques such as concentration, concentration under reduced pressure, solvent extraction, crystallization, recrystallization, redistribution, chromatography and the like.

The quinoline derivative obtained by Methods L and M can be converted into the corresponding quinoline 1-oxide according to the oxidation method in Method K.

Method O

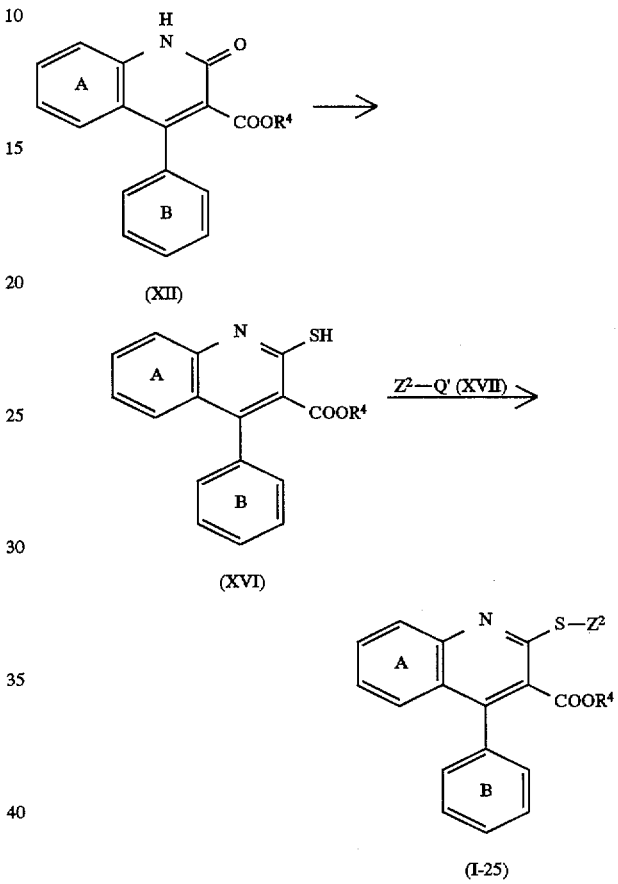

wherein each symbol is as defined above.

In this method, the compound (XII) is converted into the mercapto derivative (XVI), followed by reaction with the compound (XVII) to give the compound (I-25). The reaction from the compound (XII) to the compound (XVI) can be carried out using a thiation reagent such as phosphorous pentasulfide ($P_2S_5$) or Lawesson's reagent or the like. Examples of the solvent include aromatic hydrocarbons (e.g., benzene, toluene, xylene, etc.), ethers (e.g., dioxane, tetrahydrofuran, dimethoxyethane, etc.), pyridine, chlorobenzene, dichlorobenzene, chloroform, dichloromethane, 1,2-dichloroethane, 1,1,2,2-tetrachloroethane and the like. These solvents can be used alone or as a mixture thereof. The amount of the thiation reagent to be used is preferably about 1 to 5 mol per mol of the compound (XII). The reaction temperature is normally 0° C. to 200° C., preferably about 10° C. to 180° C. The reaction of the compound (XVI) with the compound (XVII) can be carried out according to the same manner as described for the reaction between the compounds (I-3) and (VII) in the method C.

The quinoline derivative (I-25) thus obtained can be isolated and purified by conventional separation and purification techniques such as concentration, concentration under reduced pressure, solvent extraction, crystallization, recrystallization, redistribution, chromatography and the like.

Method P

In this method, the compound (I) containing an isopropoxy group as the substituent of the ring A or ring B is treated with titanium tetrachloride, titanium trichloride, boron trichloride, tetrachlorosilane or the like to convert the isopropoxy group to a hydroxyl group, affording the corresponding compound containing a phenolic hydroxyl group as the substituent of the ring A or ring B.

This reaction is carried out in an appropriate solvent. Examples of the solvent include carbon tetrachloride, dichloromethane, chloroform, 1,2-dichloroethane, 1,1,2,2-tetrachloroethane, acetonitrile and the like. These solvents can be used alone or as mixtures thereof. The amount of the titanium tetrachloride, boron trichloride, tetrachlorosilane, etc., is 1 to 10 mol, preferably 1 to 6 mol per mol of the isopropoxy group. The reaction temperature is −50° C. to 100° C., preferably −20° C. to 80° C.

The following experiment illustrates the bone resorption inhibitory activity on the pharmaceutical composition of the present invention.

Experiment 1

Bone resorption inhibiting activity:

The bone resorption inhibiting activity was determined by the method of Raisz (J. Clin. Invest. 44, 103–116 (1965)). That is, $^{45}$Ca (radioisotope of calcium in CaCl$_2$ solution)(50 µCi) was subcutaneously injected into a Sprague-Dawley rat of 18th day of pregnancy. On the next day, the abdomen was opened and a fetal rat was taken out sterilely. The left and right humeri (radii and ulnae) were removed from the body under a dissection microscope, and connective tissues and cartilages were removed as much as possible. Thus, bone culture samples were prepared. The bone was incubated in a medium (0.6 ml) of BCJ$_b$ Medium (Fitton-Jackson modification: GIBCO Laboratories, U.S.A.) containing 2 mg/ml of bovine serum albumin at 37° C. for 24 hours in an atmosphere of 5% CO$_2$ in air. The bones were cultured for an additional 2 days in the above medium containing a final concentration of 1 µg/ml, 10 µg/ml or 10 µM of the compound. The radioactivity of $^{45}$Ca in the medium and the radioactivity of $^{45}$Ca in the bone were determined. The ratio (%) of $^{45}$Ca released from the bone into the medium was calculated according to the following equation.

$$\text{The ratio of } ^{45}\text{Ca released from the bone into the medium (\%)} = \frac{^{45}\text{Ca counts in the medium}}{^{45}\text{Ca counts in the medium} + ^{45}\text{Ca counts in the bone}} \times 100$$

The bones from the same litter were cultured for 2 days by the same manner without addition of the compound, and used as the control. The mean ± standard deviation of the values for five bones of each group was calculated. The ratio (%) of this value to the control value was calculated. The results are shown in Table 1 (In the tables hereinafter, Ex. No. indicates Example No.).

TABLE 1

| Compound (Ex. No.) | Concentration | Bone resorption inhibitory activity ($^{45}$Ca release) (% based on the control value) |
| --- | --- | --- |
| 28 | 10 µg/ml | 49 |
| 28 | 1 µg/ml | 51 |

TABLE 1-continued

| Compound (Ex. No.) | Concentration | Bone resorption inhibitory activity ($^{45}$Ca release) (% based on the control value) |
| --- | --- | --- |
| 29 | 10 µg/ml | 47 |
| 41 | 10 µg/ml | 45 |
| 41 | 1 µg/ml | 67 |
| 53 | 10 µg/ml | 59 |
| 57 | 10 µg/ml | 59 |
| 68 | 10 µg/ml | 86 |
| 78 | 10 µg/ml | 66 |
| 81 | 10 µg/ml | 55 |
| 87 | 10 µg/ml | 59 |
| 89 | 10 µg/ml | 50 |
| 89 | 1 µg/ml | 78 |
| 131 | 10 µg/ml | 79 |
| 134 | 10 µg/ml | 73 |
| 137 | 1 µg/ml | 54 |
| 139 | 10 µg/ml | 61 |
| 142 | $10^{-5}$ M | 66 |
| 148 | $10^{-5}$ M | 56 |
| 159 | 10 µg/ml | 39 |
| 166 | $10^{-5}$ M | 34 |
| 181 | $10^{-5}$ M | 45 |
| 189 | 10 µg/ml | 58 |
| 211 | $10^{-5}$ M | 28 |
| 237 | $10^{-5}$ M | 40 |
| 243 | $10^{-5}$ M | 50 |
| 263 | $10^{-5}$ M | 45 |
| 264 | $10^{-5}$ M | 51 |

As described above, the present invention provides a pharmaceutical composition comprising a quinoline or quinazoline derivative which has a direct effect on bones, exhibits excellent inhibitory activity of bone resorption and is useful as an agent for preventing or treating osteoporosis.

The following Examples and Reference examples further illustrate the present invention in detail but are not to be construed to limit the scope thereof.

EXAMPLE 1

Conc. sulfuric acid (0.3 ml) was added to a mixture of 2-amino-3',4'-dimethoxy-4,5-ethylenedioxybenzophenone (6.5 g), ethyl 4-chloroacetoacetate (3.7 g) and acetic acid (60 ml), and the mixture was stirred at 100° C. for 3 hours. The reaction mixture was concentrated under reduced pressure, and the residue was poured into water, made alkaline with 2N sodium hydroxide and extracted with chloroform. The chloroform layer was washed with water and dried over MgSO$_4$. The solvent was evaporated under reduced pressure, and the residue was subjected to column chromatography on silica gel. The fractions eluted with chloroform/ethyl acetate (=7/3, v/v) gave ethyl 2-chloromethyl-4-(3,4-dimethoxyphenyl)-6,7-ethylenedioxyquinoline-3-carboxylate (5.5 g, 60%) which was then recrystallized from acetone.

Colorless prisms.

mp. 197°–198° C.

Elemental Analysis: Calcd. for C$_{23}$H$_{22}$NO$_6$Cl: C,62.24; H,5.00; N,3.16 Found : C,61.95; H,5.15; N,3.01.

EXAMPLES 2 to 26

According to the same manner as that described in Example 1, the compounds in Tables 2 to 4 were obtained.

TABLE 2

| Ex. No. | $A^1, A^2$ | B | Yield (%) | mp (°C.) | Recrystallization Solvent |
|---|---|---|---|---|---|
| 2 | 6-Cl, H | phenyl | 61 | 105–106 | Ethanol-Water |
| 3 | 6-Cl, H | 2-Cl-phenyl | 27 | 112–114 | Methanol-Water |
| 4 | 6-Cl, H | 4-Cl-phenyl | 42 | 140–141 | Ethyl acetate-Hexane |
| 5 | 6-Cl, H | 3,4-(OCH$_3$)$_2$-phenyl | 44 | 135–136 | Ethyl acetate-Ethyl ether |
| 6 | 6-CH$_3$, H | phenyl | 42 | 78–79 | Ethyl acetate-Hexane |
| 7 | 7-CH$_3$, H | phenyl | 40 | 125–126 | Acetone-Ethyl ether |
| 8 | 6-Br, H | phenyl | 58 | 108–109 | Acetone-Isopropyl ether |
| 9 | 6-CF$_3$, H | phenyl | 80 | Note 1) Oil | — |
| 10 | 6,7-(CH$_3$)$_2$ | 4-Cl-phenyl | 70 | 170–171 | Ethyl acetate |
| 11 | 6,7-(CH$_3$)$_2$ | 2,3-(CH$_3$)$_2$-phenyl | 42 | 119–120 | Ethyl acetate-Hexane |

Note 1) NMR (δ ppm) in CDCl$_3$: 0.92 (3H, t, J=7.2Hz), 4.06 (2H, q, J=7.2Hz), 5.03 (2H, s), 7.33–7.37 (2H, m), 7.50–7.55 (3H, m), 7.90–7.98 (2H, m), 8.26 (1H, d, J=9.4Hz).

TABLE 3

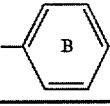

| Ex. No. | $A^1, A^2$ | B | Yield (%) | mp (°C.) | Recrystallization Solvent |
|---|---|---|---|---|---|
| 12 | 6,7-(OCH$_2$CH$_2$O) | 4-OCH$_3$-C$_6$H$_4$ | 44 | 155–156 | Acetone-Ethyl ether |
| 13 | 6,7-(CH$_3$O)$_2$ | C$_6$H$_5$ | 23 | 153–155 | Acetone-Ethyl ether |
| 14 | 6,7-(CH$_3$O)$_2$ | 4-OCH$_3$-C$_6$H$_4$ | 48 | 108–109 | Ethyl ether |
| 15 | 6,7-(CH$_3$O)$_2$ | 3-OCH$_3$-C$_6$H$_4$ | 81 | 75–76 | Isopropyl ether |
| 16 | 6,7-(CH$_3$O)$_2$ | 2-OCH$_3$-C$_6$H$_4$ | 53 | 146–147 | Ethyl acetate-Hexane |
| 17 | 6,7-(CH$_3$O)$_2$ | 4-OC$_2$H$_5$-C$_6$H$_4$ | 50 | 151–153 | Ethyl acetate-Hexane |
| 18 | 6,7-(CH$_3$O)$_2$ | 4-Cl-C$_6$H$_4$ | 53 | 160–161 | Ethyl acetate-Hexane |
| 19 | 6,7-(CH$_3$O)$_2$ | 4-CH$_3$-C$_6$H$_4$ | 35 | 126–127 | Acetone-Ethyl ether |
| 20 | 6,7-(CH$_3$O)$_2$ | 2,3-(OCH$_3$)$_2$-C$_6$H$_3$ | 44 | 181–182[1)] | Acetone-Ethyl ether |
| 21 | 6,7-(CH$_3$O)$_2$ | 2,3-(OCH$_3$)$_2$-C$_6$H$_3$ | 53 | 147–148 | Acetone-Ethyl ether |

TABLE 3-continued

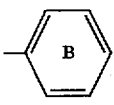

| Ex. No. | $A^1, A^2$ | B 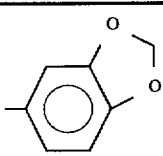 | Yield (%) | mp (°C.) | Recrystallization Solvent |
|---|---|---|---|---|---|
| 22 | 6,7-$(CH_3O)_2$ | 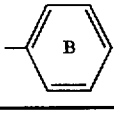 | 44 | 134–135 | Ethyl acetate-Hexane |

Note [1] Methyl 2-chloromethyl-4-(3,4-dimethoxyphenyl)-6,7-dimethoxyquinoline-3-carboxylate.

Note 1) Methyl 2-chloromethyl-4-(3,4-dimethoxyphenyl)-6,7-dimethoxyquioline-3-carboxylate.

TABLE 4

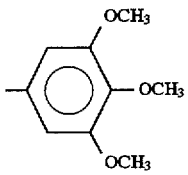

| Ex. No. | $A^1, A^2$ | B 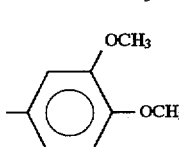 | Yield (%) | mp (°C.) | Recrystallization Solvent |
|---|---|---|---|---|---|
| 23 | 6,7-$(CH_3O)_2$ | 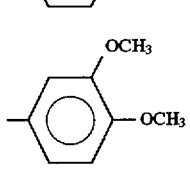 — 3×$OCH_3$ | 64 | 211–212 | Chloroform-Acetone |
| 24 | 6,7-$(C_2H_5O)_2$ | 2×$OCH_3$ | 68 | 124–125 | Ethyl acetate-Hexane |
| 25 | H, H | 2×$OCH_3$ | 50 | 82–83 | Ethyl acetate-Hexane |

TABLE 4-continued

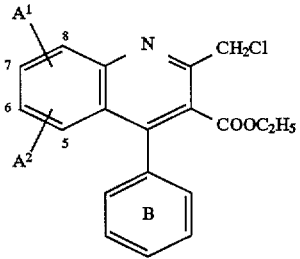

| Ex. No. | $A^1, A^2$ | B 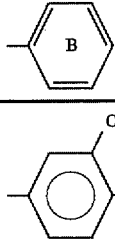 | Yield (%) | mp (°C.) | Recrystallization Solvent |
|---|---|---|---|---|---|
| 26 | 6-$CH_3$ | 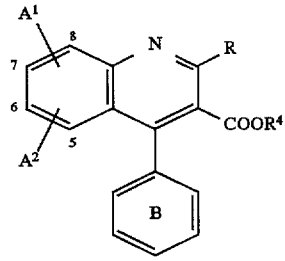 | 80 | 125–126 | Ethanol |

EXAMPLE 27

Conc. sulfuric acid was added to a mixture of 2-amino-4,5,3',4'-tetramethoxybenzophenone, ethyl acetoacetate and acetic acid. The mixture was treated according to the same manner as that described in Example 1 to give ethyl 6,7-dimethoxy-4-(3,4-dimethoxyphenyl)-2-methylquinoline-3-carboxylate (83%) which was then recrystallized from ethanol.

Colorless prisms.

mp. 147°–148° C.

EXAMPLES 28 to 49

According to the same manner as that described in Example 27, the compounds in Tables 5 to 9 were obtained.

TABLE 5

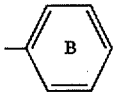

| Ex. No. | $A^1, A^2$ | B 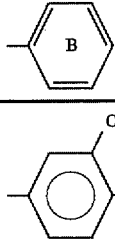 | R | $R^4$ | Yield (%) | mp (°C.) | Recrystallization Solvent |
|---|---|---|---|---|---|---|---|
| 28 | 6,7-$(CH_3O)_2$ | 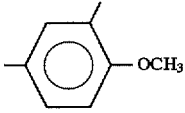 | $C_2H_5$ | $CH_3$ | 90 | 150–151 | Ethanol |
| 29 | 6,7-$(CH_3O)_2$ | 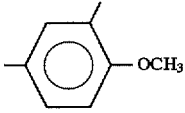 | $CH(CH_3)_2$ | $CH_3$ | 40 | 160–161 | Ethanol |

TABLE 5-continued

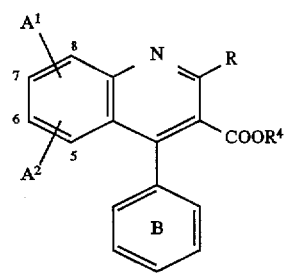

| Ex. No. | $A^1, A^2$ | B | R | $R^4$ | Yield (%) | mp (°C.) | Recrystallization Solvent |
|---|---|---|---|---|---|---|---|
| 30 | 6,7-$(CH_3O)_2$ | 3,4-di-$OCH_3$-phenyl | $CH_3$ | $C(CH_3)_3$ | 32 | 139–141 | Isopropyl ether-Hexane |
| 31 | 6,7-$(CH_3O)_2$ | 4-$OCH_3$-phenyl | $C_2H_5$ | $CH_3$ | 76 | 110–111 | Ethyl ether-Isopropyl ether |
| 32 | 6,7-$(CH_3O)_2$ | 4-$OCH_3$-phenyl | $CH_3$ | $CH_3$ | 87 | 136–137 | Ethanol |

TABLE 6

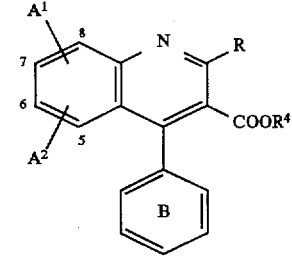

| Ex. No. | $A^1, A^2$ | B | R | $R^4$ | Yield (%) | mp (°C.) | Recrystallization Solvent |
|---|---|---|---|---|---|---|---|
| 33 | 6,7-$(CH_3O)_2$ | 3-$OCH_3$-phenyl | $CH_3$ | $CH_3$ | 77 | 129–130 | Ethanol |
| 34 | 6,7-$(CH_3O)_2$ | 3,5-di-$OCH_3$-4-OH-phenyl | $CH_3$ | $CH_3$ | 78 | 109–111 | Ethyl ether |

TABLE 6-continued
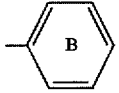
| Ex. No. | $A^1, A^2$ | B 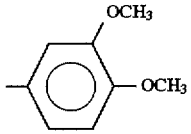 | R | $R^4$ | Yield (%) | mp (°C.) | Recrystallization Solvent |
|---|---|---|---|---|---|---|---|
| 35 | 6,7-(OCH$_2$O) | 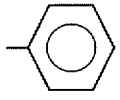 | CH$_3$ | CH$_3$ | 45 | 155–156 | Ethanol |
| 36 | 6,7-(CH$_3$O)$_2$ | 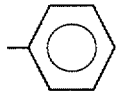 | C$_2$H$_5$ | CH$_3$ | 52 | 120–121 | Isopropyl ether |
| 37 | 6,7-(CH$_3$O)$_2$ | 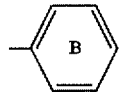 | CH$_3$ | CH$_3$ | 75 | 154–155 | Isopropyl ether |
TABLE 7
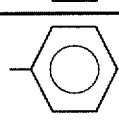
| Ex. No. | $A^1, A^2$ | B 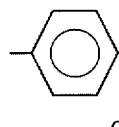 | R | $R^4$ | Yield (%) | mp (°C.) | Recrystallization Solvent |
|---|---|---|---|---|---|---|---|
| 38 | 6,7-(CH$_3$O)$_2$ | 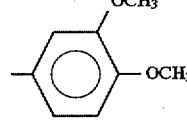 | CH$_3$ | C$_2$H$_5$ | 63 | 197–199 | Ethanol |
| 39 | 6-CH$_3$O | | C$_2$H$_5$ | CH$_3$ | 57 | 82–84 | Ethyl ether-Hexane |
| 40 | 6-Cl | | C$_2$H$_5$ | CH$_3$ | 57 | 118–120 | Ethyl ether-Hexane |

TABLE 7-continued

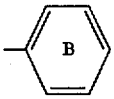

| Ex. No. | $A^1, A^2$ | B | R | $R^4$ | Yield (%) | mp (°C.) | Recrystallization Solvent |
|---|---|---|---|---|---|---|---|
| 41 | 6-Cl | 3,4-(OCH$_3$)$_2$ | CH$_3$ | CH$_3$ | 70 | 126–128 | Ethyl ether |
| 42 | 6,7-(CH$_3$O)$_2$ | 2,4-(CH$_3$)$_2$ | C$_2$H$_5$ | CH$_3$ | 45 | 102–103 | Ethyl ether-Hexane |

TABLE 8

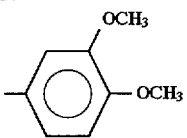

| Ex. No. | $A^1, A^2$ | B | R | $R^4$ | Yield (%) | mp (°C.) | Recrystallization Solvent |
|---|---|---|---|---|---|---|---|
| 43 | 6-CH$_3$ | 3,4-(OCH$_3$)$_2$ | C$_2$H$_5$ | CH$_3$ | 63 | 114–115 | Ethyl ether-Hexane |
| 44 | 6,7-(CH$_3$O)$_2$ | 4-Cl | C$_2$H$_5$ | CH$_3$ | 73 | 136–137 | Ethyl ether-Hexane |
| 45 | 6-Cl | 2,4-(CH$_3$)$_2$ | CH$_3$ | CH$_3$ | 88 | 121–122 | Ethyl ether-Hexane |
| 46 | 6,7-(CH$_3$)$_2$ | 4-CH$_3$ | C$_2$H$_5$ | CH$_3$ | 68 | 127–128 | Isopropyl ether |

TABLE 8-continued

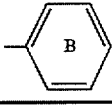

| Ex. No. | $A^1, A^2$ | B | R | $R^4$ | Yield (%) | mp (°C.) | Recrystallization Solvent |
|---|---|---|---|---|---|---|---|
| 47 | 6-$CH_3$ | 4-$CH_3$-$C_6H_4$ | $C_2H_5$ | $CH_3$ | 59 | 81–82 | Ethyl ether |

TABLE 9

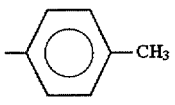

| Ex. No. | $A^1, A^2$ | B | R | $R^4$ | Yield (%) | mp (°C.) | Recrystallization Solvent |
|---|---|---|---|---|---|---|---|
| 48 | 6,7-$(CH_3O)_2$ | 2,6-$(OCH_3)_2$-$C_6H_3$ | $CH_3$ | $C_3H_7$ | 79 | 153–155 | Ethyl acetate-Isopropyl ether |
| 49 | 6,7-$(CH_3O)_2$ | 2,6-$(OCH_3)_2$-$C_6H_3$ | $CH_3$ | $C_4H_9$ | 53 | 119–120 | Ethyl acetate-Hexane |

EXAMPLE 50

One drop of conc. sulfuric acid was added to a mixture of 2-amino-4,5,3',5'-tetramethoxy-4'-hydroxybenzophenone (0.333 g), tetronic acid (tetrahydrofuran-2,4-dione) (0.11 g) and acetic acid (10 ml), and the mixture was stirred at 100° C. for 1.5 hours. The reaction mixture was concentrated under reduced pressure. The residual oil was poured into water, neutralized with an aqueous saturated sodium bicarbonate solution and extracted with chloroform. The chloroform layer was washed with water and dried over magnesium sulfate. Evaporation of the solvent gave 6,7-dimethoxy-9-(4-hydroxy-3,5-dimethoxyphenyl)furo[3,4-b]quinoline -1(3H)-one (0.349 g, 88%) which was then recrystallized from methanol. Pale yellow needles. mp. 247°–248° C.

EXAMPLES 51 to 55

According to the same manner as that described in Example 50, the compounds in Table 10 were obtained.

TABLE 10

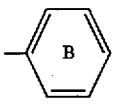

| Ex. No. | A¹ | A² | B | Yield (%) | mp (°C.) | Recrystallization Solvent |
|---|---|---|---|---|---|---|
| 51 | CH₃O | CH₃O | 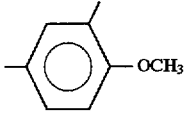 (OCH₃, OCH₃) | 90 | 241–242 | Methanol-Chloroform |
| 52 | OCH₂O | | 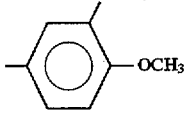 (OCH₃, OCH₃) | 84 | 252–253 | Ethanol |
| 53 | CH₃O | CH₃O |  | 38 | 210–211 | Ethanol |
| 54 | H | Cl | 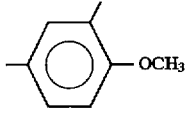 (OCH₃, OCH₃) | 89 | 210–212 | Acetone |
| 55 | H | Cl | 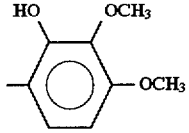 (HO, OCH₃, OCH₃) | 95 | 254–255 | Methanol |

EXAMPLE 56

A mixture of ethyl 2-chloromethyl-6,7-dimethoxy-4-(3,4-dimethoxyphenyl)quinoline-3-carboxylate (3.0 g), m-chloroperbenzoic acid (85%, 2.3 g) and methanol (40 ml) was stirred for 2 hours under reflux. The solvent in the reaction mixture was evaporated under reduced pressure, and the residue was poured into chloroform. The chloroform layer was washed with water and dried over magnesium sulfate. The solvent was evaporated under reduced pressure. The residue was subjected to column chromatography on silica gel. The fractions eluted with chloroform/ethyl acetate (=6/4, v/v) gave ethyl 2-chloromethyl-6,7-dimethoxy-4-(3,4-dimethoxyphenyl)quinoline-3-carboxylate 1-oxide (2.0 g, 65%) which was then recrystallized from acetone-isopropyl ether.

Colorless prisms.
mp. 193°–194° C.

Elemental Analysis: Calcd. for $C_{23}H_{24}NO_7Cl$: C,59.81; H,5.24; N,3.03 Found: C,59.69; H,5.32; N,3.05.

EXAMPLE 57

Powdered aluminium chloride (6.7 g) was added to a mixture of 2-amino-4,5,3',4'-tetramethoxybenzophenone (8.0 g) and chloroacetonitrile (25 ml), and the mixture was stirred at 100° C. for 2 hours. The reaction mixture was poured into water, and the resulting mixture was extracted with chloroform. The chloroform layer was washed with water and dried over magnesium sulfate. The solvent was evaporated. The residue was subjected to column chromatography on silica gel. The fractions eluted with chloroform/ethyl acetate (=10/1, v/v) gave 2-chloromethyl-6,7-dimethoxy-4-(3,4-dimethoxyphenyl)quinazoline (4.9 g, 52%) which was then recrystallized from acetone.

Colorless prisms. mp. 183°–184° C.

EXAMPLE 58

A mixture of sodium iodide (1.68 g) and methyl ethyl ketone (15 ml) was stirred at 80° C. for 1 hour, and then ethyl 2-chloromethyl-6,7-dimethoxy-4-(3,4-dimethoxyphenyl) quinoline-3-carboxylate (2.0 g) was added thereto, and the resulting mixture was stirred at the same temperature for 12 hours. The insoluble solid was filtered off, and the filtrate was concentrated under reduced pressure. The residue was poured into water and extracted with ethyl acetate. The ethyl acetate layer was washed with water and dried over magnesium sulfate, and the solvent was evaporated. The residual oil was subjected to column chromatography on silica gel. The fractions eluted with chloroform/ethyl acetate (1/1,v/v) gave ethyl 6,7-dimethoxy-4-(3,4-dimethoxyphenyl)-2-iodomethylquinoline-3-carboxylate (1.4 g, 58%) which was then recrystallized from ethyl acetate-hexane.

Colorless prisms.

mp. 170°–171° C.

Elemental Analysis: Calcd. for $C_{23}H_{24}NO_6I$: C,51.41; H,4.50; N,2.61 Found: C,51.25; H,4.53; N,2.58.

EXAMPLE 59

A mixture of ethyl 2-chloromethyl-6,7-dimethoxy-4-(3,4-dimethoxyphenyl)quinoline-3-carboxylate (3.0 g), 1-ethyl-2-mercaptoimidazole (1.0 g), potassium carbonate (1.1 g) and N,N-dimethylformamide (30 ml) was stirred at room temperature for 3 hours. The reaction mixture was poured into water and extracted with ethyl acetate. The ethyl acetate layer was washed with water and dried over magnesium sulfate, and the solvent was evaporated under reduced pressure. The residue was subjected to column chromatography on silica gel. The fractions eluted with chloroform/ethyl acetate (=3/2, v/v) gave ethyl 2-[(1-ethylimidazol-2-yl)thiomethyl]-6,7-dimethoxy-4-(3,4-dimethoxyphenyl)quinoline-3-carboxylate (2.8 g, 78%) which was then recrystallized from ethyl acetate-hexane.

Colorless prisms.

mp. 157°–158° C.

Elemental Analysis: Calcd. for $C_{23}H_{31}N_3O_6S$: C,62.55; H,5.81; N,7.82 Found: C,62.55; H,5.84; N,7.79.

EXAMPLE 60 m-Chloroperbenzoic acid (85%, 830 mg) was added in small portions under ice-cooling to a solution of ethyl 6,7-dimethoxy-4-(3,4-dimethoxyphenyl)-2-[(1-methylimidazol-2-yl)thiomethyl]quinoline-3-carboxylate (3.0 g) in dichloromethane (75 ml). The reaction mixture was stirred at room temperature for 2.5 hours, washed successively with 5% aqueous $NaHSO_3$ solution, saturated aqueous sodium bicarbonate solution and water, and dried over magnesium sulfate. The solvent was evaporated under reduced pressure. The residue was subjected to column chromatography on silica gel. The fractions eluted with ethyl acetate/methanol (10/1, v/v) gave ethyl 6,7-dimethoxy-4-(3,4-dimethoxyphenyl)-2-[(1-methylimidazol-2-yl)sulfinylmethyl]quinoline-3-carboxylate (1.8 g, 58%) which was then recrystallized from acetone-ethyl ether.

Colorless prisms.

mp. 193°–194° C.

Elemental Analysis: Calcd. for $C_{27}H_{29}N_3O_7S$: C,60.10; H,5.42; N,7.79 Found: C,59.80; H,5.60; N,7.51.

EXAMPLE 61

According to the same manner as that described in Example 60, ethyl 2-[(2-benzimidazolyl)sulfinylmethyl]-6,7-dimethoxy- 4-(3,4-dimethoxyphenyl)quinoline-3-carboxylate was obtained and then recrystallized from acetone.

Colorless prisms.

mp. 160°–161° C.

Elemental Analysis: Calcd. for $C_{30}H_{29}N_3O_7S$: C,62.60; H,5.08; N,7.30 Found: C,62.21; H,5.10; N,7.09.

EXAMPLE 62 m-Chloroperbenzoic acid (85%, 2.5 g) was added in small portions under ice-cooling to a solution of ethyl 6,7-dimethoxy-4-(3,4-dimethoxyphenyl)-2-[(1-methylimidazol-2-yl)thiomethyl]quinoline-3-carboxylate (2.5 g) in dichloromethane (60 ml). The reaction mixture was stirred at room temperature for 4 hours, washed successively with 5% aqueous $NaHSO_3$ solution, saturated aqueous sodium bicarbonate solution and water, and dried over magnesium sulfate. The solvent was evaporated under reduced pressure. The residue was subjected to column chromatography on silica gel. The fractions eluted with ethyl acetate/methanol (10/1, v/v) gave ethyl 6,7-dimethoxy-4-(3,4-dimethoxyphenyl)-2-[(1-methylimidazol-2-yl)sulfonylmethyl]quinoline-3-carboxylate (1.5 g, 58%) which was then recrystallized from acetone-ethyl ether.

Colorless prisms.

mp. 183°–184° C.

Elemental Analysis: Calcd. for $C_{27}H_{29}N_3O_8S$: C,58.37; H,5.26; N,7.56 Found: C,58.46; H,5.24; N,7.20.

EXAMPLE 63

According to the same manner as that described in Example 62, ethyl 2-[(2-benzimidazolyl)sulfonylmethyl]-6,7-dimethoxy-4-(3,4-dimethoxyphenyl)quinoline-3-carboxylate was obtained and then recrystallized from acetone-isopropyl ether.

Colorless prisms.

mp. 181°–182° C.

Elemental Analysis: Calcd. for $C_{30}H_{29}N_3O_8S$: C,60.90; H,4.94; N,7.10 Found: C,60.76; H,4.86; N,7.09.

EXAMPLE 64

A solution of hydrogen chloride in ethanol (27%, 1.3 g) was added dropwise to a solution of ethyl 6,7-dimethoxy-4-(3,4-dimethoxyphenyl)-2-[(1-methylimidazol-2-yl)thiomethyl]-quinoline-3-carboxylate (4.9 g) in ethanol (100 ml) at room temperature. About two thirds of the solvent was evaporated under reduced pressure, ethyl ether was added to the residue, and the resulting crystals were collected by filtration. The crystals were recrystallized from isopropanol to give ethyl 6,7-dimethoxy-4-(3,4-dimethoxyphenyl)-2-[(1-methylimidazol-2-yl)thiomethyl]quinoline-3-carboxylate hydrochloride monohydrate (3.0 g, 55%).

Colorless prisms.

mp. 133°–134° C.

Elemental Analysis: Calcd. for $C_{27}H_{29}N_3O_6S.HCl.H_2O$: C,56.10; H,5.58; N,7.27 Found: C,55.84; H,5.72; N,7.16.

EXAMPLE 65

According to the same manner as that described in Example 59, ethyl 6,7-dimethoxy-4-(2-methoxyphenyl)-2-[(1-methylimidazol-2-yl)thiomethyl]quinoline-3-carboxylate (89%) was obtained as an oil.

NMR (δ ppm) in $CDCl_3$: 0.90 (3H,t,J=7 Hz), 3.34 (3H,s), 3.70 (3H,s), 3.74 (3H,s), 3.98 (2H,q,J=7 Hz), 4.03 (3H,s), 4.64 (2H,s), 6.66 (1H,s), 6.86 (1H,s), 7.01–7.16 (4H,m), 7.34 (1H,s), 7.45 (1H,double t,J=8 and 2 Hz).

This oil was dissolved in ethanol (15 ml), and a solution of hydrogen chloride in ethanol (23%, 1.2 g) was added. Evaporation of the solvent under reduced pressure gave ethyl 6,7-dimethoxy-4-(2-methoxyphenyl)-2-[(1-methylimidazol-2-yl)thiomethyl]quinoline-3-carboxylate hydrochloride (2.0 g) which was then recrystallized from ethanol-ethyl ether.

Pale yellow prisms.

mp. 180°–181° C.

Elemental Analysis: Calcd. for $C_{26}H_{27}N_3O_5S \cdot HCl \cdot 1/2H_2O$: C,57.93; H,5.42; N,7.80 Found: C,58.05; H,5.32; N,7.72.

EXAMPLE 66

According to the same manner as that described in Example 59, ethyl 6,7-dimethyl-4-(3,4-dimethylphenyl)-2-[(1-methylimidazol-2-yl)thiomethyl]quinoline-3-carboxylate (97%) was obtained as an oil.

NMR (δ ppm) in $CDCl_3$: 0.93 (3H,t,J=7 Hz), 2.31 (3H,s), 2.32 (3H,s), 2.35 (3H,s), 2.44 (3H,s), 3.42 (3H,s), 4.03 (2H,q,J=7 Hz), 4.61 (2H,s), 6.88 (1H,d,J=1 Hz), 7.03–7.10 (3H,m), 7.23 (1H,d,J=8 Hz), 7.35 (1H,s), 7.78 (1H,s).

This oil was dissolved in ethanol (10 ml), and a solution of hydrogen chloride in ethanol (23%, 0.584 g) was added. Evaporation of the solvent under reduced pressure gave ethyl 6,7-dimethyl-4-(3,4-dimethylphenyl)-2-[(1-methylimidazol-2-yl)thiomethyl]quinoline-3-carboxylate hydrochloride (1.1 g) which was then recrystallized from ethanol-ethyl ether.

Pale yellow prisms.

mp. 133°–134° C.

Elemental Analysis: Calcd. for $C_{27}H_{29}N_3O_2S \cdot HCl \cdot 3/2H_2O$: C,62.00; H,6.36; N,8.03 Found: C,62.31; H,6.01; N,7.98.

EXAMPLE 67

According to the same manner as that described in Example 59, ethyl 6,7-dimethoxy-4-(3,4-dimethoxyphenyl)-2-[(1-methylimidazol-2-yl)thiomethyl]quinoline-3-carboxylate 1-oxide (69%) was obtained and then recrystallized from ethyl acetatehexane.

Colorless prisms.

mp. 171°–172° C.

Elemental Analysis: Calcd. for $C_{27}H_{29}N_3O_7S$: C,60.10; H,5.42; N,7.79 Found: C,60.29; H,5.53; N,7.49.

EXAMPLES 68 to 130

According to the same manner as that described in Example 59, the compounds in Tables 11 to 20 were obtained.

TABLE 11

| Ex. No. | A¹, A² | B | Z² | Yield (%) | mp (°C.) | Recrystallization Solvent |
|---|---|---|---|---|---|---|
| 68 | 6-Cl, H | 4-Cl-phenyl | 1-methylimidazol-2-yl | 64 | 117–118 | Ethyl acetate-Hexane |
| 69 | 6-Cl, H | 2-Cl-phenyl | 1-methylimidazol-2-yl | 48 | 137–138 | Acetone-Ethyl ether |
| 70 | 6-Cl, H | 3,4-dimethoxyphenyl | 1-methylimidazol-2-yl | 71 | 120–121 | Acetone-Isopropyl ether |
| 71 | 6-Cl, H | 3,4-dimethoxyphenyl | 1H-benzimidazol-2-yl | 55 | 190–191 | Acetone-Isopropyl ether |

TABLE 11-continued

[Structure: quinoline with A¹ at position 8, A² at position 5, positions 6,7 on benzene ring; N at position 1; CH₂—S—Z² at position 2; COOC₂H₅ at position 3; B (phenyl) at position 4]

| Ex. No. | A¹, A² | B | Z² | Yield (%) | mp (°C.) | Recrystallization Solvent |
|---|---|---|---|---|---|---|
| 72 | 6-CH₃, H | phenyl | 1-methyl-2-imidazolyl (with =C-CH₃ linkage) | 58 | 132–133 | Ethyl acetate-Hexane |

TABLE 12

[Same quinoline structure]

| Ex. No. | A¹, A² | B | Z² | Yield (%) | mp (°C.) | Recrystallization Solvent |
|---|---|---|---|---|---|---|
| 73 | 7-CH₃, H | phenyl | 1-methyl-2-imidazolyl | 58 | 98–99 | Ethyl acetate-Hexane |
| 74 | 6-Br, H | phenyl | 1-methyl-2-imidazolyl | 69 | 129–130 | Ethyl acetate-Hexane |
| 75 | 6-CF₃, H | phenyl | 1-methyl-2-imidazolyl | 54 | 108–109 | Ethyl acetate-Hexane |
| 76 | 6,7-(CH₃)₂ | 4-Cl-phenyl | 1-methyl-2-imidazolyl | 64 | 114–115 | Ethyl acetate-Hexane |

TABLE 12-continued
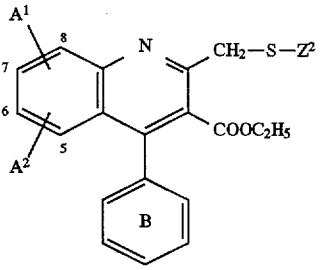
| Ex. No. | $A^1$, $A^2$ | B 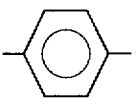 | $Z^2$ | Yield (%) | mp (°C.) | Recrystallization Solvent |
|---|---|---|---|---|---|---|
| 77 | 6,7-($OCH_2CH_2O$) | 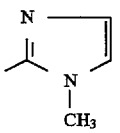 | 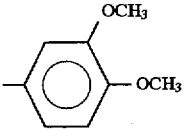 | 69 | 180–181 | Acetone-Ethyl ether |
| 78 | 6,7-($OCH_2CH_2O$) | 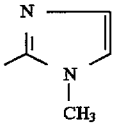 | 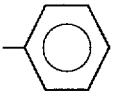 | 60 | 120–121 | Acetone |
| 79 | 6,7-($CH_3O)_2$ | 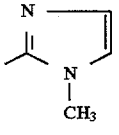 | 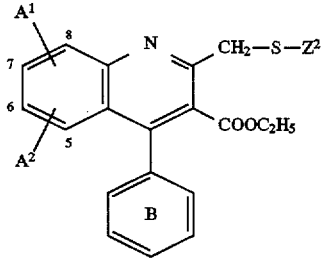 | 60 | 111–102 | Acetone-Ethyl ether |
TABLE 13
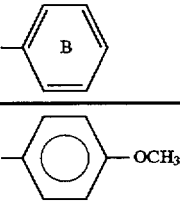
| Ex. No. | $A^1$, $A^2$ | B 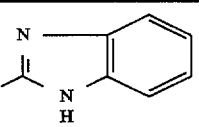 | $Z^2$ | Yield (%) | mp (°C.) | Recrystallization Solvent |
|---|---|---|---|---|---|---|
| 80 | 6,7-($CH_3O)_2$ | 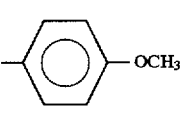 | 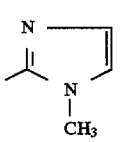 | 85 | 105–107 | Ethyl ether |
| 81 | 6,7-($CH_3O)_2$ | 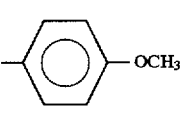 | 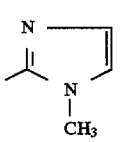 | 72 | 123–124 | Ethyl ether |

TABLE 13-continued

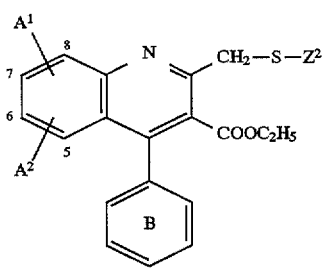

| Ex. No. | $A^1, A^2$ | B | $Z^2$ | Yield (%) | mp (°C.) | Recrystallization Solvent |
|---|---|---|---|---|---|---|
| 82 | 6,7-$(CH_3O)_2$ | 3-$OCH_3$-phenyl | 2-(1-methylimidazolyl) | 57 | 99–100 | Ethyl acetate-Hexane |
| 83 | 6,7-$(CH_3O)_2$ | 3-$OCH_3$-phenyl | 2-benzimidazolyl (NH) | 48 | 102–103 | Isopropyl ether |
| 84 | 6,7-$(CH_3O)_2$ | 4-$OC_2H_5$-phenyl | 2-(1-methylimidazolyl) | 80 | 117–118 | Ethyl acetate-Hexane |
| 85 | 6,7-$(CH_3O)_2$ | 4-Cl-phenyl | 2-(1-methylimidazolyl) | 74 | 132–133 | Ethyl acetate-Hexane |
| 86 | 6,7-$(CH_3O)_2$ | 4-$CH_3$-phenyl | 2-(1-methylimidazolyl) | 46 | 134–135 | Acetone-Ethyl ether |

TABLE 14

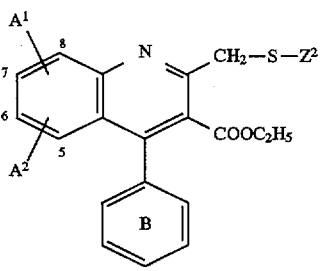

| Ex. No. | $A^1, A^2$ | B | $Z^2$ | Yield (%) | mp (°C.) | Recrystallization Solvent |
|---|---|---|---|---|---|---|
| 87 | 6,7-$(CH_3O)_2$ | 3,4-(OCH$_3$)$_2$-phenyl | thiazolyl-methyl | 81 | 145–146 | Ethyl acetate-Hexane |
| 88 | 6,7-$(CH_3O)_2$ | 3,4-(OCH$_3$)$_2$-phenyl | 1-methyl-imidazolyl | 77 | 147–148 | Acetone-Isopropyl ether |
| 89 | 6,7-$(CH_3O)_2$ | 3,4-(OCH$_3$)$_2$-phenyl | 1-methyl-imidazolyl | 84 | 149–150 | Acetone-Ethyl ether |
| 90 | 6,7-$(CH_3O)_2$ | 3,4-(OCH$_3$)$_2$-phenyl | 1-methyl-triazolyl | 76 | 176–177 | Acetone-Ethyl ether |
| 91 | 6,7-$(CH_3O)_2$ | 3,4-(OCH$_3$)$_2$-phenyl | imidazolyl-NH | 65 | 111–112 | Acetone-Ethyl ether |
| 92 | 6,7-$(CH_3O)_2$ | 3,4-(OCH$_3$)$_2$-phenyl | 2-pyridyl | 88 | 162–163 | Acetone |
| 93 | 6,7-$(CH_3O)_2$ | 3,4-(OCH$_3$)$_2$-phenyl | 4-pyridyl | 77 | 185–186 | Acetone |

TABLE 15

[Structure: quinoline with A¹ at position 8, A² at position 5, positions 6,7 on benzene ring; CH₂—S—Z² at position 2; COOC₂H₅ at position 3; phenyl group B at position 4]

| Ex. No. | A¹, A² | B | Z² | Yield (%) | mp (°C.) | Recrystallization Solvent |
|---|---|---|---|---|---|---|
| 94 | 6,7-(CH₃O)₂ | 3,4-(OCH₃)₂-phenyl | CH₂-(4-Cl-phenyl) | 90 | 165–166 | Ethyl ether |
| 95 | 6,7-(CH₃O)₂ | 3,4-(OCH₃)₂-phenyl | 4-Cl-phenyl | 83 | 152–153 | Ethyl ether |
| 96 | 6,7-(CH₃O)₂ | 3,4-(OCH₃)₂-phenyl | pyrimidin-2-yl | 86 | 174–176 | Ethyl ether |
| 97 | 6,7-(CH₃O)₂ | 3,4-(OCH₃)₂-phenyl | 3-methyl-1,2,4-thiadiazol-5-yl | 80 | 184–185 | Acetone |
| 98 | 6,7-(CH₃O)₂ | 3,4-(OCH₃)₂-phenyl | 4-oxo-3H-pyrimidin-2-yl | 72 | 186–187 | Ethyl acetate-Hexane |
| 99 | 6,7-(CH₃O)₂ | 3,4-(OCH₃)₂-phenyl | 3-hydroxypyridin-2-yl | 83 | 219–220 | Ethyl acetate-Hexane |
| 100 | 6,7-(CH₃O)₂ | 3,4-(OCH₃)₂-phenyl | 4,5-dihydrothiazol-2-yl | 63 | 190–191 | Ethyl acetate-Hexane |

TABLE 16

[Structure: quinoline core with A¹ at position 8, A² at position 5, positions 6,7 on benzene ring; substituent CH₂—S—Z² at position 2; COOC₂H₅ at position 3; phenyl group B at position 4]

| Ex. No. | A¹, A² | B | Z² | Yield (%) | mp (°C.) | Recrystallization Solvent |
|---|---|---|---|---|---|---|
| 101 | 6,7-(CH₃O)₂ | 3,4-(OCH₃)₂-phenyl | 2-(1-propyl)pyrrol-2-yl (N-CH₂CH₂CH₃) | 77 | 132–133 | Ethyl acetate-Hexane |
| 102 | 6,7-(CH₃O)₂ | 3,4-(OCH₃)₂-phenyl | 2-(1-isopropyl)pyrrol-2-yl (N-CH(CH₃)₂) | 67 | 122–123 | Ethyl acetate-Hexane |
| 103 | 6,7-(CH₃O)₂ | 3,4-(OCH₃)₂-phenyl | 2-(1-benzyl)pyrrol-2-yl (N-CH₂-Ph) | 48 | 159–160 | Ethyl acetate-Hexane |
| 104 | 6,7-(CH₃O)₂ | 3,4-(OCH₃)₂-phenyl | 2-(1-cyclohexyl)pyrrol-2-yl | 51 | 142–143 | Ethyl acetate-Hexane |
| 105 | 6,7-(CH₃O)₂ | 3,4-(OCH₃)₂-phenyl | 1-phenyl-1H-1,2,3,4-tetrazol-5-yl | 72 | 151–152 | Ethyl acetate-Ethyl ether |
| 106 | 6,7-(CH₃O)₂ | 3,4-(OCH₃)₂-phenyl | benzimidazol-2-yl (NH) | 64 | 188–189 | Acetone-Isopropyl ether |
| 107 | 6,7-(CH₃O)₂ | 3,4-(OCH₃)₂-phenyl | 5-fluorobenzimidazol-2-yl (NH) | 82 | 188–190 | Acetone-Isopropyl ether |

TABLE 17

[Structure: quinoline core with positions labeled A¹ (8), 7, 6, A² (5), N at position 1, CH₂—S—Z² at position 2, COOC₂H₅ at position 3, and phenyl group B at position 4]

| Ex. No. | A¹, A² | B | Z² | Yield (%) | mp (°C.) | Recrystallization Solvent |
|---|---|---|---|---|---|---|
| 108 | 6,7-(CH₃O)₂ | 3,4-(OCH₃)₂-phenyl | 5-OC₂H₅-benzimidazol-2-yl | 85 | 155–156 | Methanol |
| 109 | 6,7-(CH₃O)₂ | 3,4-(OCH₃)₂-phenyl | 5-CF₃-benzimidazol-2-yl | 77 | 173–174 | Ethyl ether-Isopropyl ether |
| 110 | 6,7-(CH₃O)₂ | 3,4-(OCH₃)₂-phenyl | 5-Cl-6-CH₃-benzimidazol-2-yl | 92 | 212–213 | Ethyl ether-Isopropyl ether |
| 111 | 6,7-(CH₃O)₂ | 3,4-(OCH₃)₂-phenyl | 5-OC₃H₇-benzimidazol-2-yl | 72 | 118–120 | Ethyl ether-Hexane |
| 112 | 6,7-(CH₃O)₂ | 3,4-(OCH₃)₂-phenyl | 1-CH₃-benzimidazol-2-yl | 71 | 182–183 | Acetone-Isopropyl ether |
| 113 | 6,7-(CH₃O)₂ | 3,4-(OCH₃)₂-phenyl | benzothiazol-2-yl | 88 | 160–161 | Ethyl acetate-Hexane |
| 114 | 6,7-(CH₃O)₂ | 3,4-(OCH₃)₂-phenyl | benzoxazol-2-yl | 80 | 169–170 | Ethyl ether |

TABLE 18

| Ex. No. | $A^1, A^2$ | B | $Z^2$ | Yield (%) | mp (°C.) | Recrystallization Solvent |
|---|---|---|---|---|---|---|
| 115 | 6,7-$(CH_3O)_2$ | 2,3-di-OCH₃ phenyl | (oxadiazole-phenyl) | 42 | 151–152 | Acetone-Ethyl ether |
| 116 | 6,7-$(CH_3O)_2$ | 2,3-di-OCH₃ phenyl | (oxadiazole-pyridyl) | 36 | 167–168 | Acetone-Ethyl ether |
| 117 | 6,7-$(CH_3O)_2$ | 2,3-di-OCH₃ phenyl | (benzamide-imino) | 81 | 183–184 | Ethyl acetate |
| 118 | 6,7-$(CH_3O)_2$ | 2,3-di-OCH₃ phenyl | (thiazolo-pyrimidinone-phenyl) | 71 | 235–237 | Dichloromethane-Ethyl ether |
| 119 | 6,7-$(CH_3O)_2$ | 2,3-di-OCH₃ phenyl | (triazolo-pyridyl) | 89 | 198–199 | Methanol |
| 120 | 6,7-$(CH_3O)_2$ | 2,3-di-OCH₃ phenyl | (imidazo-pyridyl) | 83 | 170–171 | Acetone |
| 121 | 6,7-$(CH_3O)_2$ | 2,3-di-OCH₃ phenyl | (imidazo-pyridazinyl) | 88 | 110–112 | Methanol |

TABLE 19

[Structure: quinoline with A¹ at 8, A² at 5, CH₂-S-Z² at 2-position, COOC₂H₅ at 3, B (phenyl) at 4]

| Ex. No. | A¹, A² | B | Z² | Yield (%) | mp (°C.) | Recrystallization Solvent |
|---|---|---|---|---|---|---|
| 122 | 6,7-(CH₃O)₂ | 3,4-methylenedioxyphenyl | 1-methylimidazol-2-yl | 70 | 176–177 | Ethyl acetate-Hexane |
| 123 | 6,7-(CH₃O)₂ | 2,3,4-trimethoxyphenyl | 1H-benzimidazol-2-yl | 85 | 152–153 | Acetone-Isopropyl ether |
| 124 | 6,7-(CH₃O)₂ | 2,3,4-trimethoxyphenyl | 1-methylimidazol-2-yl | 86 | 131–132 | Acetone-Isopropyl ether |
| 125 | 6,7-(C₂H₅O)₂ | 2,3-dimethoxyphenyl | 1-methylimidazol-2-yl | 73 | 132–133 | Ethyl acetate-Hexane |

TABLE 20

[Structure: quinoline with A¹ at 8, A² at 5, CH₂-S-Z² at 2-position, COOC₂H₅ at 3, B (phenyl) at 4]

| Ex. No. | A¹, A² | B | Z² | Yield (%) | mp (°C.) | Recrystallization Solvent |
|---|---|---|---|---|---|---|
| 126 | 6,7-(CH₃O)₂ | 4-methoxyphenyl | 1-methyl-1H-1,2,4-triazol-5-yl | 79 | 145–146 | Ethyl acetate-Hexane |

TABLE 20-continued

[Structure: quinazoline core with A¹ at position 8, A² at position 5/6, positions 5,6,7,8 labeled on benzo ring; 2-position bears CH₂—S—Z²; 3-position is =C with COOC₂H₅; 4-position bears B (phenyl)]

| Ex. No. | A¹, A² | B | Z² | Yield (%) | mp (°C.) | Recrystallization Solvent |
|---|---|---|---|---|---|---|
| 127 | 6,7-(CH₃O)₂ | 2,3-(OCH₃)₂-C₆H₃ | N-methyl-5-(hydroxymethyl)imidazol-2-yl | 50 | 199–200 | Dichloromethane-Ethyl ether |
| 128 | 6,7-(CH₃O)₂ | 2,3-(OCH₃)₂-C₆H₃ | —CH₂CH₂—S—(N-methylimidazol-2-yl) | 76 | 151–152 | Ethyl acetate-Hexane |
| 129 | H, H | 2,3-(OCH₃)₂-C₆H₃ | N-methylimidazol-2-yl | 95 | 141–142 | Ethyl acetate-Hexane |
| 130 | 6-Cl, H | C₆H₅ | N-methylimidazol-2-yl | 65 | 128–129 | Ethyl acetate-Hexane |

EXAMPLE 131

A mixture of 2-chloromethyl-6,7-dimethoxy-4-(3,4-dimethoxyphenyl)quinazoline (4.5 g), 2-mercaptoethanol (1.13 g), potassium carbonate (2.8 g) and N,N-dimethylformamide (50 ml) was stirred at room temperature for 2 hours. The reaction mixture was poured into water and extracted with ethyl acetate. The ethyl acetate layer was washed with water and dried over magnesium sulfate. Evaporation of the solvent gave 6,7-dimethoxy-4-(3,4-dimethoxyphenyl)-2-(2-hydroxyethylthiomethyl)quinazoline (4.1 g, 82%) which was then recrystallized from ethanol. Colorless prisms. mp. 154°–155° C.

EXAMPLES 132 to 138

According to the same manner as that described in Example 131, the compounds in Table 21 were obtained.

TABLE 21

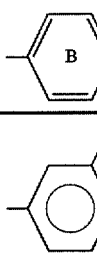

| Ex. No. | $A^1, A^2$ | B | $Z^2$ | Yield (%) | mp (°C.) | Recrystallization Solvent |
|---|---|---|---|---|---|---|
| 132 | 6,7-$(CH_3O)_2$ | 2,3-$(OCH_3)_2$-phenyl | 4-pyridyl | 77 | 143–144 | Acetone |
| 133 | 6,7-$(CH_3O)_2$ | 2,3-$(OCH_3)_2$-phenyl | $-CH_2COOCH_3$ | 83 | 138–139 | Acetone |
| 134 | 6,7-$(CH_3O)_2$ | 2,3-$(OCH_3)_2$-phenyl | 2-pyridyl | 82 | 143–144 | Acetone |
| 135 | 6,7-$(CH_3O)_2$ | 2,3-$(OCH_3)_2$-phenyl | 2-Cl-phenyl | 68 | 143–144 | Acetone |
| 136 | 6,7-$(CH_3O)_2$ | 2,3-$(OCH_3)_2$-phenyl | 1-methyl-1H-tetrazol-5-yl | 81 | 184–185 | Acetone |
| 137 | 6,7-$(CH_3O)_2$ | 2,3-$(OCH_3)_2$-phenyl | benzimidazol-2-yl | 80 | 195–196 | Acetone-Isopropyl ether |
| 138 | 6,7-$(CH_3O)_2$ | 2,3-$(OCH_3)_2$-phenyl | $-CH_2$-(2-Cl-phenyl) | 75 | 132–133 | Ethyl ether |

EXAMPLES 139 to 141

According to the same manner as that described in Example 60, the compounds in Table 22 were obtained.

TABLE 22

![Structure diagram showing a compound with CH3O groups on a benzene ring, connected via N to CH2-S-Z2 with =O, with Y linker and B substituent]

| Ex. No. | B (structure) | Y | R | Yield (%) | mp (°C.) | Recrystallization Solvent |
|---------|---------------|---|---|-----------|----------|---------------------------|
| 139 | phenyl with OCH3, OCH3 | N | -CH2-phenyl-Cl | 83 | 126-127 | Acetone-Isopropyl ether |
| 140 | phenyl-OCH3 | C-COOC2H5 | N——N imidazole with N-CH3 | 58 | 152-153 | Ethyl acetate-Hexane |
| 141 | phenyl-OCH3 | C-COOC2H5 | N-pyrrole with N-CH3 | 59 | 168-169 | Ethyl acetate-Hexane |

EXAMPLE 142

[6,7-Dimethoxy-4-(3,4-dimethoxyphenyl)-3-ethoxycarbonylquinolin-2-yl]methyltriphenylphosphonium chloride (17.4 g) was added at room temperature to a solution of sodium ethoxide in ethanol (prepared from Na (0.62 g) and ethanol (150 ml)). Then a solution of 2-formyl-1-methylimidazole (3.7 g) in ethanol (20 ml) was added dropwise. The mixture was stirred at room temperature for 3 hours, poured into water and extracted with ethyl acetate. The ethyl acetate layer was washed with water and dried over magnesium sulfate, and the solvent was evaporated. The residue was subjected to column chromatography on silica gel. The fractions eluted with chloroform/methanol (100/1, v/v) gave ethyl (E)-6,7-dimethoxy-4-(3,4-dimethoxyphenyl)-2-[2-(1-methylimidazol-2-yl)vinyl]quinoline-3-carboxylate (8.3 g, 67%) which was then recrystallized from ethyl acetate.

Colorless prisms. mp. 206°-208° C.

The fractions eluted thereafter gave ethyl (Z)-6,7-dimethoxy-4-(3,4-dimethoxyphenyl)-2-[2-(1-methylimidazol-2-yl)vinyl]quinoline-3-carboxylate (2.6 g, 21%) as an oil.

NMR (δ ppm) in CDCl$_3$: 0.96 (3H,t,J=7 Hz), 3.35 (3H,s), 3.78 (3H,s), 3.87 (3H,s), 3.96 (3H,s), 3.97 (3H,s), 3.98 (2H,q,J=7 Hz), 6.69 (1H,d,J=12 Hz), 6.8–7.1 (7H,m), 7.13 (1H,s).

Each of the ethyl (E)- and (Z)-6,7-dimethoxy-4-(3,4-dimethoxyphenyl)-2-[2-(1-methylimidazol-2-yl)vinyl]quinoline-3-carboxylate was subjected to catalytic hydrogenation under an atmosphere of hydrogen at 1 atm in ethanol/tetrahydrofuran (1/1, v/v) in the presence of palladium-carbon (5%) to give ethyl 6,7-dimethoxy-4-(3,4-dimethoxyphenyl)-2-[2-(1-methylimidazol-2-yl)ethyl]quinoline-3-carboxylate which was then recrystallized from ethanol. Colorless prisms. mp. 147°-148° C.

EXAMPLE 143

[6,7-Dimethoxy-4-(3,4-dimethoxyphenyl)quinazolin-2-yl]methyltriphenylphosphonium chloride (9.1 g) was added at room temperature to a solution of sodium ethoxide in ethanol (prepared from Na (0.394 g) and ethanol (100 ml)). Then a solution of 2-formyl-1-methylimidazole (1.7 g) in ethanol (10 ml) was added dropwise. The mixture was stirred at room temperature for 3 hours, poured into water and extracted with chloroform. The chloroform layer was washed with water and dried over magnesium sulfate, and the solvent was evaporated. The residue was subjected to column chromatography on silica gel. The fractions eluted with chloroform/methanol (20/1, v/v) gave (E)-6,7-dimethoxy-4-(3,4-dimethoxyphenyl)-2-[2-(1-methylimidazol-2-yl)vinyl]quinazoline (5.1 g, 82%) which was then recrystallized from ethanol-chloroform.

Colorless prisms. mp. 254°-255° C.

Elemental Analysis: Calcd. for $C_{24}H_{24}N_4O_4 \cdot 3/2H_2O$: C,62.73; H,5.92; N,12.19 Found: C,62.62; H,5.85; N,11.90

The fractions eluted thereafter gave (Z)-6,7-dimethoxy-4-(3,4-dimethoxyphenyl)-2-[2-(1-methylimidazol-2-yl)vinyl]quinazoline (0.61 g, 10%) which was then recrystallized from ethanol-chloroform.

Colorless plate crystals. mp. 180°-181° C.

Elemental Analysis: Calcd. for $C_{24}H_{24}N_4O_4 \cdot 1/2H_2O$: C,65.29; H,5.71; N,12.69 Found: C,65.28; H,5.66; N,12.42

Each of the (E)- and (Z)-6,7-dimethoxy-4-(3,4-dimethoxyphenyl)-2-[2-(1-methylimidazol-2-yl)vinyl] quinazoline was subjected to catalytic hydrogenation under an atmosphere of hydrogen at 1 atm in chloroform/ethyl acetate (1/1, v/v) in the presence of palladium-carbon (5%) to give ethyl 6,7-dimethoxy-4-(3,4-dimethoxyphenyl)-2-[2-(1-methylimidazol-2-yl)ethyl]quinazoline which was then recrystallized from ethyl acetate. Colorless prisms. mp. 170°–171° C.

EXAMPLES 144 to 149

According to the same manner as that described in Example 142, the compounds in Table 23 were obtained.

EXAMPLE 150

Ethyl 6,7-dimethoxy-4-(3,4-dimethoxyphenyl)-2-[2-(1-methylimidazol-2-yl)ethyl]quinoline-3-carboxylate (9.0 g) was suspended in ethanol (40 ml), and ethanolic hydrogen chloride (22%, 10 g) was added. After stirring the mixture at room temperature for 5 minutes, ethyl ether (150 ml) was added, and the resulting crystals were collected by filtration and recrystallized from ethanol-ethyl ether to give ethyl 6,7-dimethoxy-4-(3,4-dimethoxyphenyl)-2-[2-(1-methylimidazol-2-yl)ethyl]quinoline-3-carboxylate dihydrochloride (9.1 g).

Pale yellow prisms. mp. 158°–160° C.

TABLE 23

| Ex. No. | $A^1, A^2$ | B | $Z^1$ | q | mp (°C.) | Recrystallization Solvent |
|---|---|---|---|---|---|---|
| 144 | 6,7-$(CH_3O)_2$ | 3,4-$(OCH_3)_2$-phenyl | 1-methyl-2-ethyl-imidazol-5-yl | 1 | 183–184 | Ethyl acetate |
| 145 | 6,7-$(CH_3O)_2$ | 3,4-$(OCH_3)_2$-phenyl | 1-methyl-pyrrol-2-yl | 1 | 155–156 | Ethyl acetate-Hexane |
| 146 | 6,7-$(C_2H_5O)_2$ | 3,4-$(OCH_3)_2$-phenyl | 1-methyl-imidazol-2-yl | 1 | 134–135 | Ethyl acetate-Hexane |
| 147 | 6,7-$(CH_3O)_2$ | 3,4-$(OCH_3)_2$-phenyl | 2-ethyl-imidazol-5-yl | 1 | Note 1) 112–113 | Ethyl acetate-Hexane |
| 148 | 6,7-$(CH_3O)_2$ | 3,4-$(OCH_3)_2$-phenyl | pyridin-2-yl | 1 | 140–141 | Ethyl acetate-Hexane |
| 149 | 6,7-$(CH_3O)_2$ | 4-$OCH_3$-phenyl | 1-methyl-imidazol-2-yl | 1 | 132–133 | Ethyl acetate |

Note 1) ½ hydrate

Elemental Analysis: Calcd. for $C_{28}H_{31}N_3O_6 \cdot 2HCl \cdot 1/3C_2H_5OH \cdot 1/2H_2O$: C,57.11; H,6.02; N,6.97 Found: C,57.03; H,6.15; N,7.00

EXAMPLE 151

[6,7-Dimethoxy-4-(3,4-dimethoxyphenyl)-3-ethoxycarbonylquinolin-2-yl]methyltriphenylphosphonium chloride (3.0 g) was added at room temperature to a solution of sodium ethoxide in ethanol (prepared from Na (0.13 g) and ethanol (45 ml)). Then 3-(1-methylimidazol-2-yl) propionaldehyde (0.787 g) was added. The mixture was stirred at room temperature for 3 hours, poured into water and extracted with ethyl acetate. The ethyl acetate layer was washed with water and dried over magnesium sulfate, and the solvent was evaporated. The residue was subjected to column chromatography on silica gel. The fractions eluted with ethyl acetate/methanol (30/1, v/v) gave ethyl (E)-6,7-dimethoxy-4-(3,4-dimethoxyphenyl)-2-[2-[2-(1-methylimidazol-2-yl)ethyl]vinyl]quinoline-3-carboxylate (0.36 g, 15%) as an oil.

NMR ($\delta$ ppm) in $CDCl_3$: 1.03 (3H,t,J=7 Hz), 2.7–3.0 (4H,m), 3.60 (3H,s), 3.79 (3H,s), 3.87 (3H,s), 3.97 (3H,s), 4.05 (3H,s), 4.09 (2H,q,J=7 Hz), 6.7–7.2 (8H,m), 7.43 (1H,s).

The fractions eluted thereafter gave ethyl (Z)-6,7-dimethoxy-4-(3,4-dimethoxyphenyl)-2-[2-[2-(1-methylimidazol-2-yl)ethyl]vinyl]quinoline-3-carboxylate (0.2 g, 8%) as an oil.

NMR ($\delta$ ppm) in $CDCl_3$: 1.02 (3H,t,J=7 Hz), 2.8–3.2 (4H,m), 3.58 (3H,s), 3.80 (3H,s), 3.88 (3H,s), 3.96 (3H,s), 4.05 (3H,s), 4.07 (2H,q,J=7 Hz), 6.08 (1H,dt,J=7.4&11.4 Hz), 6.6–7.0 (7H,m), 7.42 (1H,s).

A mixture of the ethyl (E)- and (Z)-6,7-dimethoxy-4-(3, 4-dimethoxyphenyl)-2-[2-[2-(1-methylimidazol-2-yl)ethyl] vinyl]quinoline-3-carboxylates was subjected to catalytic hydrogenation under an atmosphere of hydrogen at 1 atm in ethanol/tetrahydrofuran (1/4, v/v) in the presence of palladium-carbon (5%) and treated with ethanolic hydrogen chloride to give ethyl 6,7-dimethoxy-4-(3,4-dimethoxyphenyl)-2-[4-(1-methylimidazol-2-yl)butyl] quinoline-3-carboxylate which was then recrystallized from chloroform-ethyl acetate. Pale yellow crystals. mp. 180°–183° C.

Elemental Analysis: Calcd. for $C_{30}H_{35}N_3O_6 \cdot 2HCl \cdot H_2O$: C,57.69; H,6.29; N,6.73 Found: C,57.48; H,6.09; N,6.60

EXAMPLE 152

A mixture of ethyl 2-chloromethyl-6,7-dimethoxy-4-(3,4-dimethoxyphenyl)quinoline-3-carboxylate (1.5 g), 2-hydroxy-6-methylpyridine (0.4 g), potassium carbonate (0.511 g) and N,N-dimethylformamide (20 ml) was stirred at 120° C. for 2 hours. The reaction mixture was poured into water and extracted with ethyl acetate. The ethyl acetate layer was washed with water and dried over magnesium sulfate, and the solvent was evaporated. The residual oil was subjected to column chromatography on silica gel. The fractions eluted with ethyl acetate gave 6,7-dimethoxy-4-(3, 4-dimethoxyphenyl)-2-[(2-methyl-6-pyridyl)oxymethyl] quinoline-3-carboxylate (0.79 g, 46%) which was then recrystallized from chloroform-hexane.

Yellow prisms. mp. 173°–174° C.

Elemental Analysis: Calcd. for $C_{29}H_{30}N_2O_7$: C,67.17; H,5.83; N,5.40 Found: C,66.97; H,6.02; N,5.16

EXAMPLE 153

A mixture of ethyl 2-iodomethyl-6,7-dimethoxy-4-(3,4-dimethoxyphenyl)quinoline-3-carboxylate (9.0 g), 2-hydroxy-1-methylimidazole (1.8 g), silver (I) carbonate $(Ag_2CO_3)(5.1$ g) and benzene (100 ml) was stirred at 50° C. for 18 hours. The insoluble solid was filtered off. The filtrate was washed with water and dried over magnesium sulfate, and the solvent was evaporated. The residual oil was subjected to column chromatography on silica gel. The fractions eluted with chloroform/ethyl acetate (5/1, v/v) gave ethyl 6,7-dimethoxy-4-(3,4-dimethoxyphenyl)-2-[(1-methyl-2-imidazolyl)oxymethyl]quinoline-3-carboxylate (0.8 g, 9%) which was then recrystallized from ethyl acetate-hexane.

Colorless prisms. mp. 151°–152° C.

Elemental Analysis: Calcd. for $C_{27}H_{29}N_3O_7$: C,63.90; H,5.87; N,8.28 Found: C,63.74; H,5.87; N,7.99

EXAMPLE 154

A mixture of ethyl 6,7-dimethoxy-4-(3,4-dimethoxyphenyl)-2-[(1-methylimidazol-2-yl)thiomethyl] quinoline-3-carboxylate (0.6 g), 2N sodium hydroxide (1.7 ml) and ethanol (12 ml) was refluxed for 6 hours. The reaction mixture was concentrated in vacuo. The residue was diluted with water, washed with ethyl acetate, made acidic with 2N hydrochloric acid and extracted with ethyl acetate. The extract was washed with water, dried over magnesium sulfate and concentrated in vacuo to give crystals. The crystals were recrystallized from ethanol-ethyl ether to give 6,7-dimethoxy-4-(3,4-dimethoxyphenyl)-2-[(1-methylimidazol-2-yl)thiomethyl]quinoline-3-carboxylic acid (0.3 g, 53%) as colorless prisms. mp. 213°–214° C.

Elemental Analysis: Calcd. for $C_{25}H_{25}N_3O_6S \cdot 1/2H_2O$: C,59.51; H,5.19; N,8.32 Found: C,59.38; H,5.40; N,7.93

EXAMPLE 155

Oily sodium hydride (60%, 0.1 g) was added to a solution of ethyl 6,7-dimethoxy-4-(3,4-dimethoxyphenyl)-2(1H)-quinolone-3-carboxylate (0.5 g) in N,N-dimethylformamide (20 ml) under ice-cooling. After stirring at room temperature for 30 minutes, 2-bromopropane (0.5 ml) was added. The mixture was stirred at 60° C. for 5 hours, poured into water and extracted with ethyl acetate. The ethyl acetate layer was washed with water and dried over magnesium sulfate. Evaporation of the solvent gave ethyl 6,7-dimethoxy-4-(3, 4-dimethoxyphenyl)-2-isopropoxyquinoline-3-carboxylate (0.388 g, 70%) which was then recrystallized from ethyl ether. mp. 142°–143° C.

EXAMPLE 156

Oily sodium hydride (60%, 0.033 g) was added to a solution of 2-hydroxymethyl-1-methylimidazole (0.085 g) in N,N-dimethylformamide (7 ml) under ice-cooling. After stirring at the same temperature for 10 minutes, ethyl 2-chloro-6,7-dimethoxy-4-(3,4-dimethoxyphenyl) quinoline-3-carboxylate (0.3 g) was added. The mixture was stirred under ice-cooling for 1 hour followed by stirring at room temperature for 20 hours, poured into water and extracted with ethyl acetate. The ethyl acetate layer was washed with water and dried over magnesium sulfate, and the solvent was evaporated. The residual oil was subjected to column chromatography on silica gel. The fractions eluted with ethyl acetate/methanol (30/1, v/v) gave ethyl 6,7-dimethoxy-4-(3,4-dimethoxyphenyl)-2-(1-methylimidzol-2-yl)methoxyquinoline-3-carboxylate (0.26 g, 73%) which was then recrystallized from ethyl acetate-hexane. mp. 209°–210° C.

EXAMPLE 157

Oily sodium hydride (60%, 0.05 g) was added to a mixture of ethyl 6,7-dimethoxy-4-(3,4-dimethoxyphenyl)-2- mercaptoquinoline-3-carboxylate (0.2 g), 2-chloromethyl-1-methylimidazole (0.09 g) and N,N-dimethylformamide (8 ml) under ice-cooling. The mixture was stirred at the same temperature for 1 hour followed by stirring at room temperature for 18 hours, poured into water and extracted with ethyl acetate. The ethyl acetate layer was washed with water and dried over magnesium sulfate, and the solvent was evaporated. The residual oil was subjected to column chromatography on silica gel. The fractions eluted with ethyl acetate/methanol (30/1, v/v) gave ethyl 6,7-dimethoxy-4-(3,4-dimethoxyphenyl)-2-[(1-methylimidzol-2-yl)methylthio]-quinoline-3-carboxylate (0.214 g, 87%). mp. 141°–142° C.

EXAMPLE 158

A mixture of ethyl 2-chloromethyl-6,7-dimethoxy-4-(3,4-dimethoxyphenyl)quinoline-3-carboxylate (0.58 g), 2-aminomethyl-1-methylimidazole hydrochloride (0.24 g), potassium carbonate (0.63 g) and N,N-dimethylformamide (15 ml) was stirred at room temperature for 2 hours. The mixture was poured into water and extracted with ethyl acetate. The ethyl acetate layer was washed with water and dried over magnesium sulfate, and the solvent was evaporated. The residual oil was subjected to column chromatography on silica gel. The fractions eluted with chloroform/methanol (50/1, v/v) gave 2,3-dihydro-6,7-dimethoxy-9-(3,4-dimethoxyphenyl)-2-(1-methylimidzol-2-ylmethyl)-1-oxo-1H-pyrrolo[3,4-b]quinoline (0.27 g, 43%) of the formula:

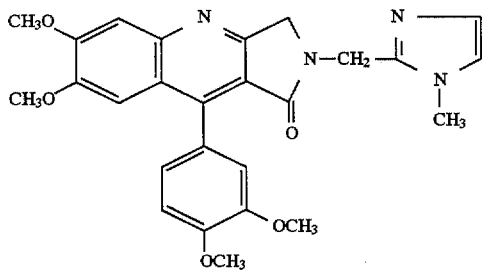

which was then recrystallized from ethyl acetate. mp. 245°–246° C.

EXAMPLE 159

Three drops of conc. sulfuric acid was added to a mixture of 2-amino-4,5,3',4'-tetramethoxybenzophenone (1.55 g), dimethyl acetonedicarboxylate (0.936 g) and acetic acid (30 ml), and the resulting mixture was stirred at 100° C. for 2.5 hours. The reaction mixture was concentrated under reduced pressure, the residue was poured into water, neutralized with an aqueous saturated sodium bicarbonate solution and extracted with chloroform. The chloroform layer was washed with water dried over magnesium sulfate, and the solvent was evaporated under reduced pressure. The resulting crystals were recrystallized from acetone to give methyl 6,7-dimethoxy-4-(3,4-dimethoxyphenyl)-3-methoxycarbonylquinoline-2-acetate (1.41 g, 64%). Colorless prisms. mp. 170°–171° C.

EXAMPLE 160

According to the same manner as that described in Example 159, ethyl 6,7-dimethoxy-4-(3,4-dimethoxyphenyl)-3-ethoxycarbonylquinoline-2-acetate was obtained and then recrystallized from ethyl acetate-isopropyl ether.

Colorless prisms. mp. 146°–147° C.

EXAMPLE 161

Powdered aluminium chloride (0.21 g) was added to a mixture of 2-amino-5-chloro-3',4'-dimethoxybenzophenone (0.23 g) and methyl cyanoacetate (5 ml), and the resulting mixture was stirred at 100° C. for 2.5 hours. The reaction mixture was poured into water and extracted with ethyl acetate. The ethyl acetate layer was washed with water and dried over magnesium sulfate, and the solvent was evaporated. The residue was subjected to column chromatography on silica gel. The fractions eluted with hexane/ethyl acetate (4/1, v/v) gave methyl 6-chloro-4-(3,4-dimethoxyphenyl) quinazoline-2-acetate (0.161 g, 55%) which was then recrystallized from isopropyl ether. Colorless needles. mp. 144°–145° C.

EXAMPLE 162

According to the same manner as that described in Example 161, methyl 6-chloro-4-phenylquinazoline-2-acetate was obtained and recrystallized from isopropyl ether. Colorless needles. mp. 122°–123° C.

EXAMPLE 163

According to the same manner as that described in Example 161, methyl 6,7-dimethoxy-4-(3,4-dimethoxyphenyl)quinazoline-2-acetate was obtained and recrystallized from isopropyl ether. Colorless needles. mp. 152°–153° C.

EXAMPLE 164

A solution of ethyl 6,7-dimethoxy-4-(3,4-dimethoxyphenyl)-3-ethoxycarbonylquinoline-2-acetate (5.8 g) in tetrahydrofuran (100 ml) was added dropwise to a suspension of lithium aluminium hydride (0.455 g) in tetrahydrofuran (50 ml) at 0° C. After stirring the reaction mixture at 0° C. for 1 hour, water (2.5 ml) was added dropwise, and the mixture was stirred for additional 30 minutes. The insoluble solid was filtered off, and the filtrate was concentrated under reduced pressure. The residue was subjected to column chromatography on silica gel. The fractions eluted with chloroform/ethyl acetate (1/1, v/v) gave ethyl 2-(2-hydroxyethyl)-6,7-dimethoxy-4-(3,4-dimethoxyphenyl)quinoline-3-carboxylate (1.75 g, 33%) which was then recrystallized from ethyl acetate-hexane. Colorless prisms. mp. 150°–151° C.

EXAMPLE 165

Phosphorus tribromide (PBr$_3$)(1.0 g) was added dropwise to a solution of ethyl 2-(2-hydroxyethyl)-6,7-dimethoxy-4-(3,4-dimethoxyphenyl)quinoline-3-carboxylate(1.7 g) in benzene (50 ml) at room temperature. The mixture was stirred at 80° C. for 1 hour, poured into ice-water, neutralized with an aqueous saturated sodium bicarbonate solution and extracted with chloroform. The chloroform layer was washed with water and dried over magnesium sulfate, and the solvent was evaporated. The residue was subjected to column chromatography on silica gel. The fractions eluted with chloroform/ethyl acetate (1/1, v/v) gave ethyl 2-(2-bromoethyl)-6,7-dimethoxy-4-(3,4-dimethoxyphenyl) quinoline-3-carboxylate (0.49 g, 26%) which was then recrystallized from ethyl acetate-hexane. Colorless prisms. mp. 132°–133° C.

EXAMPLE 166

Oily sodium hydride (60%, 0.323 g) was added to a solution of 2-ethylimidazole (0.776 g) in N,N- dimethylformamide (30 ml), and the mixture was stirred at room temperature for 15 minutes. Then ethyl 2-chloromethyl-6,7-dimethoxy-4-(3,4-dimethoxyphenyl) quinoline-3-carboxylate(3.0 g) was added. The mixture was stirred at 80° C. for 1 hour and poured into water, and the resulting crystals were collected by filtration and recrystallized from ethanol to give ethyl 2-(2-ethylimidazol-1-ylmethyl)-6,7-dimethoxy-4-(3,4-dimethoxyphenyl) quinoline-3-carboxylate (2.5 g, 74%). Colorless prisms. mp. 163°–164° C.

EXAMPLES 167 to 176

According to the same manner as that described in Example 166, the compounds in Tables 24 and 25 were obtained.

TABLE 24

| Ex. No. | B | Y | —N⟨P⟩ | mp (°C.) | Recrystallization Solvent |
|---|---|---|---|---|---|
| 167 | 2,3-(OCH$_3$)$_2$-phenyl | C—COOC$_2$H$_5$ | imidazolyl | 208–209 | Dichloromethane-Hexane |
| 168 | 2,3-(OCH$_3$)$_2$-phenyl | C—COOC$_2$H$_5$, CH$_3$ | 2-methylimidazolyl | 177–178 | Ethyl acetate-Hexane |
| 169 | 2,3-(OCH$_3$)$_2$-phenyl | C—COOC$_2$H$_5$ | 1,2,4-triazolyl | 134–135 | Ethanol |
| 170 | 4-OCH$_3$-phenyl | C—COOC$_2$H$_5$ | imidazolyl | 200–201 | Ethyl acetate-Hexane |
| 171 | 4-OCH$_3$-phenyl | C—COOC$_2$H$_5$, CH$_3$ | 2-methylimidazolyl | 148–149 | Ethyl acetate-Hexane |

TABLE 25

| Ex. No. | B (phenyl substitution) | Y | —N⟨P⟩ | mp (°C.) | Recrystallization Solvent |
|---|---|---|---|---|---|
| 172 | —⟨phenyl⟩—OCH₃ (para) | C—COOC₂H₅ | imidazolyl | 157–158 | Ethanol |
| 173 | —⟨phenyl⟩ with OCH₃, OCH₃ | N | imidazolyl | 184–185 | Dichloromethane-Ethyl ether |
| 174 | —⟨phenyl⟩ with OCH₃, OCH₃ | N | 2-methylimidazolyl (CH₃) | 223–224 | Dichloromethane-Ethyl ether |
| 175 | —⟨phenyl⟩ with OCH₃, OCH₃ | N | 2-ethylimidazolyl (C₂H₅) | 188–189 | Ethyl acetate-Hexane |
| 176 | —⟨phenyl⟩ with OCH₃, OCH₃ | N | imidazolyl | 198–199 | Dichloromethane-Ethyl ether |

EXAMPLE 177

Oily sodium hydride (60%, 0.044 g) was added to a solution of imidazole (0.075 g) in N,N-dimethylformamide (5 ml), and the mixture was stirred at room temperature for 15 minutes. Then ethyl 2-(2-bromoethyl)-6,7-dimethoxy-4-(3,4-dimethoxyphenyl)quinoline-3-carboxylate (0.46 g) was added. The mixture was stirred at 80° C. for 1 hour, poured into water and extracted with ethyl acetate. The ethyl acetate layer was washed with water and dried over magnesium sulfate, and the solvent was evaporated under reduced pressure. The residue was subjected to column chromatography on silica gel. The fractions eluted with ethyl acetate/methanol (10/1, v/v) gave ethyl 2-[2-(1-imidazolyl)ethyl]-6,7-dimethoxy-4-(3,4-dimethoxyphenyl)quinoline-3-carboxylate (0.295 g, 66%) which was then recrystallized from ethyl acetate-hexane. Colorless prisms. mp. 173°–174° C.

EXAMPLES 178 to 180

According to the same manner as that described in Example 177, the compounds in Tables 26 were obtained.

TABLE 26

[Structure: dimethoxyphenyl-quinoline with B ring, Y substituent, and CH2-N-P group]

| Ex. No. | B | Y | —N P | mp (°C.) | Recrystallization Solvent |
|---|---|---|---|---|---|
| 178 | 2,4-di-OCH3-phenyl | C—COOC2H5 | H2N-triazole (—N\N=) | 209–210 | Dichloromethane-Hexane |
| 179 | 2,4-di-OCH3-phenyl | C—COOC2H5 | O=C(CH3)-N-triazole | 198–199 | Ethanol |
| 180 | 4-OCH3-phenyl | C—COOC2H5 | C2H5-triazole | 124–125 | Ethyl acetate-Hexane |

EXAMPLE 181

Oily sodium hydride (60%, 0.323 g) was added to a solution of 1H-1,2,4-triazole (0.558 g) in N,N-dimethylformamide (30 ml), and the mixture was stirred at room temperature for 15 minutes. Then ethyl 2-chloromethyl-6,7-dimethoxy-4-(3,4-dimethoxyphenyl) quinoline-3-carboxylate(3.0 g) was added. The mixture was stirred at 80° C. for 1 hour, poured into water and extracted with ethyl acetate. The ethyl acetate layer was washed with water and dried over magnesium sulfate, and the solvent was evaporated under reduced pressure. The residue was subjected to column chromatography on silica gel. The fractions firstly eluted with chloroform/methanol (40/1, v/v) gave ethyl 6,7-dimethoxy-4-(3,4-dimethoxyphenyl)-2-(1,2,4-triazol-1-ylmethyl)quinoline-3-carboxylate (1.7 g, 53%) which was then recrystallized from ethyl acetate-hexane. Colorless prisms. mp. 176°–177° C.

EXAMPLE 182

The fractions eluted thereafter of the column chromatography in Example 181 gave ethyl 6,7-dimethoxy-4-(3,4-dimethoxyphenyl)-2-(1,2,4-triazol-4-ylmethyl)quinoline-3-carboxylate (0.07 g, 2%) which was then recrystallized from ethyl acetate-hexane. Colorless prisms. mp. 226°–227° C.

EXAMPLE 183

According to the same manner as that described in Example 181, ethyl 6,7-dimethoxy-4-(4-methoxyphenyl)-2-(1,2,4-triazol-1-ylmethyl)quinoline-3-carboxylate was obtained and then recrystallized from ethyl acetate-hexane. Colorless prisms. mp. 150°–151° C.

EXAMPLE 184

The fractions eluted thereafter of the column chromatography in Example 183 gave ethyl 6,7-dimethoxy-4-(4-methoxyphenyl)-2-(1,2,4-triazol-4-ylmethyl)quinoline-3-carboxylate which was then recrystallized from ethyl acetate-hexane. Colorless needles. mp. 218°–219° C.

EXAMPLE 185

According to the same manner as that described in Example 181, 6,7-dimethoxy-4-(4-methoxyphenyl)-2-(1,2,4-triazol-1-ylmethyl)quinazoline was obtained and then recrystallized from dichloromethane-ethyl ether. Colorless prisms. mp. 206°–207° C.

EXAMPLE 186

The fractions eluted thereafter of the column chromatography in Example 185 gave 6,7-dimethoxy-4-(4-methoxyphenyl)-2-(1,2,4-triazol-4-ylmethyl)quinazoline which was then recrystallized from dichloromethane-ethyl ether. Colorless needles. mp. 212°–213° C.

EXAMPLE 187

A mixture of methyl 2-ethyl-6,7-dimethoxy-4-(3,4-dimethoxyphenyl)quinoline-3-carboxylate (0.5 g), 4N sodium hydroxide (20 ml) and methanol was stirred for 14 hours under reflux, poured into water, made acidic and extracted with chloroform. The chloroform layer was washed with water and dried over magnesium sulfate. Evaporation of the solvent gave 6,7-dimethoxy-4-(3,4-dimethoxyphenyl)-2-ethylquinoline-3-carboxylic acid (0.343 g, 71%) which was then recrystallized from acetone-methanol. mp. 264°–267° C.

EXAMPLE 188

One drop of N,N-dimethylformamide was added to a mixture of 2-ethyl-6,7-dimethoxy-4-(3,4-dimethoxyphenyl)-quinoline-3-carboxylic acid (0.2 g), oxalyl chloride (0.05 ml) and tetrahydrofuran (10 ml), and the resulting mixture was stirred at room temperature for 1 hour and concentrated under reduced pressure. The residue was dissolved in tetrahydrofuran (10 ml). The solution was added dropwise to a mixture of diethyl 2-aminoethylphosphonate (0.195 g), triethylamine (0.1 ml) and tetrahydrofuran (10 ml). The reaction mixture was stirred at room temperature for 1 hour and then under reflux for 3 hours, poured into water and extracted with chloroform. The chloroform layer was washed successively with 2N hydrochloric acid, an aqueous saturated sodium bicarbonate solution and water, and dried over magnesium sulfate. Evaporation of the solvent gave N-(2-diethoxyphosphorylethyl)-6,7-dimethoxy-4-(3,4-dimethoxyphenyl)-2-ethylquinoline-3-carboxamide (0.21 g, 75%) which was then recrystallized from ethyl ether. mp. 157°–158° C.

EXAMPLE 189

A solution of methyl 6,7-dimethoxy-4-(3,4-dimethoxyphenyl)-2-methylquinoline-3-carboxylate (0.4 g) in tetrahydrofuran (10 ml) was added dropwise to a suspension of lithium aluminium hydride ($LiAlH_4$)(0.114 g) in tetrahydrofuran (10 ml) at room temperature. The mixture was stirred at room temperature for 1.5 hours, and water was added. The resulting mixture was extracted with ethyl acetate. The ethyl acetate layer was washed with water and dried over magnesium sulfate, the solvent was evaporated, and the resulting crystals were collected by filtration and recrystallized from methanol to give 3-hydroxymethyl-6,7-dimethoxy-4-(3,4-dimethoxyphenyl)-2-methylquinoline (0.326 g, 88%). mp. 200°–201° C.

EXAMPLE 190

According to the same manner as that described in Example 189, 2-ethyl-3-hydroxymethyl-6,7-dimethoxy-4-(3,4-dimethoxyphenyl)quinoline was obtained and recrystallized from acetone-isopropyl ether. mp. 192°–193° C.

EXAMPLE 191 m-Chloroperbenzoic acid (80%, 1.4 g) was added under ice-cooling to a solution of ethyl 6,7-dimethoxy-4-(3,4-dimethoxyphenyl)-2-(1-methylimidazol-2-ylmethylthio)quinoline-3-carboxylate (3.0 g) in dichloromethane (90 ml), and the mixture was stirred at the same temperature for 3 hours. The reaction mixture was washed successively with an aqueous saturated $NaHSO_3$ solution, aqueous saturated sodium bicarbonate solution and water and dried over magnesium sulfate, and the solvent was evaporated. The residual oil was subjected to column chromatography on silica gel. The fractions eluted with ethyl acetate/dichloromethane (4:1, v/v) gave ethyl 6,7-dimethoxy-4-(3,4-dimethoxyphenyl)-2-(1-methylimidazol-2-ylmethylsulfinyl)quinoline-3-carboxylate (2.17 g, 70%). mp. 151°–152° C.

EXAMPLE 192

The fractions eluted thereafter of the column chromatography in Example 191 gave ethyl 6,7-dimethoxy-4-(3,4-dimethoxyphenyl)-2-(1-methylimidazol-2-ylmethylsulfonyl)-quinoline-3-carboxylate (0.47 g, 14%). mp. 132°–133° C.

EXAMPLE 193

A mixture of ethyl 6,7-dimethoxy-4-(3,4-dimethoxyphenyl)-2-methylquinoline-3-carboxylate (411 mg), N-bromosuccinimide (214 mg), 2,2-azobis (isobutyronitrile)(10 mg) and carbon tetrachloride (10 ml) was stirred under reflux for 5 hours. The reaction mixture was washed with water, dried over magnesium sulfate. The solvent was evaporated under reduced pressure, and the residue was subjected to column chromatography on silica gel. The fractions eluted with chloroform/ethyl acetate (10/1, v/v) gave ethyl 2-bromomethyl- 6,7-dimethoxy-4-(3,4-dimethoxyphenyl)quinoline-3-carboxylate (285 mg, 58%) which was then recrystallized from ethyl acetate-hexane. Colorless prisms. mp. 135°–136° C.

Elemental Analysis: Calcd. for $C_{23}H_{24}NO_6Br$: C,56.34; H,4.93; N,2.86 Found: C,55.98; H,5.23; N,2.62

EXAMPLE 194

According to the same manner as that described in Example 193, propyl 2-bromomethyl-6,7-dimethoxy-4-(3,4-dimethoxyphenyl)quinoline-3-carboxylate (48%) was obtained and recrystallized from ethyl acetate-isopropyl ether. Colorless prisms. mp. 144°–145° C.

Elemental Analysis: Calcd. for $C_{24}H_{26}NO_6Br$: C,57.15; H,5.20; N,2.78 Found: C,56.75; H,5.30; N,2.68

EXAMPLE 195

According to the same manner as that described in Example 193, butyl 2-bromomethyl-6,7-dimethoxy-4-(3,4-dimethoxyphenyl)quinoline-3-carboxylate (56%) was obtained and recrystallized from ethyl acetate-ethyl ether. Colorless prisms. mp. 160°–161° C.

Elemental Analysis: Calcd. for $C_{25}H_{28}NO_6Br$: C,57.92; H,5.44; N,2.70

Found: C,57.96; H,5.53; N,2.50

EXAMPLE 196

According to the same manner as that described in Example 1, ethyl 2-chloromethyl-6,7-dimethoxy-4-(4-methoxy-3-propoxyphenyl)quinoline-3-carboxylate was obtained and recrystallized from ethanol. Colorless prisms. mp. 126°–128° C.

EXAMPLE 197

Methanol (15 ml) was added dropwise under reflux to a mixture of methyl 6,7-dimethoxy-4-(3,4-dimethoxyphenyl)-quinazoline-2-acetate (4.0 g), sodium borohydride (1.9 g) and tetrahydrofuran (80 ml). The mixture was stirred under reflux for 2 hours, poured into water and extracted with ethyl acetate. The ethyl acetate layer was washed with water, dried over magnesium sulfate. The solvent was evaporated under reduced pressure to give 6,7-dimethoxy-4-(3,4-dimethoxyphenyl)-2-(2-hydroxyethyl)quinazoline (3.0 g, 81%) which was then recrystallized from ethyl acetate. Colorless needle crystals. mp. 165°–166° C.

EXAMPLE 198

According to the same manner as that described in Example 165, 2-(2-bromoethyl)-6,7-dimethoxy-4-(3,4-dimethoxyphenyl)quinazoline (56%) was obtained and recrystallized from ethyl acetate. Colorless needles. mp. 166°–167° C.

EXAMPLES 199 to 205

According to the same manner as that described in Example 1, the compounds in Table 27 were obtained.

methoxyphenyl)-2-(1,2,4-triazol-1-ylmethyl)quinoline-3-carboxylate (55.6 mg) in dichloromethane (2 ml), and the mixture was stirred at the same temperature for 6 hours. The

TABLE 27

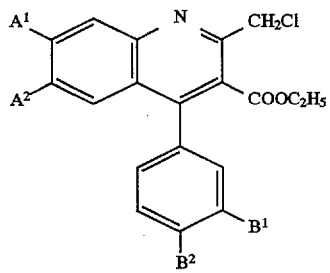

| Ex. No. | $A^1$ | $A^2$ | $B^1$ | $B^2$ | Yield (%) | mp (°C.) | Recrystallization Solvent |
|---|---|---|---|---|---|---|---|
| 199 | $CH_3O$ | $CH_3O$ | Cl | Cl | 57 | 159–160 | Ethyl acetate-Hexane |
| 200 | $(CH_3)_2CHO$ | $CH_3O$ | $CH_3O$ | $CH_3O$ | 66 | 138–140 | Ethyl acetate-Hexane |
| 201 | $CH_3O$ | $(CH_3)_2CHO$ | $CH_3O$ | $CH_3O$ | 48 | 125–126 | Ethyl acetate-Hexane |
| 202 | $CH_3O$ | $CH_3O$ | $(CH_3)_2CHO$ | $CH_3O$ | 50 | 126–127 | Ethanol |
| 203 | $CH_3O$ | $CH_3O$ | $CH_3O$ | $(CH_3)_2CHO$ | 48 | 149–150 | Ethanol |
| 204 | $CH_3O$ | $CH_3O$ | $(CH_3)_2CHO$ | $(CH_3)_2CHO$ | 48 | 118–119 | Ethyl acetate-Hexane |
| 205 | $CH_3O$ | $(CH_3)_2CHO$ | $(CH_3)_2CHO$ | $(CH_3)_2CHO$ | 60 | 99–100 | Ethyl acetate-Hexane |

EXAMPLES 206 to 214

According to the same manner as that described in Example 181, the compounds in Table 28 were obtained.

reaction mixture was poured into water and extracted with chloroform. The chloroform layer was washed with a saturated aqueous sodium carbonate solution and water, and

TABLE 28

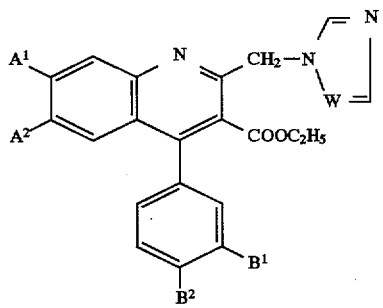

| Ex. No. | $A^1$ | $A^2$ | $B^1$ | $B^2$ | W | Yield (%) | mp (°C.) | Recrystallization Solvent |
|---|---|---|---|---|---|---|---|---|
| 206 | $CH_3O$ | $CH_3O$ | H | Cl | CH | 65 | 156–157 | Ethyl acetate-Hexane |
| 207 | $CH_3O$ | $CH_3O$ | Cl | Cl | CH | 64 | 183–184 | Ethyl acetate-Hexane |
| 208 | $CH_3O$ | $CH_3O$ | Cl | Cl | N | 48 | 160–161 | Ethyl acetate-Hexane |
| 209 | $(CH_3)_2CHO$ | $CH_3O$ | $CH_3O$ | $CH_3O$ | N | 58 | 154–155 | Ethyl acetate-Hexane |
| 210 | $CH_3O$ | $(CH_3)_2CHO$ | $CH_3O$ | $CH_3O$ | N | 62 | —[1] | |
| 211 | $CH_3O$ | $CH_3O$ | $(CH_3)_2CHO$ | $CH_3O$ | N | 65 | 183–185 | Ethyl acetate-Hexane |
| 212 | $CH_3O$ | $CH_3O$ | $CH_3O$ | $(CH_3)_2CHO$ | N | 75 | 165–166 | Ethyl acetate-Hexane |
| 213 | $CH_3O$ | $CH_3O$ | $(CH_3)_2CHO$ | $(CH_3)_2CHO$ | N | 50 | 134–135 | |
| 214 | $CH_3O$ | $(CH_3)_2CHO$ | $(CH_3)_2CHO$ | $(CH_3)_2CHO$ | N | 66 | Oil[2] | |

[1] Amorphous solid. NMR (δ ppm in $CDCl_3$): 0.87(3H, t, J=7.2Hz), 1.33(6H, d, J=6.0Hz), 3.85(3H, s), 3.93(2H, q, J=7.2Hz), 3.96(3H, s), 4.02(3H, s), 4.43(1H, m), 5.68(1H, d, J=14.8Hz), 5.77(1H, d, J=14.8Hz), 6.82–7.01(4H, m), 7.41(1H, s), 7.93(1H, s), 8.27(1H, s).
[2] NMR (δ ppm in $CDCl_3$): 0.84(3H, t, J=7.2Hz), 1.26–1.45(18H, m), 3.93(2H, q, J=7.0Hz), 4.02(3H, s), 4.21(1H, m), 4.51(1H, m), 4.56(1H, m), 5.73(2H, s), 6.80–6.92(3H, m), 7.01(1H, d, J=8.2Hz), 7.41(1H, s), 7.93(1H, s), 8.27(1H, s).

EXAMPLE 215

Titanium tetrachloride ($TiCl_4$)(125 mg) was added at 0° C. to a solution of ethyl 6,7-dimethoxy-4-(4-isopropoxy-3- dried over magnesium sulfate. The solvent was evaporated. The residual oil was subjected to column chromatography on silica gel. The fractions eluted with ethyl acetate/chloroform(3/2, v/v) gave ethyl 6,7-dimethoxy-4-(4- hydroxy-3-methoxyphenyl)-2-(1,2,4-triazol-1-ylmethyl) quinoline-3-carboxylate (24.5 mg, 48%) which was then recrystallized from ethyl acetate-hexane. mp. 176°–178° C.

NMR (δ ppm in CDCl₃): 0.88 (3H,t,J=7.2 Hz), 3.80 (3H,s), 3.88 (3H,s), 3.96 (2H,q,J=7.2 Hz), 4.05 (3H,s), 5.73 (2H,s), 5.80 (1H, broad s), 6.80–7.06 (4H,m), 7.42 (1H,s), 7.94 (1H,s), 8.27 (1H,s).

EXAMPLES 216 to 218

According to the same manner as that described in Example 215, the compounds in Table 29 were obtained.

TABLE 29

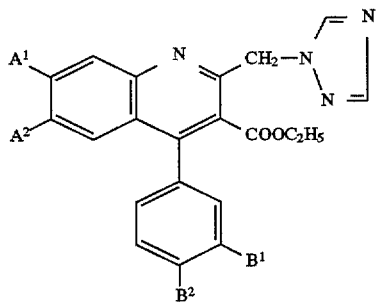

| Ex. No. | A¹ | A² | B¹ | B² | Yield (%) | mp (°C.) | Recrystallization Solvent |
|---|---|---|---|---|---|---|---|
| 216 | HO | CH₃O | CH₃O | CH₃O | 35 | 165–166¹⁾ | |
| 217 | CH₃O | HO | CH₃O | CH₃O | 38 | 215–216²⁾ | |
| 218 | CH₃O | CH₃O | HO | CH₃O | 62 | 232–233 | Dichloromethane-Hexane |

¹⁾NMR (δ ppm in CDCl₃): 0.88(3H, t, J=7.2Hz), 3.84(3H, s), 3.86(3H, s), 3.95(2H, q, J=7.2Hz), 3.97(3H, s), 5.73(2H, s), 6.88–7.01(5H, m), 7.52(1H, s), 7.94(1H, s), 8.37(1H, s).
²⁾NMR (δ ppm in CDCl₃): 0.86(3H, t, J=7.0Hz), 3.85(3H, s), 3.94(2H, q, J=7.0Hz), 3.98(3H, s), 4.07(3H, s), 5.73(2H, s), 6.20(1H, broad), 6.82–6.98(3H, m), 7.08(1H, s), 7.42(1H, s), 7.93(1H, s), 8.27(1H, s).

EXAMPLE 219

Titanium tetrachloride (TiCl₄)(288 mg) was added at 0° C. to a solution of ethyl 4-(3,4-diisopropoxyphenyl)-6,7-dimethoxy-2-(1,2,4-triazol-1-ylmethyl)quinoline-3-carboxylate (116.0 mg) in dichloromethane (2.5 ml), and the mixture was stirred at the same temperature for 6 hours. The reaction mixture was poured into water and extracted with chloroform. The chloroform layer was washed with a saturated aqueous sodium bicarbonate solution and water, and dried over magnesium sulfate. The solvent was evaporated. The residual oil was subjected to column chromatography on silica gel. The fractions eluted with ethyl acetate/chloroform(7/3, v/v) gave ethyl 4-(3,4-dihydroxyphenyl)-6,7-dimethoxy-2-(1,2,4-triazol-1-ylmethyl)quinoline-3-carboxylate (20.0 mg, 21%). mp. 122°–124° C.

NMR (δ ppm in CDCl₃): 0.78 (3H,t,J=7.0 Hz), 3.78 (3H,s), 3.86 (2H,q,J=7.0 Hz), 4.00 (3H,s), 5.71 (2H,s), 6.60 (1H, broad s), 6.68–6.79 (2H,m), 6.92 (1H,s), 6.97 (1H,d, J=8.0 Hz), 7.37 (1H,s), 7.95 (1H,s), 8.35 (1H,s), 8.70 (1H, broad s).

EXAMPLE 220

Titanium tetrachloride (TiCl₄)(316 mg) was added at 0° C. to a solution of ethyl 4-(3,4-diisopropoxyphenyl)-6-isopropoxy-7-methoxy-2-(1,2,4-triazol-1-ylmethyl) quinoline-3-carboxylate (96.0 mg) in dichloromethane (1.0 ml), and the mixture was stirred at the same temperature for 10 hours. The reaction mixture was poured into water and extracted with ethyl acetate. The ethyl acetate layer was washed with a saturated aqueous sodium bicarbonate solution and water, and dried over magnesium sulfate. The solvent was evaporated. The residual oil was subjected to column chromatography on silica gel. The fractions eluted with ethyl acetate/methanol (10/1, v/v) gave ethyl 4-(3,4-dihydroxyphenyl)-6-hydroxy-7-methoxy-2-(1,2,4-triazol-1-ylmethyl)quinoline-3-carboxylate (19.0 mg, 26%). mp. 264°–266° C.

NMR (δ ppm in CDCl₃): 0.88 (3H,t,J=7.0 Hz), 3.93 (2H,q,J=7.0 Hz), 3.94 (3H,s), 5.63 (2H,s), 6.52 (1H,dd,J= 8.2&2.2 Hz), 6.67 (1H,d,J=2.2 Hz), 6.85 (1H,d, J=8.2 Hz), 6.98 (1H,s), 7.29 (1H,s), 7.94 (1H,s), 8.57 (1H,s), 9.17 (1H,s), 9.21 (1H,s), 10.00 (1H,s).

EXAMPLE 221

Conc. sulfuric acid (0.03 ml) was added to a mixture of 2-amino-4,5,3',4'-tetramethoxybenzophenone (453 mg), ethyl 6-(1-imidazolyl)-3-oxohexanoate (320 mg) and acetic acid (5 ml), and the mixture was stirred at 100° C. for 2 hours. The reaction mixture was concentrated under reduced pressure. The residue was poured into water, and the mixture was made alkaline with 2N sodium hydroxide and extracted with chloroform. The chloroform layer was washed with water and dried over magnesium sulfate, and the solvent was evaporated. The residual oil was subjected to column chromatography on silica gel. The fractions eluted with chloroform/methanol (50/1, v/v) gave ethyl 6,7-dimethoxy-4-(3,4-dimethoxyphenyl)-2-[3-(1-imidazolyl)propyl] quinoline-3-carboxylate (310.0 mg, 43%) which was then recrystallized from ethyl acetate-hexane. Colorless prisms. mp. 164°–165° C.

EXAMPLE 222

According to the same manner as that described in Example 221, ethyl 6,7-dimethoxy-4-(3,4-dimethoxyphenyl)-2-[3-(1,2,4-triazol-1-yl)propyl] quinoline-3-carboxylate was obtained and recrystallized from ethanol. Colorless prisms. mp. 141°–142° C.

EXAMPLE 223

According to the same manner as that described in Example 221, ethyl 6,7-dimethoxy-4-(3,4- dimethoxyphenyl)-2-[4-(1-imidazolyl)butyl]quinoline-3-carboxylate was obtained and recrystallized from ethyl acetate-hexane. Colorless prisms. mp. 119°–120° C.

EXAMPLE 224

A mixture of ethyl 6,7-dimethoxy-4-(3,4-dimethoxyphenyl)-2-(1,2,4-triazol-1-ylmethyl)quinoline-3-carboxylate (3.0 g), 2N sodium hydroxide (15.6 ml) and ethanol (50 ml) was stirred under reflux for 8 hours. The reaction mixture was ice-cooled, adjusted to pH 5 with 2N hydrochloric acid and concentrated under reduced pressure. The residue was dissolved in ethanol, the insoluble materials were filtered off, and the filtrate was concentrated. The residual oil was subjected to column chromatography on silica gel. The fractions eluted with chloroform/methanol (4/1, v/v) gave 6,7-dimethoxy-4-(3,4-dimethoxyphenyl)-2-(1,2,4-triazol-1-ylmethyl)quinoline-3-carboxylic acid (1.3 g, 46%) which was then recrystallized from dichloromethane-ethanol. Colorless prisms. mp. 270°–271° C. (decomposition).

EXAMPLE 225

Oily sodium hydride (60%, 0.156 g) was added to a solution of 1H-1,2,4-triazole (0.27 g) in N,N-dimethylformamide (DMF)(20 ml), and the mixture was stirred at room temperature for 15 minutes. Then ethyl 2-chloromethyl-6,7-dimethoxy-4-(3,4-dimethoxyphenyl)quinoline-3-carboxylate 1-oxide (1.5 g) was added, and the mixture was stirred at 80° C. for 45 minutes. The reaction mixture was poured into water and extracted with dichloromethane. The dichloromethane layer was washed with water and dried over magnesium sulfate, and the solvent was evaporated. The residual oil was subjected to column chromatography on silica gel. The fractions eluted with chloroform/methanol (30/1, v/v) gave ethyl 6,7-dimethoxy-4-(3,4-dimethoxyphenyl)-2-(1,2,4-triazol-1-ylmethyl)quinoline-3-carboxylate 1-oxide (0.8 g, 50%) which was then recrystallized from dichloromethanehexane. Colorless prisms. mp. 221°–222° C.

EXAMPLE 226

According to the same manner as that described in 181, ethyl 6,7-dimethoxy-4-(3-propoxy-4-methoxyphenyl)-2-(1,2,4-triazol-1-ylmethyl)quinoline-3-carboxylate was obtained and recrystallized from ethanol. Colorless prisms. mp. 127°–128° C.

EXAMPLE 227

In the column chromatography in Example 226, the fractions eluted thereafter gave ethyl 6,7-dimethoxy-4-(3-propoxy-4-methoxyphenyl)-2-(1,2,4-triazol-4-ylmethyl)quinoline-3-carboxylate which was then recrystallized from ethanol. Colorless needles. mp. 154°–155° C.

EXAMPLE 228

According to the same manner as that described in 181, ethyl 4-(3,4-dimethoxyphenyl)-6,7-ethylenedioxy-2-(1,2,4-triazol-1-ylmethyl)quinoline-3-carboxylate was obtained and recrystallized from ethanol. Colorless needles. mp. 138°–140° C.

EXAMPLE 229

In the column chromatography in Example 228, the fractions eluted thereafter gave ethyl 4-(3,4-dimethoxyphenyl)-6,7-ethylenedioxy-2-(1,2,4-triazol-4-ylmethyl)quinoline-3-carboxylate which was then recrystallized from ethanol. Colorless needles. mp. 237°–239° C.

EXAMPLE 230

According to the same manner as that described in 181, ethyl 6,7-dimethoxy-4-(3,4-dimethoxyphenyl)-2-(1,2,3-triazol-1-ylmethyl )quinoline-3-carboxylate was obtained and recrystallized from ethanol-dichloromethane. Colorless prisms. mp. 195°–196° C.

Elemental Analysis: Calcd. for $C_{25}H_{26}N_4O_6 \cdot 1/4C_2H_5OH$: C,62.50; H,5.66; N,11.43 Found: C,62.29; H,5.53; N,11.30

EXAMPLE 231

In the column chromatography in Example 230, the fractions eluted thereafter gave ethyl 6,7-dimethoxy-4-(3,4-dimethoxyphenyl)-2-(1,2,3-triazol-2-ylmethyl )quinoline-3-carboxylate which was then recrystallized from ethanol-dichloromethane. Colorless needles. mp. 163°–164° C.

Elemental Analysis: Calcd. for $C_{25}H_{26}N_4O_6 \cdot 1/2C_2H_5OH$: C,62.27; H,5.83; N,11.17 Found: C,61.98; H,5.69; N,11.10

EXAMPLE 232

In the column chromatography in Example 211, the fractions eluted thereafter gave ethyl 6,7-dimethoxy-4-(3-isopropoxy-4-methoxyphenyl)-2-(1,2,4-triazol-4-ylmethyl)quinoline-3-carboxylate which was then recrystallized from ethyl acetate-hexane. Colorless prisms. mp. 170°–171° C.

EXAMPLE 233

In the column chromatography in Example 212, the fractions eluted thereafter gave ethyl 6,7-dimethoxy-4-(4-isopropoxy-3-methoxyphenyl)-2-(1,2,4-triazol-4-ylmethyl)quinoline-3-carboxylate which was then recrystallized from ethyl acetate-hexane. Colorless prisms. mp. 178°–179° C.

EXAMPLE 234

Oily sodium hydride (60%, 0.117 g) was added to a solution of 2-hydroxypyridine (0.277 g) in N,N-dimethylformamide (DMF)(10 ml), and the mixture was stirred at room temperature for 15 minutes. To this solution was added ethyl 6,7-dimethoxy-4-(3,4-dimethoxyphenyl)-2-iodomethylquinoline-3-carboxylate(1.2 g) . The mixture was stirred at room temperature for 8 hours, poured into water and extracted with ethyl acetate. The ethyl acetate layer was washed with water and dried over magnesium sulfate, and the solvent was evaporated. The residual oil was subjected to column chromatography on silica gel. The fractions eluted with chloroform/ethyl acetate (10/1, v/v) gave ethyl 2-(1,2-dihydro-2-oxopyridine-1-ylmethyl)-6,7-dimethoxy-4-(3,4-dimethoxyphenyl)quinoline-3-carboxylate (0.64 g, 57%) which was then recrystallized from ethanol. Colorless prisms. mp. 154°–156° C.

EXAMPLE 235

According to the same manner as that described in Example 177, 2-[2-(1-imidazolyl)ethyl]-6,7-dimethoxy-4-(3,4-dimethoxyphenyl)quinazoline was obtained and recrystallized from ethyl acetate. Colorless prisms. mp. 147°–148° C.

EXAMPLE 236

According to the same manner as that described in Example 166, ethyl 2-(benzimidazol-1-ylmethyl)-6,7- dimethoxy-4-(3,4-dimethoxyphenyl)quinoline-3-carboxylate was obtained by the reaction of ethyl 2-bromomethyl-6,7-dimethoxy-4-(3,4-dimethoxyphenyl)quinoline-3-carboxylate with benzimidazole, and recrystallized from ethanol. Colorless prisms. mp. 99°–100° C.

EXAMPLE 237

According to the same manner as that described in Example 181, methyl 6,7-dimethoxy-4-(3,4-dimethoxyphenyl)-2-(1,2,4-triazol-1-ylmethyl)quinoline-3-carboxylate was obtained by the reaction of methyl 2-chloromethyl-6,7-dimethoxy-4-(3,4-dimethoxyphenyl)quinoline-3-carboxylate with 1H-1,2,4-triazole, and recrystallized from ethanol. Colorless prisms. mp. 218°–220° C.

EXAMPLE 238

According to the same manner as that described in Example 166, propyl 6,7-dimethoxy-4-(3,4-dimethoxyphenyl)-2-(imidazol-1-ylmethyl)quinoline-3-carboxylate was obtained by the reaction of propyl 2-bromomethyl-6,7-dimethoxy-4-(3,4-dimethoxyphenyl)quinoline-3-carboxylate with imidazole, and recrystallized from ethanol. Colorless prisms. mp. 166°–168° C.

EXAMPLE 239

According to the same manner as that described in Example 166, butyl 6,7-dimethoxy-4-(3,4-dimethoxyphenyl)-2-(imidazol-1-ylmethyl)quinoline-3-carboxylate was obtained by the reaction of butyl 2-bromomethyl-6,7-dimethoxy-4-(3,4-dimethoxyphenyl)quinoline-3-carboxylate with imidazole, and recrystallized from ethanol. Colorless prisms. mp. 140°–141° C.

EXAMPLE 240

According to the same manner as that described in Example 181, ethyl 6-chloro-4-phenyl-2-(1,2,4-triazol-1-ylmethyl)quinoline-3-carboxylate was obtained by the reaction of ethyl 6-chloro-2-chloromethyl-4-phenylquinoline-3-carboxylate with 1H-1,2,4-triazole, and recrystallized from ethanol. Colorless prisms. mp. 114°–116° C.

EXAMPLES 241 to 248

According to the same manner as that described in Example 166, the compounds in Table 30 were obtained.

TABLE 30

| Ex. No. | $A^1, A^2$ | B | —N‹R | Yield (%) | mp (°C.) | Recrystallization Solvent |
|---|---|---|---|---|---|---|
| 241 | 6-Cl, H | —C₆H₄—Cl | imidazolyl | 34 | 112–114 | Ethanol |
| 242 | 6-CH₃, H | —C₆H₅ | imidazolyl | 30 | 121–123 | Ethanol |
| 243 | 6,7-(CH₃)₂ | —C₆H₄—Cl | imidazolyl | 40 | 133–135 | Ethanol |
| 244 | 6,7-(CH₃O)₂ | —C₆H₅ | imidazolyl | 57 | 143–144 | Ethanol |
| 245 | 6,7-(CH₃O)₂ | —C₆H₄—CH₃ | imidazolyl | 48 | 139–141 | Ethyl acetate-Hexane |

TABLE 30-continued

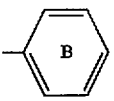

| Ex. No. | A¹, A² | —B (ring) | —N R (ring) | Yield (%) | mp (°C.) | Recrystallization Solvent |
|---|---|---|---|---|---|---|
| 246 | 6,7-(OCH$_2$CH$_2$O) | —⌬—OCH$_3$ | —N⟨triazole⟩ | 68 | 154–156 | Ethanol |
| 247 | 6,7-(CH$_3$O)$_2$ | —⌬(OCH$_3$)(OCH$_3$) | —N⟨indole⟩ | 70 | 143–144 | Ethanol-Hexane |
| 248 | 6,7-(CH$_3$O)$_2$ | —⌬(OCH$_3$)(OCH$_3$) | —N⟨indole-CHO⟩ | 75 | 160–161 | Dichloromethane-Isopropyl ether |

EXAMPLE 249

A solution of hydrogen chloride in ethanol (23%, 0.172 g) was added dropwise at room temperature to a suspension of ethyl 6,7-dimethoxy-4-(3-isopropoxy-4-methoxyphenyl)-2-(1,2,4-triazol-1-ylmethyl)quinoline-3-carboxylate (0.5 g) in ethanol (10 ml)-dichloromethane (2 ml). The mixture was stirred at room temperature for 15 minutes and concentrated under reduced pressure. The residue was treated with isopropyl ether, and the solid was collected by filtration and recrystallized from ethanol to give ethyl 6,7-dimethoxy-4-(3-isopropoxy-4-methoxyphenyl)-2-(1,2,4-triazol-1-ylmethyl)quinoline-3-carboxylate hydrochloride (0.211 g, 39%). Yellow crystals. mp. 93°–95° C.

EXAMPLE 250

Oily sodium hydride (60%, 0.27 g) was added to a solution of morpholine (0.537 g) in N,N-dimethylformamide (20 ml), and the mixture was stirred at room temperature for 15 minutes. Then ethyl 2-chloromethyl-4-(3,4-dimethoxyphenyl)-6,7-dimethoxyquinoline-3-carboxylate (2.5 g) was added. The resulting mixture was stirred at 100° C. for 2 hours, poured into water and extracted with ethyl acetate. The ethyl acetate layer was washed with water and dried over magnesium sulfate, and the solvent was evaporated. The crystals were collected by filtration and then recrystallized from ethanol to give ethyl 4-(3,4-dimethoxyphenyl)-6,7-dimethoxy-2-morpholinomethylquinoline-3-carboxylate (1.9 g, 68%). Colorless prisms. mp. 146°–147° C.

EXAMPLE 251

A mixture of ethyl 2-chloromethyl-4-(3,4-dimethoxyphenyl)-6,7-dimethoxyquinoline-3-carboxylate (1.0 g), piperazine (1.15 g) and methanol (15 ml) was stirred at room temperature for 36 hours. The reaction mixture was concentrated under reduced pressure, and 6N HCl (30 ml) was added to the residue. The resulting mixture was washed with dichloromethane. The aqueous layer was neutralized with 2N NaOH and extracted with dichloromethane. The dichloromethane layer was washed with water and dried over magnesium sulfate, and the solvent was evaporated. The crystals were collected by filtration and recrystallized from dichloromethane-hexane to give ethyl 4-(3,4-dimethoxyphenyl)-6,7-dimethoxy-2-piperazinomethylquinoline-3-carboxylate (0.43 g, 39%). Colorless prisms. mp. 192°–193° C.

EXAMPLE 252

Oily sodium hydride (60%, 0.753 g) was added to a solution of thiomorpholine (1.8 g) in N,N-dimethylformamide (50 ml), and the mixture was stirred at room temperature for 15 minutes. Then ethyl 2-chloromethyl-4-(3,4-dimethoxyphenyl)-6,7-dimethoxyquinoline-3-carboxylate (6.0 g) was added. The resulting mixture was stirred at room temperature overnight, poured into water and extracted with ethyl acetate. The ethyl acetate layer was washed with water and dried over magnesium sulfate, and the solvent was evaporated. The residue was subjected to column chromatography on silica gel. The fractions eluted with chloroform/ethyl acetate (7/3, v/v) gave ethyl 4-(3,4-dimethoxyphenyl)-6,7-dimethoxy-2-thiomorpholinomethylquinoline-3-carboxylate (1.4 g, 42%) which was then recrystallized from ethanol. Colorless prisms. mp. 148°–149° C.

EXAMPLE 253

Oily sodium hydride (60%, 0.466 g) was added to a solution of N-methylhomopiperazine (1.23 g) in N,N-dimethylformamide (40 ml), and the mixture was stirred at room temperature for 15 minutes. Then ethyl 2-chloromethyl-4-(3,4-dimethoxyphenyl)-6,7-dimethoxyquinoline-3-carboxylate (4.0 g) was added. The resulting mixture was stirred at 100° C. for 3.5 hours, poured into water and extracted with ethyl acetate. The ethyl acetate layer was washed with water and dried over magnesium sulfate, and the solvent was evaporated. The residue was subjected to column chromatography on silica gel. The fractions eluted with chloroform/methanol (5/1, v/v) gave ethyl 4-(3,4-dimethoxyphenyl)-6,7-dimethoxy-2-[(4-methylhomopiperazino)methyl]quinoline-3-carboxylate (1.0 g, 22%) which was then recrystallized from ethyl acetate-hexane. Colorless prisms. mp. 157°–159° C.

EXAMPLE 254

A mixture of ethyl 2-chloromethyl-4-(3,4-dimethoxyphenyl)-6,7-dimethoxyquinoline-3-carboxylate (4.0 g), diethylamine (1.28 g) and methanol (45 ml) was stirred at room temperature for 4 days. The reaction mixture was poured into water and extracted with dichloromethane. The dichloromethane layer was washed with water and dried over magnesium sulfate, and the solvent was evaporated. The residue was subjected to column chromatography on silica gel. The fractions eluted with ethyl acetate gave ethyl 2-(N,N-diethylaminomethyl)-4-(3,4-dimethoxyphenyl)-6,7-dimethoxyquinoilne-3-carboxylate (0.51 g, 18%) which was then recrystallized from ethyl acetate-hexane. Colorless prisms. mp. 130°–131° C.

EXAMPLE 255

A mixture of ethyl 2-chloromethyl-6,7-dimethoxy-4-(4-methoxyphenyl)quinoline-3-carboxylate (2.0 g), morpholine (2.5 g) and methanol (30 ml) was stirred at room temperature for 17 hours. The reaction mixture was concentrated under reduced pressure, and dichloromethane was added to the residue. The resulting mixture was washed with water and dried over magnesium sulfate, and the solvent was evaporated. The crystals were collected by filtration and recrystallized from ethanol to give ethyl 6,7-dimethoxy-4-(4-methoxyphenyl)-2-morpholinomethylquinoilne-3-carboxylate (1.65 g, 74%). Colorless prisms. mp. 165°–166° C.

EXAMPLE 256

According to the same manner as that described in Example 255, ethyl 6,7-dimethoxy-4-(4-methoxyphenyl)-2-piperidinomethylquinoline-3-carboxylate was obtained and recrystallized from ethanol. Colorless prisms. mp. 129°–130° C.

EXAMPLE 257

A mixture of ethyl 2-chloromethyl-6,7-dimethoxy-4-(2-methoxyphenyl)quinoline-3-carboxylate (1.0 g), morpholine (1.25 g) and ethanol (13 ml) was stirred at room temperature for 3 days. The crystals were collected by filtration and recrystallized from ethyl acetate-hexane to give ethyl 6,7-dimethoxy-4-(2-methoxyphenyl)-2-morpholinomethylquinoilne-3-carboxylate (0.76 g, 68%). Colorless prisms. mp. 153°–154° C.

EXAMPLE 258

According to the same manner as that described in Example 255, ethyl 4-(3,4-dimethoxyphenyl)-6,7-ethylenedioxy-2-morpholinomethylquinoline-3-carboxylate was obtained and recrystallized from ethanol. Colorless needles. mp. 174°–175° C.

EXAMPLE 259

According to the same manner as that described in Example 255, ethyl 4-(3,4-dimethoxyphenyl)-6,7-ethylenedioxy-2-piperidinomethylquinoline-3-carboxylate was obtained and recrystallized from ethanol. Colorless prisms. mp. 158°–160° C.

EXAMPLE 260

According to the same manner as that described in Example 255, ethyl 4-(3,4-dimethoxyphenyl)-6,7-diethoxy-2-morpholinomethylquinoline-3-carboxylate was obtained and recrystallized from ethanol. Colorless prisms. mp. 147°–148° C.

EXAMPLE 261

According to the same manner as that described in Example 255, ethyl 4-(3,4-dimethoxyphenyl)-6,7-diethoxy-2-piperidinomethylquinoline-3-carboxylate was obtained and recrystallized from ethanol. Colorless prisms. mp. 154°–155° C.

EXAMPLE 262

According to the same manner as that described in Example 255, ethyl 6-chloro-2-morpholinomethyl-4-phenylquinoline-3-carboxylate was obtained and recrystallized from ethanol. Colorless prisms. mp. 161°–163° C.

EXAMPLE 263

A mixture of ethyl 2-chloromethyl-4-(3-isopropoxy-4-methoxyphenyl)-6,7-dimethoxyquinoline-3-carboxylate (3.0 g), morpholine (2.76 g) and ethanol (50 ml)-dichloromethane (5 ml) was stirred at room temperature overnight. The reaction mixture was concentrated under reduced pressure, and dichloromethane (50 ml) was added to the residue. The dichloromethane layer was washed with water and dried over magnesium sulfate, and the solvent was evaporated. The residue was subjected to column chromatography on silica gel. The fractions eluted with chloroform-ethyl acetate (1/1, v/v) gave ethyl 4-(3-isopropoxy-4-methoxyphenyl)-6,7-dimethoxy-2-morpholinomethylquinoilne-3-carboxylate as an oil. The oil was dissolved in ethanol (20 ml), a solution of hydrogen chloride in ethanol (23%, 1.05 g) was added, and the mixture was stirred at room temperature for 10 minutes. The solvent was evaporated under reduced pressure, and the crystals were collected by filtration and recrystallized from ethanol-ether to give ethyl 4-(3-isopropoxy-4-methoxyphenyl)-6,7-dimethoxy-2-morpholinomethylquinoline-3-carboxylate hydrochloride (1.62 g, 45%). Colorless crystals. mp. 185°–188° C.

Elemental Analysis: Calcd. for $C_{29}H_{37}N_2O_7Cl.H_2O$: C,60.15; H,6.79; N,4.84 Found: C,60.51; H,6.58; N,4.73

EXAMPLE 264

According to the same manner as that described in Example 263, ethyl 4-(3-isopropoxy-4-methoxyphenyl)-6,7-dimethoxy-2-piperidinomethylquinoline-3-carboxylate hydrochloride was obtained and recrystallized from ethanol-ether. Colorless crystals. mp. 207°–210° C.

Elemental Analysis: Calcd. for $C_{30}H_{39}N_2O_6Cl \cdot 1/2H_2O$: C,63.43; H,7.10; N,4.93 Found: C,63.15; H,7.02; N,4.80

EXAMPLE 265

According to the same manner as that described in Example 263, ethyl 2-(N,N-dipentylaminomethyl)-4-(3,4-dimethoxyphenyl)-6,7-dimethoxyquinoline-3-carboxylate dihydrochloride was obtained and recrystallized from dichloromethane-ethyl acetate. Yellow powder. mp. 93°–95° C.

Elemental Analysis: Calcd. for $C_{33}H_{48}N_2O_6Cl_2 \cdot 3/2H_2O$: C,59.45; H,7.71; N,4.20 Found: C,59.58; H,7.88; N,4.14

EXAMPLE 266

According to the same manner as that described in Example 250, ethyl 4-(3,4-dimethoxyphenyl)-6,7-dimethoxy-2-piperidinomethylquinoline-3-carboxylate was obtained and recrystallized from ethanol. Colorless prisms. mp. 148°–149° C.

EXAMPLE 267

According to the same manner as that described in Example 250, ethyl 4-(3,4-dimethoxyphenyl)-6,7-dimethoxy-2-pyrrolidinomethylquinoline-3-carboxylate was obtained and recrystallized from ethyl acetate-hexane. Colorless prisms. mp. 139°–140° C.

EXAMPLE 268

A mixture of propyl 2-bromomethyl-4-(3,4-dimethoxyphenyl)-6,7-dimethoxyquinoline-3-carboxylate (1.5 g), piperidine (1.27 g) and dichloromethane (30 ml) was stirred at room temperature for 2 days. The reaction mixture was washed with water and dried over magnesium sulfate, and the solvent was evaporated. The residue was subjected to column chromatography on silica gel. The fractions eluted with chloroform-ethyl acetate (10/1, v/v) gave propyl 4-(3,4-dimethoxyphenyl)-6,7-dimethoxy-2-piperidinomethylquinoline-3-carboxylate (0.8 g, 53%) which was then recrystallized from ethyl acetate-hexane. Colorless prisms. mp. 129°–131° C.

EXAMPLE 269

According to the same manner as that described in Example 268, butyl 4-(3,4-dimethoxyphenyl)-6,7-dimethoxy-2-piperidinomethylquinoline-3-carboxylate was obtained and recrystallized from ethyl acetate-hexane. Colorless needles. mp. 154°–155° C.

EXAMPLES 270 to 277

According the same manner as that described in Example 254, the compounds in Table 31 were obtained.

TABLE 31

| Ex. No. | $A^1$, $A^2$ | R | Yield (%) | mp (°C.) | Recrystallization Solvent |
|---|---|---|---|---|---|
| 270 | 6,7-$(CH_3O)_2$ | $CH_3$ | 65 | 137–138 | Ethyl acetate-Hexane |
| 271 | 6,7-$(CH_3O)_2$ | $C_3H_7$ | 47 | 92–93 | Ethanol-Hexane |
| 272 | 6,7-$(CH_3O)_2$ | $C_4H_9$ | 50 | 90–92 | Ethanol-Hexane |
| 273 | 6,7-$(CH_3O)_2$ | $(CH_3)_2CH$ | 20 | 134–135 | Ethanol-Hexane |
| 274 | 6,7-$(CH_3O)_2$ | $HOCH_2CH_2$ | 66 | 117–119[1] | Ethyl acetate-Hexane |
| 275 | 6,7-$(CH_3O)_2$ | cyclohexyl | 14 | 174–175[2] | Ethyl acetate-Hexane |
| 276 | 6,7-$(CH_3O)_2$ | $C_6H_5CH_2$ | 36 | 56–58[3] | |
| 277 | 6,7-$(C_2H_5O)_2$ | $C_2H_5$ | 44 | 86–88 | Ethyl acetate-Hexane |

[1] 1/2 Hydrate.
[2] 1/4 Hydrate.
[3] Amorphous solid. NMR (δ ppm in $CDCl_3$): 0.97(3H, t, J=7Hz), 3.59(4H, s), 3.78(3H, s), 3.88(3H, s), 3.97(3H, s), 3.99(2H, q, J=7Hz), 4.04(3H, s), 4.13(2H, s), 6.84–7.02(4H, m), 7.10–7.40(10H, m), 7.42(1H, s).

EXAMPLE 278

A mixture of 2-chloromethyl-4-(3,4-dimethoxyphenyl)-6,7-dimethoxyquinazoline (2.0 g), piperidine (2.27 g) and ethanol (40 ml)-dichloromethane (10 ml) was stirred at room temperature for 3 days. The reaction mixture was concentrated under reduced pressure, and dichloromethane (50 ml) was added to the residue. The dichloromethane layer was washed with water and dried over magnesium sulfate, and the solvent was evaporated. The residue was subjected to column chromatography on silica gel. The fractions eluted with chloroform-ethyl acetate (1/1, v/v) gave 4-(3,4-dimethoxyphenyl)-6,7-dimethoxy-2-piperidinomethylquinazoline (1.46 g, 65%) which was then recrystallized from ethyl acetate-hexane. Colorless needles. mp. 130°–132° C.

EXAMPLE 279

According to the same manner as that described in Example 278, 4-(3,4-dimethoxyphenyl)-6,7-dimethoxy-2-morpholinomethylquinazoline was obtained and recrystallized from ethyl acetate-hexane. Colorless prisms. mp. 148°–150° C.

EXAMPLE 280

According to the same manner as that described in Example 278, 2-(N,N-diethylaminomethyl)-4-(3,4-dimethoxyphenyl)-6,7-dimethoxyquinazoline was obtained and recrystallized from ethyl acetate-hexane. Colorless prisms. mp. 111°–113° C.

EXAMPLE 281

According to the same manner as that described in Example 278, ethyl 2-(N-ethyl-N-propylaminomethyl)-4-(3,4-dimethoxyphenyl)-6,7-dimethoxyquinoline-3-carboxylate was obtained by the reaction of ethyl 2-bromomethyl-4-(3,4-dimethoxyphenyl)-6,7-dimethoxyquinoline-3-carboxylate with N-ethyl-N-propylamine, and recrystallized from ethyl acetate-hexane. Colorless prisms. mp. 105°–106° C.

EXAMPLE 282

A mixture of 2-(2-bromoethyl)-4-(3,4-dimethoxyphenyl)-6,7-dimethoxyquinazoline (0.486 g), diethylamine (0.41 g) and dichloromethane (10 ml) was stirred under reflux for 6 hours. The reaction mixture was poured into water and extracted with dichloromethane. The dichloromethane layer was washed with water and dried over magnesium sulfate, and the solvent was evaporated. The residue was subjected to column chromatography on silica gel. The fractions eluted with chloroform-ethyl acetate (1/1, v/v) gave 2-[2-(N,N-diethylamino)ethyl]-4-(3,4-dimethoxyphenyl)- 6,7-dimethoxyquinazoline (0.040 g, 8%) which was then recrystallized from ethyl acetate-hexane. Colorless prisms. mp. 164°–166° C.

EXAMPLE 283

A mixture of ethyl 2-chloromethyl-4-(3,4-dimethoxyphenyl)-6,7-dimethoxyquinoline-3-carboxylate (3.0 g), N-methyl-N-cyclohexylamine (2.28 g) and ethanol (45 ml) was stirred under reflux for 6 hours. The reaction mixture was poured into water and extracted with dichloromethane. The dichloromethane layer was washed with water and dried over magnesium sulfate, and the solvent was evaporated. The residue was subjected to column chromatography on silica gel. The fractions eluted with chloroform gave ethyl 2-(N-cyclohexyl-N-methylaminomethyl)-4-(3,4-dimethoxyphenyl)-6,7-dimethoxyquinoline-3-carboxylate (2.80 g, 80%) which was then recrystallized from ethanol. Colorless prisms. mp. 172°–174° C.

EXAMPLES 284 to 290

According to the same manner as that described in Example 283, the compounds in Table 32 were obtained.

TABLE 32

| Ex. No. | $R^1$ | $R^2$ | Yield (%) | mp (°C.) | Recrystallization Solvent |
|---|---|---|---|---|---|
| 284 | $C_6H_5CH_2CH_2$ | $C_6H_5CH_2$ | 65 | 135–137 | Ethanol |
| 285 | $C_4H_9$ | $CH_3$ | 64 | 143–144 | Ethanol |
| 286 | $(CH_3)_2CHCH_2$ | $CH_3$ | 44 | 121–123 | Ethyl acetate-Hexane |
| 287 | $C_4H_9$ | $C_2H_5$ | 58 | 113–114 | Ethyl acetate-Hexane |
| 288 | $(C_2H_5)(CH_3)CH$ | $C_3H_7$ | 39 | 129–131 | Ethyl acetate-Hexane |
| 289 | $(CH_3)_3C$ | $C_2H_5$ | 51 | 120–121 | Ethyl acetate-Hexane |
| 290 | $CH_3$ | $C_2H_5$ | 63 | 139–140 | Ethyl acetate-Hexane |

EXAMPLE 291

According to the same manner as that described in Example 263, ethyl 2-(N,N-diethylaminomethyl)-4-(3-isopropoxy-4-methoxyphenyl)-6,7-dimethoxyquinoline-3-carboxylate dihydrochloride was obtained by the reaction of ethyl 2-chloromethyl-4-(3-isopropoxy-4-methoxyphenyl)-6,7-dimethoxyquinoline-3-carboxylate with diethylamine, and recrystallized from ethyl acetate-ether. Yellow powder. mp. 122°–124° C.

Elemental Analysis: Calcd. for $C_{29}H_{40}N_2O_6Cl_2 \cdot 1/2H_2O$: C,58.78; H,6.97; N,4.73 Found: C,58.84; H,7.00; N,4.69

EXAMPLE 292

According to the same manner as that described in Example 282, ethyl 6-chloro-4-(4-chlorophenyl)-2-(N,N- diethylaminomethyl)quinoline-3-carboxylate was obtained by the reaction of ethyl 6-chloro-2-chloromethyl-4-(4-chlorophenyl)-quinoline-3-carboxylate with diethylamine, and recrystallized from ethanol. Colorless prisms. mp. 132°–133° C.

EXAMPLE 293

According to the same manner as that described in Example 282, ethyl 6-chloro-2-(N,N-diethylaminomethyl)-4-phenylquinoline-3-carboxylate was obtained by the reaction of ethyl6-chloro-2-chloromethyl-4-phenylquinoline-3-carboxylate with diethylamine, and recrystallized from ethanol. Colorless prisms. mp. 107°–108° C.

REFERENCE EXAMPLE 1

A mixture of 2-amino-4,5,3',4'-tetramethoxybenzophenone (10.0 g), diethyl malonate (6.0 g) and 1,8-diazabicyclo[5.4.0]-7-undecene (DBU)(0.396 g) was stirred at 180° C. for 10 minutes. After cooling, ethanol was added to the reaction mixture, and the crystals were collected by filtration to give ethyl 6,7-dimethoxy-4-(3,4-dimethoxyphenyl)-2(1H)-quinolone-3-carboxylate (12.0 g, 91%) which was then recrystallized from chloroform-acetone. mp. 273°–276° C.

REFERENCE EXAMPLE 2

A mixture of ethyl 6,7-dimethoxy-4-(3,4-dimethoxyphenyl)-2(1H)-quinolone-3-carboxylate (6.8 g), Lawesson's reagent (8.0 g) and toluene (250 ml) was stirred under reflux for 18 hours. After cooling, the precipitated crystals were collected by filtration to give ethyl 6,7-dimethoxy-4-(3,4-dimethoxyphenyl)-2-mercaptoquinoline-3-carboxylate (5.0 g, 70%) which was then recrystallized from acetone. mp. 265°–266° C.

REFERENCE EXAMPLE 3

A mixture of ethyl 6,7-dimethoxy-4-(3,4-dimethoxyphenyl)-2(1H)-quinolone-3-carboxylate (5.0 g) and phosphorus oxychloride (POCl$_3$)(6.3 ml) was stirred at 100° to 110° C. for 80 minutes. The reaction mixture was concentrated under reduced pressure. The residue was poured into water, neutralized with an aqueous saturated sodium bicarbonate solution and extracted with chloroform. The chloroform layer was washed with water and dried over magnesium sulfate, and the solvent was evaporated. The residual oil was subjected to column chromatography on silica gel. The fractions eluted with chloroform gave ethyl 2-chloro-6,7-dimethoxy-4-(3,4-dimethoxyphenyl) quinoline-3-carboxylate (3.8 g, 73%) which was then recrystallized from ethyl acetate-hexane. mp. 168°–169° C.

REFERENCE EXAMPLE 4

A mixture of ethyl 2-chloromethyl-6,7-diethoxy-4-(3,4-dimethoxyphenyl)quinoline-3-carboxylate (7.1 g), triphenylphosphine (3.9 g) and toluene (70 ml) was stirred under reflux for 2 hours. After cooling, the resulting solid was collected by filtration to give [6,7-diethoxy-4-(3,4-dimethoxyphenyl)-3-ethoxycarbonylquinolin-2-yl]methyltriphenylphosphonium chloride (9.6 g, 87%). mp. 172°–174° C. (decomposition).

REFERENCE EXAMPLE 5

According to the same manner as that described in Reference Example 4, [6,7-dimethoxy-4-(3,4-dimethoxyphenyl)-3-ethoxycarbonylquinolin-2-yl] methyltriphenylphosphonium chloride was obtained. mp. 200°–202° C. (decomposition).

REFERENCE EXAMPLE 6

According to the same manner as that described in Reference Example 4, [6,7-dimethoxy-4-(4-methoxyphenyl)-3-ethoxycarbonylquinolin-2-yl] methyltriphenylphosphonium chloride was obtained. mp. 178°–180° C. (decomposition).

REFERENCE EXAMPLE 7

According to the same manner as that described in Reference Example 4, [6,7-dimethoxy-4-(3,4-dimethoxyphenyl)-quinazolin-2-yl] methyltriphenylphosphonium chloride was obtained. mp. 208°–210° C. (decomposition).

REFERENCE EXAMPLE 8

A mixture of benzyl 4-bromobutyrate (23.7 g), imidazole (8.1 g), potassium carbonate (14.0 g) and acetone (400 ml) was stirred under reflux for 6 hours. After cooling the mixture to room temperature, the insoluble material was filtered off, and the filtrate was concentrated. The residual oil was subjected to column chromatography on silica gel. The fractions eluted with ethyl acetate/methanol (20/1, v/v) gave benzyl 4-(1-imidazolyl)butyrate (7.3 g, 33%) as an oil.

NMR (δ ppm in CDCl$_3$): 2.11 (2H,m), 2.34 (2H,t,J=6.8 Hz), 3.99 (2H,t,J=6.8 Hz), 5.12 (2H,s), 6.87 (1H,s), 7.05 (1H,s), 7.30–7.40 (5H,m).

REFERENCE EXAMPLE 9

According to the same manner as that described in Reference Example 8, benzyl 4-(1,2,4-triazol-1-yl)butyrate was obtained as an oil in 88% yield.

NMR (δ ppm in CDCl$_3$): 2.14–2.42 (4H,m), 4.24 (2H,t, J=6.4 Hz), 5.13 (2H,s), 7.30–7.43 (5H,m), 7.94 (1H,s), 7.99 (1H,s).

REFERENCE EXAMPLE 10

According to the same manner as that described in Reference Example 8, benzyl 5-(1-imidazolyl)valerate was obtained as an oil by the reaction of benzyl 5-bromovalerate with imidazole.

NMR (δ ppm in CDCl$_3$): 1.55–1.90 (4H,m), 2.38 (2H,t, J=6.8 Hz), 3.93 (2H,t,J=7.0 Hz), 5.11 (2H,s), 6.87 (1H,s), 7.05 (1H,s), 7.25–7.50 (5H,m), 7.94 (1H,s), 7.99 (1H,s).

REFERENCE EXAMPLE 11

A mixture of benzyl 4-(1-imidazolyl)butyrate (7.4 g), palladium-carbon (5%)(1.0 g) and ethanol (400 ml) was subjected to catalytic hydrogenation at room temperature and 1 atm. The catalyst was filtered off, the filtrate was concentrated under reduced pressure, and the crystals were recrystallized from ethanol to give 4-(1-imidazolyl)butyric acid (3.4 g, 75%). Colorless prisms. mp. 125°–126° C.

REFERENCE EXAMPLE 12

According to the same manner as that described in Reference Example 11, benzyl 4-(1,2,4-triazol-1-yl)butyrate was subjected to catalytic hydrogenation to give 4-(1,2,4-triazol-1-yl)butyric acid which was then recrystallized from ethanol. Colorless prisms. mp. 137°–138° C.

REFERENCE EXAMPLE 13

According to the same manner as that described in Reference Example 11, benzyl 5-(1-imidazolyl)valerate was subjected to catalytic hydrogenation to give 5-(1-imidazolyl)valeric acid which was then recrystallized from ethanol. Colorless prisms. mp. 157°–158° C.

REFERENCE EXAMPLE 14

To a suspension of 4-(1-imidazolyl)butyric acid (0.5 g) in tetrahydrofuran (35 ml) was added 1,1'-carbonyldiimidazole (0.578 g) was added, and the mixture was stirred at room temperature for 6 hours. Then malonic acid monoethyl ester magnesium salt $(Mg(OCOCH_2COOC_2H_5)_2)$(1.02 g) was added, and the resulting mixture was stirred at room temperature for 18 hours. The reaction mixture was concentrated under reduced pressure, and the residue was dissolved in dichloromethane. The dichloromethane layer was washed with water and dried over magnesium sulfate, and the solvent was evaporated. The residual oil was subjected to column chromatography on silica gel. The fractions eluted with chloroform/methanol (30/1, v/v) gave ethyl 6-(1-imidazolyl)-3-oxohexanoate (0.32 g, 44%) as an oil.

NMR (δ ppm in $CDCl_3$): 1.28 (3H,t,J=7.4 Hz), 2.08 (2H,m), 2.53 (2H,t,J=6.6 Hz), 3.41 (2H,s), 4.00 (2H,t,J=6.6 Hz), 4.19 (2H,q,J=7.4 Hz), 6.91 (1H,s), 7.07 (1H,s), 7.46 (1H,s).

REFERENCE EXAMPLE 15

According to the same manner as that described in Reference Example 14, ethyl 6-(1,2,4-triazol-1-yl)-3-oxohexanoate was obtained as an oil from 4-(1,2,4-triazol-1-yl)butyric acid.

NMR (δ ppm in $CDCl_3$): 1.28 (3H,t,J=7.2 Hz), 2.19 (2H,m), 2.59 (2H,t,J=6.6 Hz), 3.43 (2H,s), 4.19 (2H,q,J=7.2 Hz), 4.23 (2H,t,J=6.6 Hz), 7.94 (1H,s), 8.07 (1H,s).

REFERENCE EXAMPLE 16

According to the same manner as that described in Reference Example 14, ethyl 7-(1-imidazolyl)-3-oxoheptanoate was obtained as an oil from 5-(1-imidazolyl)valeric acid.

NMR(δ ppm in $CDCl_3$): 1.27 (3H,t,J=7.4 Hz), 1.50–1.90 (4H,m), 2.58 (2H,t,J=6.6 Hz), 3.41 (2H,s), 3.95 (2H,t,J=7.0 Hz), 4.19 (2H,q,J=7.4 Hz), 6.90 (1H,s), 7.06 (1H,s), 7.47 (1H,s).

What is claimed is:

1. A method of inhibiting bone resorption in a mammal in need thereof which comprises administering to such mammal an effective amount of a compound of the formula (I):

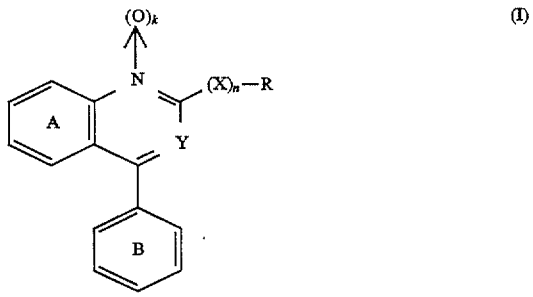

wherein
Y is a nitrogen atom or C—G in which G is an optionally esterified or optionally amidated carboxyl group, or hydroxymethyl group;

R is an optionally substituted hydrocarbon group or optionally substituted heterocyclic group;
X is an oxygen atom or optionally oxidized sulfur atom;
n is 0 or 1;
k is 0 or 1;
G and R may be linked together to form a ring;
each of the ring A and ring B may optionally be substituted;

or a pharmaceutically acceptable salt thereof.

2. The method of claim 1, wherein n is 0.

3. The method of claim 1, wherein n is 0 and the hydrocarbon group represented by R is a group of the formula:

$$-CH_2-X^1-Z^1$$

wherein $X^1$ is an oxygen atom, optionally oxidized sulfur atom or $-(CH_2)_m-$ in which m is an integer of 0 to 5; and $Z^1$ is an optionally substituted hydrocarbon group, optionally substituted heterocyclic group or optionally substituted amino group.

4. The method of claim 3, wherein $X^1$ is a thio group, sulfinyl group or sulfonyl group.

5. The method of claim 4, wherein $X^1$ is a thio group.

6. The method of claim 3, wherein $X^1$ is $-(CH_2)_m-$ and m is 0.

7. The method of claim 3, wherein $X^1$ is $-(CH_2)_m-$ and m is 1 or 2.

8. The method of claim 3, wherein the optionally substituted heterocyclic group represented by $Z^1$ is an aromatic 5-membered heterocyclic group containing 2 to 3 hetero atoms.

9. The method of claim 3, wherein $Z^1$ is an optionally substituted amino group.

10. The method of claim 1, wherein the optionally substituted heterocyclic group represented by R is an optionally substituted 5- to 7-membered heterocyclic group containing one sulfur atom, nitrogen atom or oxygen atom, an optionally substituted 5- to 6-membered heterocyclic group containing 2 to 4 nitrogen atoms, or an optionally substituted 5- to 6-membered heterocyclic group containing 1 to 2 nitrogen atoms and one sulfur atom or oxygen atom.

11. The method of claim 1, wherein Y is C—G.

12. The method of claim 1, wherein G is a ($C_{1-6}$ alkyl) oxycarbonyl group.

13. The method of claim 11, wherein G is an ethoxycarbonyl group.

14. The method of claim 1, wherein the ring A is substituted with at least one alkoxy group.

15. The method of claim 1, wherein the ring A is substituted with at least one methoxy group.

16. The method of claim 1, wherein the ring A is substituted with the same or different two alkoxy groups.

17. The method of claim 1, wherein the ring A is substituted with two methoxy groups.

18. The method of claim 1, wherein the ring A is substituted with two methoxy groups at the 6- and 7- positions of the quinoline ring or quinazoline ring.

19. The method of claim 1, wherein the ring B is substituted with at least one alkoxy group.

20. The method of claim 1, wherein the ring B substituted with at least one methoxy group.

21. The method of claim 1, wherein the ring B is substituted with at least one isoproxy group.

22. The method of claim 1, wherein the ring B substituted with the same or different two alkoxy groups.

23. The method of claim 1, wherein the ring B is substituted with one methoxy group.

24. The method of claim 1, wherein the ring B is substituted with an isoproxy group at the 3-position and a methoxy group at the 4-position.

25. The method of claim 1, wherein k is 0.

26. The method of claim 1, wherein the compound of the formula (I) is methyl 4-(3,4-dimethoxyphenyl)-2-ethyl-6,7-dimethoxyquinoline-3-carboxylate;

ethyl 6-chloro-2-methyl-4-(3,4-dimethoxyphenyl) quinoline-3-carboxylate;

6,7-dimethoxy-9-phenylfuro[3,4-b]quinoline-1(3H)-one;

ethyl 4-(3,4-dimethoxyphenyl)-6,7-dimethoxy-2-[(1-methylimidazol-2-yl)thiomethyl]quinoline-3-carboxylate;

4-(3,4-dimethoxyphenyl)-2-(2-hydroxyethylthiomethyl)-6,7-dimethoxyquinazoline;

4-(3,4-dimethoxyphenyl)-6,7-dimethoxy-2-[(4-methyl-1,2,4-triazol-3-yl)thiomethyl]quinazoline;

ethyl 4-(3,4-dimethoxyphenyl)-6,7-dimethoxy-2-[2-(1-methylimidazol-2-yl)ethyl]quinoline-3-carboxylate;

methyl 4-(3,4-dimethoxyphenyl)-6,7-dimethoxy-3-methoxycarbonylquinoline-2-acetate;

ethyl 4-(3,4-dimethoxyphenyl)-6,7-dimethoxy-2-(1,2,4-triazol-1-ylmethyl)quinoline-3-carboxylate;

ethyl 4-(3-isopropoxy-4-methoxyphenyl)-6,7-dimethoxy-2-(1,2,4-triazol-1-ylmethyl)quinoline-3-carboxylate;

ethyl 4-(4-hydroxy-3-methoxyphenyl)-6,7-dimethoxy-2-(1,2,4-triazol-1-ylmethyl)quinoline-3-carboxylate;

ethyl 7-hydroxy-6-methoxy-4-(3,4-dimethoxyphenyl)-2-(1,2,4-triazol-1-ylmethyl)quinoline-3-carboxylate;

ethyl 4-(3,4-dimethoxyphenyl)-6,7-dimethoxy-2-(1,2,4-triazol-1-ylmethyl)quinoline-3-carboxylate 1-oxide; or ethyl 2-(N,N-diethylaminomethyl)-4-(3,4-dimethoxyphenyl)-6,7-dimethoxyquinoline-3-carboxylate.

27. A method for preventing or treating osteoporosis in a mammal in need thereof which comprises administering to such mammal a therapeutically effective amount of a compound of the formula (I):

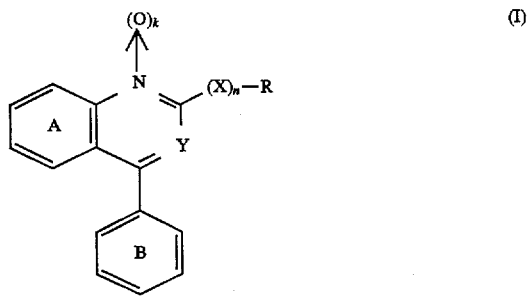

Y is a nitrogen atom or C—G in which G is an optionally esterified or optionally amidated carboxyl group, or hydroxymethyl group;

R is an optionally substituted hydrocarbon group or optionally substituted heterocyclic group;

X is an oxygen atom or optionally oxidized sulfur atom;

n is 0 or 1;

k is 0 or 1;

G and R may be linked together to form a ring;

each of the ring A and ring B may optionally be substituted;

or a pharmaceutically acceptable salt thereof.

28. The method of claim 27, wherein n is 0.

29. The method of claim 27, wherein n is 0 and the hydrocarbon group represented by R is a group of the formula:

$$-CH_2-X^1-Z^1$$

wherein $X^1$ is an oxygen atom, optionally oxidized sulfur atom or $-(CH_2)_m-$ in which m is an integer of 0 to 5; and $Z^1$ is an optionally substituted hydrocarbon group, optionally substituted heterocyclic group or optionally substituted amino group.

30. The method of claim 29, wherein $X^1$ is a thio group, sulfinyl group or sulfonyl group.

31. The method of claim 30, wherein $X^1$ is a thio group.

32. The method of claim 29, wherein $X^1$ is $-(CH_2)_m-$ and m is 0.

33. The method of claim 29, wherein $X^1$ is $-(CH_2)_m-$ and m is 1 or 2.

34. The method of claim 29, wherein the optionally substituted heterocyclic group represented by $Z^1$ is an aromatic 5-membered heterocyclic group containing 2 to 3 hetero atoms.

35. The method of claim 29, wherein $Z^1$ is an optionally substituted amino group.

36. The method of claim 27, wherein the optionally substituted heterocyclic group represented by R is an optionally substituted 5- to 7-membered heterocyclic group containing one sulfur atom, nitrogen atom or oxygen atom, an optionally substituted 5- to 6-membered heterocyclic group containing 2 to 4 nitrogen atoms, or an optionally substituted 5- to 6-membered heterocyclic group containing 1 to 2 nitrogen atoms and one sulfur atom or oxygen atom.

37. The method of claim 27, wherein Y is C—G.

38. The method of claim 37, wherein G is a $(C_{1-6}$ alkyl)oxycarbonyl group.

39. The method of claim 37, wherein G is an ethoxycarbonyl group.

40. The method of claim 27, wherein the ring A is substituted with at least one alkoxy group.

41. The method of claim 27, wherein the ring A is substituted with at least one methoxy group.

42. The method of claim 27, wherein the ring A is substituted with the same or different two alkoxy groups.

43. The method of claim 27, wherein the ring A is substituted with two methoxy groups.

44. The method of claim 27, wherein the ring A is substituted with two methoxy groups at the 6- and 7-positions of the quinoline ring or quinazoline ring.

45. The method of claim 27, wherein the ring B is substituted with at least one alkoxy group.

46. The method of claim 27, wherein the ring B is substituted with at least one methoxy group.

47. The method of claim 27, wherein the ring B is substituted with at least one isopropoxy group.

48. The method of claim 27, wherein the ring B is substituted with the same or different two alkoxy groups.

49. The method of claim 27, wherein the ring B is substituted with one methoxy group.

50. The method of claim 27, wherein the ring B is substituted with an isopropoxy group at the 3-position and a methoxy group at the 4-position.

51. The method of claim 27, wherein k is 0.

52. The method of claim 27, wherein the compound of the formula (I) is methyl 4-(3,4-dimethoxyphenyl)-2-ethyl-6,7-dimethoxyquinoline-3-carboxylate;

ethyl 6-chloro-2-methyl-4-(3,4-dimethoxyphenyl) quinoline-3-carboxylate;

6,7-dimethoxy-9-phenylfuro[3,4-b]quinoline-1(3H)-one;

ethyl 4-(3,4-dimethoxyphenyl)-6,7-dimethoxy-2-[(1-methylimidazol-2-yl)thiomethyl]quinoline-3-carboxylate;

4-(3,4-dimethoxyphenyl)-2-(2-hydroxyethylthiomethyl)-6,7-dimethoxyquinazoline;

4-(3,4-dimethoxyphenyl)-6,7-dimethoxy-2-[(4-methyl-1,2,4-triazol-3-yl)thiomethyl]quinazoline;

ethyl 4-(3,4-dimethoxyphenyl)-6,7-dimethoxy-2-[2-(1-methylimidazol-2-yl)ethyl]quinoline-3-carboxylate;

methyl 4-(3,4-dimethoxyphenyl)-6,7-dimethoxy-3-methoxycarbonylquinoline-2-acetate;

ethyl 4-(3,4-dimethoxyphenyl)-6,7-dimethoxy-2-(1,2,4-triazol-1-ylmethyl)quinoline-3-carboxylate;

ethyl 4-(3-isopropoxy-4-methoxyphenyl)-6,7-dimethoxy-2-(1,2,4-triazol-1-ylmethyl)quinoline-3-carboxylate;

ethyl 4-(4-hydroxy-3-methoxyphenyl)-6,7-dimethoxy-2-(1,2,4-triazol-1-ylmethyl)quinoline-3-carboxylate;

ethyl 7-hydroxy-6-methoxy-4-(3,4-dimethoxyphenyl)-2-(1,2,4-triazol-1-ylmethyl)quinoline-3-carboxylate;

ethyl 4-(3,4-dimethoxyphenyl)-6,7-dimethoxy-2-(1,2,4-triazol-1-ylmethyl)quinoline-3-carboxylate 1-oxide; or ethyl 2-(N,N-diethylaminomethyl)-4-(3,4-dimethoxyphenyl)-6,7-dimethoxyquinoline-3-carboxylate.

* * * * *